(12) United States Patent
Albericio et al.

(10) Patent No.: US 8,802,819 B2
(45) Date of Patent: Aug. 12, 2014

(54) DIKETOPIPERAZINE FORMING DIPEPTIDYL LINKER

(75) Inventors: Fernando Albericio, Barcelona (ES); Michèle Cristau, Visp (CH); Matthieu Giraud, Sion (CH); Miriam Gongora Benitez, Barcelona (ES); Judit Tulla-Puche, Palafrugell (ES)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 13/881,883

(22) PCT Filed: Oct. 20, 2011

(86) PCT No.: PCT/EP2011/005280
§ 371 (c)(1),
(2), (4) Date: Apr. 26, 2013

(87) PCT Pub. No.: WO2012/055509
PCT Pub. Date: May 3, 2012

(65) Prior Publication Data
US 2014/0094567 A1    Apr. 3, 2014

Related U.S. Application Data

(60) Provisional application No. 61/496,655, filed on Jun. 14, 2011.

(30) Foreign Application Priority Data

Oct. 29, 2010 (EP) .................................... 10014114
Dec. 8, 2010 (EP) .................................... 10015434
Dec. 8, 2010 (EP) .................................... 10015436
Feb. 22, 2011 (EP) .................................... 11001442
Jun. 14, 2011 (EP) .................................... 11004819

(51) Int. Cl.
*C07K 1/06* (2006.01)
*C07K 1/02* (2006.01)
*C07K 1/04* (2006.01)
*C07K 5/068* (2006.01)

(52) U.S. Cl.
CPC ................. *C07K 1/068* (2013.01); *C07K 1/062* (2013.01); *C07K 1/04* (2013.01); *C07K 5/06086* (2013.01)
USPC ............................ 530/335; 530/334; 530/339

(58) Field of Classification Search
None
See application file for complete search history.

(56) References Cited

U.S. PATENT DOCUMENTS 5,539,084 A * 7/1996 Geysen ......................... 530/334

FOREIGN PATENT DOCUMENTS

WO        WO 99/09395          8/1990

OTHER PUBLICATIONS

International Search Report for PCT/EP2011/005280 dated Jan. 18, 2012.
Bray, et al., "The simultaneous multiple production of solution phase peptides; Assessment of the Geysen Method of Simultaneous Peptide Synthesis" *Tetrahedron Letters*; Elsevier, Amsterdam, NL, vol. 31, No. 40, Sep. 24, 1990.
Frank et al., "Spot-Synthesis: an easy technique for the positionally addressable, parallel chemical synthesis on a membrane support", *Tetrahedron*, Elsevier Science Publishers, Amsterdam, NL, vol. 48, No. 42, Jan. 1, 1992.

* cited by examiner

*Primary Examiner* — Christina Bradley
(74) *Attorney, Agent, or Firm* — Dority & Manning, P.A.

(57) ABSTRACT

The invention relates to a method for homogeneous solution phase peptide synthesis (HSPPS) of a N-terminal peptide fragment PEP-N and a C-terminal peptide fragment C-PEP, with C-PEP carrying a specific diketopiperazine (DKP) comprising C-terminal protecting group, which contains a handle group HG, with HG being connected to the C-terminus of the peptide fragment; thereby this specific DKP comprising C-terminal protecting group can be selectively cleaved from the peptide as a conventionally used C-terminal protecting group. By the use of this DKP and HG comprising C-terminal protecting group, certain process steps in convergent peptide synthesis based on a combination of HSPPS and solid phase peptide synthesis (SPPS) can be avoided. The invention relates further to a method for the preparation of such specifically protected fragment C-PEP by SPPS by using a linker comprising a specific dipeptide and HG for connecting the growing peptide chain to the resin, which linker forms said DKP group, when the peptide fragment C-PEP is cleaved from the supporting resin; and further to the intermediates of the preparation method.

12 Claims, No Drawings

DIKETOPIPERAZINE FORMING DIPEPTIDYL LINKER

RELATED APPLICATION

This application is the national stage entry of International Patent Application No. PCT/EP2011/005280 having a filing date of Oct. 20, 2011, which claims filing benefit of European Patent Application EP10014114.2 having a filing date of Oct. 29, 2010; EP10015436.8 and EP10015434.3 both having a filing date of Dec. 8, 2010; EP11001442.0 having a filing date of Feb. 22, 2011; EP11004819.6 having a filing date of Jun. 14, 2011 and U.S. Provisional Application Ser. No. 61/496,655 having a filing date of Jun. 14, 2011, which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on May 13, 2013, is named LZA-8-PCT-US_S-L.txt and is 2,937 bytes in size.

The invention relates to a method for homogeneous solution phase peptide synthesis (HSPPS) of a N-terminal peptide fragment PEP-N and a C-terminal peptide fragment C-PEP, with C-PEP carrying a specific diketopiperazine (DKP) comprising C-terminal protecting group, which contains a handle group HG, with HG being connected to the C-terminus of the peptide fragment; thereby this specific DKP comprising C-terminal protecting group can be selectively cleaved from the peptide as a conventionally used C-terminal protecting group. By the use of this DKP and HG comprising C-terminal protecting group, certain process steps in convergent peptide synthesis based on a combination of HSPPS and solid phase peptide synthesis (SPPS) can be avoided.

The invention relates further to a method for the preparation of such specifically protected fragment C-PEP by SPPS by using a linker comprising a specific dipeptide and HG for connecting the growing peptide chain to the resin, which linker forms said DKP group, when the peptide fragment C-PEP is cleaved from the supporting resin; and further to the intermediates of the preparation method.

In this text, the nomenclature of amino acids and of peptides is used according to "Nomenclature and symbolism for amino acids and peptides", Pure & Appl. Chem., Vol. 56, No. 5, pp. 595-624, 1984, if not otherwise stated.

The following abbreviations have the meaning as given in the following list, if not otherwise stated:

| | |
|---|---|
| CTC | chlorotrityl chloride |
| Alloc | allyloxycarbonyl |
| Boc | tert-butoxycarbonyl |
| Bsmoc | 1,1-dioxobenzo[b]thiophen-2-ylmethyloxycarbonyl |
| Bzl or Bn | benzyl |
| cHx | cyclohexyl |
| Ct | C terminal |
| Dpr | 2,3-diaminopropanoic acid |
| Dde | N-1-(4,4-dimethyl-2,6-dioxocyclohexylidene)ethyl |
| ivDde | 1-(4,4-dimethyl-2,6-dioxocyclohexylidene)3-methylbutyl |
| Ddz | alpha,alpha-dimethyl-3,5-dimethoxybenzyloxycarbonyl |
| DKP | 2,5-diketopiperazine |
| Dmab | dimethylaminoborane |
| Fm | 9-Fluorenylmethyl |
| Fmoc | N-(fluorenyl-9-methoxycarbonyl) |
| Hpr | piperidine-2-carboxylic acid, homoproline |
| HSHSPPS | hybrid solid and homogenous solution phase peptide synthesis |
| HSPPS | homogenous solution phase peptide synthesis |
| Hyp | trans-4-hydroxyproline |
| Mmt | 4-methoxytrityl |
| Mpe | 3-methylpent-3-yl, |
| Mtt | 4-methyltrityl |
| Orn | ornithine |
| Pbf | 2,2,4,6,7-pentamethyldihydrobenzofuran-5-sulfonyl |
| PG | protecting group |
| 2-PhiPr | 2-phenylisopropyl |
| Pmc | 2,2,5,7,8-penta-methylchroman-6-sulfonyl |
| pNO$_2$Z | nitrobenzyloxycarbonyl |
| Py | Pyridine |
| SPPS | solid phase peptide synthesis |
| tBu | tert-butyl |
| TES | SiEt3, Triethylsilyl |
| TFA | Trifluoroacetic acid |
| Tfac | trifluoroacetyl |
| Trt or Tr | triphenylmethyl or trityl |
| Z | benzyloxycarbonyl |

The terms "fragment" and "peptide fragment" are used synonymously, if not otherwise stated. The terms "handle" and "handle group", e.g. "Fmoc-Rink amide handle group", "Rink amide handle" or "Rink amide handle group", and the term "linker", e.g. "Fmoc-Rink amide linker" or Fmoc-Rink-OH, are often used synonymously, if not stated otherwise.

Peptides are often prepared by hybrid solid and homogenous solution phase peptide synthesis HSHSPPS: firstly two or more peptide fragments are prepared by solid phase peptide synthesis SPPS, which are thereafter coupled in solution phase by homogenous solution phase peptide synthesis HSPPS to provide for the desired target peptide.

This approach is particularly attractive for the commercial scale preparation of large peptides as it combines the advantages of both the SPPS and the HSPPS. In particular, the SPPS of fragments can be developed and scaled-up rapidly and avoids many of the solubility problems often encountered in HSPPS of relatively long fragments. Production cycle times are short compared to solution phase methodologies. In addition, yields and purities are often higher because of the use of excess reagents, especially during the coupling reactions, which often results in intermediates that do not require purification. After optimization of selection of the sequences of the fragments made by SPPS, the final stages of the process can be scaled-up by conventional HSPPS methodologies. These final stages of the process are the fragment coupling and the final deprotection of the amino acid residues, i.e. the deprotection of the side chains and of the N- and C-terminus, both being performed in solution. Thus, when applying the HSHSPPS synthesis, the advantages of the SPPS, i.e. rapid synthesis of fragments with high purities, and the advantages of solution-phase synthesis, i.e. full monitoring of coupling reactions and isolation and optional purification including full characterization of the formed intermediate fragments, can be exploited in order to efficiently produce peptides, especially on commercial scale.

In HSHSPPS, always at least two fragments PEP-N and C-PEP prepared by SPPS are coupled in solution phase to provide the desired peptide PEP, which is either the final peptide or again an intermediate peptide fragment, which again thereafter is coupled with a third peptide fragment, and so on. Fragment PEP-N presents herein the N-terminus of peptide PEP, fragment C-PEP presents the C-terminus of peptide PEP, and therefore the C-terminus of fragment PEP-N is coupled with the N-terminus of fragment C-PEP to provide peptide PEP. It is necessary, that the N-terminus of fragment PEP-N is protected as well as the C-terminus of fragment C-PEP is protected during solution phase coupling in order to avoid undesired coupling of fragment PEP-N with fragment PEP-N, of fragment C-PEP with fragment C-PEP, or of fragment C-PEP with fragment PEP-N in the wrong direction. This N-terminally protected peptide fragment PEP-N is in the following also called PEP-N, if not otherwise stated. The fragment C-PEP, prepared by SPPS on a supporting resin, will carry an N-terminal protecting group after the addition of the last amino acid residue, and will then be cleaved from the supporting resin in a final step. This cleavage results usually in a fragment C-PEP with an unprotected C-terminus, which must be protected in a separate step, before fragment C-PEP can be coupled in HSPPS with fragment PEP-N. Actually, this necessary protection of the C-terminus of fragment C-PEP comprises not only one step, but several steps such as reaction, purification and isolation, possibly with another subsequent purification and isolation.

In case the target peptide PEP to be prepared is a peptide amide PEP-NH$_2$, i.e. with the C-terminus being a carboxamide group, the C-terminus of the respective fragment C-PEP-NH$_2$ normally does not need to be protected during fragment coupling in HSPPS, since the carboxamide group itself acts as a protecting group. While a fragment C-PEP-OH, with the C-terminus being the carboxylic acid, can be easily obtained after SPPS by use of a resin which forms the carboxylic acid group after cleavage, the use of a resin which forms the carboxamide group after cleavage, e.g. the Sieber amide resin, causes problems due to partial side chain deprotection of the fragment C-PEP-NH$_2$ during cleavage, since cleavage from amide resins typically requires acidic conditions, such as the use of 3 to 5% by weight of TFA in a solvent, and side chain protecting groups, such as Trt in case of Fmoc/Trt SPPS (for example His(Trt)) or such as acetale in pseudo-proline derivatives (i.e. Fmoc-Ser(tBu)-Thr(psi$^{Me,Me}$pro)-OH), are not completely stable under such cleavage conditions, which results in partial loss of the side chain protecting groups. Therefore for preparing fragment C-PEP-NH$_2$, it is common to start the SPPS with the amino acid second in position from the C-terminal amino acid residue of the desired fragment C-PEP-NH$_2$ and not with the C-terminal amino acid itself of fragment C-PEP-NH$_2$, and with a resin which affords a carboxylic acid as C-terminus after cleavage. Cleavage from the resin affords therefore a fragment C—OH without the C-terminal amino acid of the desired fragment C-PEP-NH$_2$, and with the C-terminus of this fragment C—OH being the amino acid of the second position from the C-terminus of the finally desired fragment C-PEP-NH$_2$ and bearing a carboxylic acid group. The missing C-terminal amino acid of fragment C-PEP-NH$_2$ is then separately coupled to the fragment C—OH in form of its amide H-Xaa-NH$_2$ in solution phase.

WO 90/09395 discloses the use of a cleavable linker between peptide and the supporting resin, which forms a diketopiperazine (DKP) linker group when cleaved from the resin, wherein the DKP group is connected to the peptide via an amide bond between the epsilon amino group of a Lys in the linker group and the C-terminus of the peptide. This DKP linker group cannot be removed selectively from the peptide at a later stage. Thus, it does not allow for the preparation of fully protected C-terminal fragments with unprotected N-terminus suitable in HSPPS. Furthermore, the linker group of WO 90/09395 does not allow for the preparation of natural or unmodified peptides. It is only suitable for the synthesis of permanently C-terminally modified peptides, since any peptide cleaved from the resin always carries a DKP linker group at its C-terminus, which is not cleavable without cleaving the other peptide bonds of the peptide. Another disadvantage is the restriction of its cleavage to the use of trifluoroacetic acid (TFA) during the cleavage step, which implies the partial or total removal of any tBu, Boc, Trt or Acetale based protecting groups of the side chains of the amino acid residues of the peptide, thereby restricting its use to the preparation of either peptides with unprotected side chains or to side chain protecting groups other than tBu, Boc, Trt and Acetale.

There was a need to simplify the procedure of HSHSPPS by reducing the number of steps in the reaction sequence.

Surprisingly, this can be achieved by using a specific diketopiperazine group forming dipeptidyl linker in the SPPS used to prepare the fragment C-PEP, which carries a specific diketopiperazine comprising C-terminal protecting group, together with an appropriate combination of the different types of protecting groups and a specific chemical nature of the connection of the linker to the fragment C-PEP providing specific cleavage possibility of the linker from the fragment.

Protecting groups (PG), be it for protecting functional groups in side chains of amino acid or for the protection of N-terminal amino groups or C-terminal carboxy groups of amino acids or peptides, are for the purpose of this invention classified into four different groups:
1. basic cleavable type protecting groups, in the following called "basic type PGs",
2. strong acid cleavable type protecting groups, in the following called "strong type PGs",
3. weak acid cleavable type protecting groups, in the following called "weak type PGs", and
4. reductively cleavable type protecting groups. in the following called "reductive type PGs", with the two groups "strong type PGs" and "weak type PGs" also collectively called "acid cleavable type protecting groups" or "acid type PGs".

Within the meaning of this invention, any PG is classified by the following four classification reaction conditions. The classification is done using a CTC resin with a loading capacity of 1.5 to 1.7 mmol per g resin, the resin being loaded with only one amino acid carrying the respective PG which is to be classified. The term "part" in the following four classification procedures is meant to be a factor of the parts by weight of the loaded CTC resin starting material, if not otherwise stated.
1. Classification Reaction Conditions for Basic Type PG, in the Following Text Called "Basic Classification Conditions":

Treatment for 25+/5 min at 25+/−5° C. of the resin loaded with the basic type PG carrying amino acid with 7+/−1 parts of a cleaving solution, the cleaving solution consisting of 22.5+/−2.5% by weight solution of piperidine in dimethylformamide (DMF), the % by weight being based on the total weight of the cleaving solution.
2. Classification Reaction Conditions for Strong Type PGs, in the Following Text Called "Strong Classification Conditions":

Treatment for 25+/5 min at 25+/−5° C. of the resin loaded with the strong type PG carrying amino acid with 7+/−1 parts of a cleaving solution, the cleaving solution consisting of 85+/−5% by weight solution of trifluoro acetic acid (TFA) in dichloromethane (DCM), the % by weight being based on the total weight of the cleaving solution.
3. Classification Reaction Conditions for Weak Type PGs, in the Following Text Called "Weak Classification Conditions":

Treatment for 25+/5 min at 25+/−5° C. of the resin loaded with the weak type PG carrying amino acid with 7+/−1 parts of a cleaving solution, the cleaving solution consisting of 2+/−1% by weight solution of TFA in DCM, the % by weight being based on the total weight of the cleaving solution.
4. Classification Reaction Conditions for Reductive Type PGs, in the Following Text Called "Reductive Classification Conditions":

Treatment for 30+/5 min at 25+/−5° C. of the resin loaded with the reductive type PG carrying amino acid with 7+/−1 parts of DMF, with 0.1 mol equivalent of a soluble organic Pd(0) catalyst, preferably Pd[PPh₃]₄, dissolved in the DMF, the mol equivalent being based on the mol of cleavable groups loaded on the resin.

PGs and typical reaction conditions and parameters and reagents for cleaving PGs, which are conventionally used in peptide chemistry, are known in the art, e.g. T. W. Greene, P. G. M. Wuts "Protective Groups in Organic Synthesis" John Wiley & Sons, Inc., 1999; or Lloyd-Williams, P., Albericio, F., Giralt, E., "Chemical Approaches to the Synthesis of Peptides and Proteins" CRC: Boca Raton, Fla., 1997.

Basic type PGs are preferably cleaved under following possible reaction conditions, in the following text called "basic cleaving conditions":

Basic cleaving conditions involve treatment of the respective material with a basic cleaving solution. The basic cleaving solution comprises a basic reagent and a solvent. Preferably, the basic cleaving solution consists of a basic reagent and a solvent. If the basic reagent is liquid at the temperature, at which the basic cleaving is done, the basic reagent can also act simultaneously as the solvent, i.e. no solvent different from the basic reagent is used.

Basic reagents are preferably secondary amines, more preferably the basic reagent is selected from the group consisting of piperidine, 4-(aminomethyl)piperidine, tris(2-aminoethyl)amine, morpholine, dicyclohexylamine, 1,3-cyclohexanebis(methylamine)piperazine, 1,8-diazabicyclo[5.4.0]undec-7-ene and mixtures thereof. Even more preferably, the basic reagent is piperidine.

The basic cleaving solution can also comprise an additive, the additive preferably selected from the group consisting of 6-chloro-1-hydroxy-benzotriazole, 2,4-dinitrophenol, picric acid, 1-hydroxy-7-azabenzotriazole, 1-hydroxy-benzotriazole and ethyl 2-cyano-2-hydroxyimino¬ acetate and mixtures thereof.

Preferably, the solvent is selected from the group consisting of dimethylsulfoxide (DMSO), dioxane, tetrahydrofuran (THF), 1-methyl-2-pyrrolidone (NMP), N,N-dimethylformamide (DMF), N,N-dimethylacetamide (DMA), pyridine, dichloromethane (DCM), dichloroethane (DCE), chloroform, dioxane, tetrahydropyran, ethyl acetate, toluene, acetonitrile and mixtures thereof; more preferably the solvent is 1-methyl-2-pyrrolidone (NMP), N,N-dimethylformamide (DMF) or a mixture thereof.

The term "part" in this description of basic cleaving conditions is meant to be a factor of the parts by weight of the treated material carrying the basic type PG(s).

Preferably, of from 5 to 20 parts, more preferably of from 5 to 15 parts of basic cleaving solution are used.

Preferably, the amount of basic reagent is of from 1 to 30% by weight, more preferably of from 10 to 25% by weight, even more preferably of from 15 to 20% by weight, with the % by weight being based on the total weight of the basic cleaving solution.

Preferably, basic cleaving is done at a temperature of from 10 to 50° C., more preferably of from 10 to 30° C., even more preferably of from 15 to 25° C.

Preferably, basic cleaving is done at atmospheric pressure.

Preferably, the reaction time for basic cleaving is of from 5 min to 2 h, more preferably of from 10 min to 1 h, even more preferably of from 15 min to 30 min.

Strong type PGs are preferably cleaved under the following possible reaction conditions, in the following text called "strong cleaving conditions":

Strong cleaving conditions involve treatment of the respective material with a strong cleaving solution. The strong cleaving solution comprises an acidolytic reagent. Acidolytic reagents are preferably selected from the group consisting of hydrogen acids, such as trifluoroacetic acid (TFA), hydrochloric acid (HCl), aqueous hydrochloric acid (HCl), liquid hydrofluoric acid (HF) or trifluoromethanesulfonic acid, Lewis acids, such as trifluoroborate diethyl ether adduct or trimethylsilylbromid, and mixtures thereof.

The strong cleaving solution preferably comprises one or more scavengers, the scavengers being selected from the group consisting of dithiothreitol (DTT), ethanedithiol (EDT), dimethylsulfide (DMS), triisopropylsilane (TIS), triethylsilane (TES), 1,3-dimethoxybenzene (DMB), phenol, anisole, p-cresol and mixtures thereof.

The strong cleaving solution can also comprise water, a solvent or a mixture thereof, the solvent being stable under strong cleaving conditions.

Preferably, solvents are selected from the group consisting of dichloromethane, dichloroethane, acetonitrile, toluene, tetrahydrofurane, TFA, dioxane and mixtures thereof.

More preferably, the acidolytic reagent acts simultaneously as solvent, so no further solvent is needed.

The term "part" in this description of strong cleaving solution is meant to be a factor of the parts by weight of the treated material carrying the strong type PG(s).

Preferably, of from 10 to 30 parts, more preferably of from 15 to 25 parts, even more preferably of from 19 to 21 parts of strong cleaving solution are used.

Preferably, the amount of acidolytic reagent is of from 30 to 100% by weight, more preferably of from 50 to 100% by weight, even more preferably of from 70 to 100% by weight, especially of from 80 to 100% by weight, with the % by weight being based on the total weight of the strong cleaving solution.

Preferably, of from 1 to 25% by weight of total amount of scavenger is used, more preferably of from 5 to 15% by weight, with the % by weight based on the total weight of the strong cleaving solution.

Preferably, strong cleaving is done at a temperature of from −10 to 30° C., more preferably of from −10 to 30° C., even more preferably of from 5 to 15° C.

Preferably, strong cleaving is done at atmospheric pressure.

Preferably, the reaction time for strong cleaving is of from 30 min to 20 h, more preferably of from 1 h to 10 h, even more preferably of from 1 h to 5 h.

Weak type PGs are preferably cleaved under the following possible reaction conditions, in the following text called "weak cleaving conditions":

Weak cleaving conditions involve treatment of the respective material with a weak cleaving solution. The weak cleaving solution comprises an acidolytic reagent. The acidolytic reagent is preferably selected from the group consisting of hydrogen acids, such as trifluoroacetic acid (TFA), trifluoroethanol (TFE), hydrochloric acid (HCl), acetic acid (AcOH), mixtures thereof and/or with water.

The weak cleaving solution also comprises water, a solvent or a mixture thereof, the solvent being stable under weak cleaving conditions.

Preferably, solvents are selected from the group consisting of dichloromethane, dichloroethane, acetonitrile, toluene, tetrahydrofurane, TFA, dioxane and mixtures thereof.

The term "part" in this description of weak cleaving solution is meant to be a factor of the parts by weight of the treated material carrying the weak type PG(s).

Preferably, of from 4 to 20 parts, more preferably of from 5 to 10 parts, of weak cleaving solution are used.

Preferably, the amount of acidolytic reagent is of from 0.01 to 5% by weight, more preferably of from 0.1 to 5% by weight, even more preferably of from 0.15 to 3% by weight, with the % by weight being based on the total weight of the weak cleaving solution.

Preferably, weak cleaving is done at a temperature of from 10 to 50° C., more preferably of from 20 to 40° C., even more preferably of from 25 to 35° C.

Preferably, weak cleaving is done at atmospheric pressure.

Preferably, the reaction time for weak cleaving is of from 5 min to 2 h, more preferably of from 10 min to 1 h, even more preferably of from 10 min to 30 min.

The weak type PG can be subclassified into further groups, these groups being differentiated from one another and can be aligned consecutively according to the amount of acid necessary for cleavage. According to above definition of weak classification conditions, all weak type PGs can be cleaved using 2+/−1% by weight solution of TFA in DCM, the % by weight being based on the total weight of the cleaving solution. A weak type PG, which is only cleaved by a solution of at least 1% by weight of TFA in DCM, but not by a solution with less amount of TFA, is called "weak 1 type PG" and the cleaving conditions are called "weak 1 cleaving conditions"; a weak type PG, which is cleaved already by a solution of at least 0.1% by weight of TFA in DCM, but not by a solution with less amount of TFA, is called "weak 2 type PG" and the cleaving conditions are called "weak 2 conditions"; a weak type PG, which is cleaved already by a solution of at least 0.01% by weight of TFA in DCM, is called "weak 3 type PG" and the cleaving conditions are called "weak 3 conditions"; the % by weight being based on the total weight of the cleaving solution.

Reductive type PGs are preferably cleaved under the following possible reaction conditions, in the following text called "reductive cleaving conditions":

Reductive cleaving conditions involve treatment of the respective material with a reductive cleaving solution. The reductive cleaving solution comprises a catalyst, an additive and a solvent.

The catalysts are preferably selected from the group consisting of organic derivatives of Pd(0) and organic derivates of Pd(II),
more preferably selected from the group consisting of Pd[PPh$_3$]$_4$, PdCl$_2$[PPh$_3$]$_2$, Pd[OAc]$_2$[P(2,4-xyloyl)$_3$]$_2$, Pd[OAc]$_2$[P(ortho-tolyl)$_3$]$_2$,
in situ prepared Pd(0) catalysts, prepared by mixing less stably coordinated Pd-complexes with ligands, such as PdCl$_2$(PPh$_3$)$_2$/PPh$_3$, PdCl$_2$(PPh$_3$)$_2$/P(ortho-tolyl)$_3$, Pd(DBA)$_2$/P(ortho-tolyl)$_3$ or Pd[P(ortho-tolyl)$_3$]$_2$, Pd(OAc)/triethyl-phosphite, Pd(OAc)$_2$/PPh$_3$ or Pd(OAc)$_2$/P(ortho-tolyl)$_3$,
and mixtures thereof;
even more preferably selected from the group consisting of Pd[PPh$_3$]$_4$, PdCl$_2$[PPh$_3$]$_2$, Pd[OAc]$_2$[P(2,4-xyloyl)$_3$]$_2$, Pd[OAc]$_2$[P(ortho-tolyl)$_3$]$_2$ and mixtures thereof.

The additive is preferably selected from the group consisting of dimethylbarbituric acid, thiosalicylic acid, N-methylaniline, Bu$_4$N$^+$BH$_4^-$, NH$_3$BH$_3$, Me$_2$NHBH$_3$, tBu-NH$_2$BH$_3$, Me$_3$NBH$_3$, PyBH$_3$, HCOOH/DIEA, diethydithiocarbamate sodium, dimedone, morpholine, AcOH/NMM, phenylsilane, sulfinic acids comprising PhSO$_2$H, tolSO$_2$Na, sodium 2-ethylhexanoate (SEH), sodium 2-thiophenesulfinate (STS), sodium 4-chloro-3-nitrobenzenesulfinate (SCNBS) and i-BuSO$_2$Na, and mixtures thereof; more preferably the additive is tolSO$_2$Na.

Preferably, the solvent is selected from the group consisting of dimethylsulfoxide (DMSO), dioxane, tetrahydrofuran (THF), 1-methyl-2-pyrrolidone (NMP), N,N-dimethylformamide (DMF), N,N-dimethylacetamide (DMA), pyridine, dichloromethane (DCM), dichloroethane (DCE), chloroform, dioxane, tetrahydropyran, ethyl acetate, toluene, acetonitrile and mixtures thereof; more preferably the solvent is 1-methyl-2-pyrrolidone (NMP), N,N-dimethylformamide (DMF) or a mixture thereof.

Preferably, the catalyst is dissolvable in the solvent and is dissolved in the solvent.

The term "part" in this description of reductive cleaving conditions is meant to be a factor of the parts by weight of the treated material carrying the reductive type PG(s).

Preferably, of from 4 to 20 parts, more preferably of from 5 to 10 parts, of reductive cleaving solution are used.

Preferably, 0.001 to 1 mol equivalents, more preferably 0.01 to 0.05 mol equivalents, of catalyst are used, the mol equivalent being based on the mol of reductively cleavable groups loaded on the resin.

Preferably, 1 to 10 mol equivalents, more preferably 1.5 to 5 mol equivalents, of additive are used, the mol equivalent being based on the mol of reductively cleavable groups loaded on the resin.

Preferably, reductive cleaving is done at a temperature of from 10 to 60° C., more preferably of from 30 to 50° C., even more preferably of from 35 to 45° C.

Preferably, reductive cleaving is done at atmospheric pressure.

Preferably, the reaction time for reductive cleaving is of from 15 min to 10 h, more preferably of from 30 min to 4 h, even more preferably of from 30 min to 2 h.

Preferably, the reductive cleaving solution has to be protected form the light. Preferably, reductive cleaving is done in a container made of metal.

The basic type PGs are not cleavable by strong or weak cleaving conditions.

Preferably, the basic type PGs are not cleavable by strong, weak or reductive cleaving conditions.

The strong type PGs are not cleavable by weak or basic cleaving conditions.

Preferably, the strong type PGs are not cleavable by weak, basic or reductive cleaving conditions.

The weak type PGs are not cleavable by basic cleaving conditions, but they are cleavable by strong cleaving conditions.

Preferably, the weak type PGs are not cleavable by basic or reductive cleaving conditions, but they are cleavable by strong cleaving conditions.

The weak 1 type PGs are not cleavable by weak 2 or weak 3 cleaving conditions;
the weak 2 type PGs are cleavable by weak 1 cleaving conditions, but not by weak 3 cleaving conditions;
the weak 3 type PG are cleavable by weak 1 and by weak 2 cleaving conditions.
preferably, the weak 1, 2 and 3 type PGs are also not cleavable by basic or reductive cleaving conditions.

Preferably, reductive type PGs are not cleavable by strong, weak and basic cleaving conditions, these are called "exclusively reductive type PGs".

Reductive type PGs, which are not cleavable by weak and basic cleaving conditions, but which are cleavable by strong cleaving conditions; these PGs are called "mixed type PGs".

The connection of the linker to the peptide can also be classified to be cleavable under one of these four cleaving conditions.

The connection of an amino acid to a resin can also be classified to be cleavable under one of these four cleaving conditions.

Preferably, a basic type PG is selected from the group consisting of Fmoc, Bsmoc, Tfac, Dde, Dmab and cHx.
Preferably, a strong type PG is selected from the group consisting of Boc, tBu, Pmc, Mpe, Pbf, Z, Bzl, cHx, $pNO_2Z$ and Ddz.
Preferably, a weak type PG is selected from the group consisting of Trt, Mmt, Mtt, acetale and 2-PhiPr.
If a weak type PG is actually a weak 1 type PG or a weak 2 type PG, depends on the side chain group which it protects.
Preferably, a reductive type PG is selected from the group consisting of Alloc, Allyl, ivDde and Z.
More preferably, a basic type PG is Fmoc.
More preferably, a strong type PG is Boc.
More preferably, a weak type PG is Trt.
More preferably, a reductive type PG is Alloc.

In conventional SPPS, the peptide is cleaved from the resin after the SPPS is finished, the cleavage resulting in a peptide with a C-terminus in form of a free carboxylic acid group or in form of a carboxamide, depending on the resin and a possible handle used in SPPS. If this peptide with a free carboxylic group at its C-terminus is to be used in HSPPS as the C-terminal peptide fragment C-PEP, this free carboxylic acid group has firstly to be protected, before the peptide can be used in HSPPS. This protection of the free C-terminus needs several process steps (reaction, isolation, perhaps purification).

The instant invention discloses a method for reducing these steps necessary for protecting a free carboxylic acid at the C-terminus of the fragment resulting from cleavage of the fragment from the resin after SPPS. This is achieved by using said diketopiperazine forming dipeptidyl linker to couple in the SPPS the first amino acid $XaaC^{(1)}$ of the desired fragment C-PEP via said linker onto the resin support, which linker forms a diketopiperazine residue comprising C-terminal protecting group, when the SPPS is finished and the synthesized fragment C-PEP is being cleaved from the resin. The diketopiperazine forming dipeptidyl linker comprises a dipeptide moiety, whose first amino acid Xaa1 is via its carboxylic acid group connected to the resin, and whose second amino acid Xaa2 is via its side chain connected a handle group HG, which handle group HG is connected to the peptidyl radical, and Xaa 7 carries an N-terminal protecting group PG2.

The formation of said diketopiperazine residue comprising C-terminal protecting group is achieved by cleaving the protecting group PG2 of Xaa2, thereby making an intramolecular ring closure between Xaa2 and Xaa1 possible, which ring closure forms said diketopiperazine residue and simultaneously cleaves Xaa1 from the resin.

This diketopiperazine residue comprising C-terminal protecting group, formed by the cleavage from the resin, remains connected to the C-terminus of the fragment C-PEP after cleavage from the resin and acts thereby as a protecting group of the C-terminus of the fragment C-PEP, which can therefore directly be used in HSPPS. After coupling of this C-terminal fragment C-PEP with an N-terminal peptide fragment PEP-N by HSPPS to yield the peptide PEP, the diketopiperazine residue comprising C-terminal protecting group is cleaved from the peptide PEP, preferably simultaneously with the deprotection of any protected side chain in fragment PEP.

The diketopiperazine forming dipeptidyl linker and the resulting diketopiperazine residue comprising C-terminal protecting group comprise the handle group HG, which makes the cleavage of the peptide PEP from the diketopiperazine residue comprising C-terminal protecting group possible.

To make this desired function possible, said diketopiperazine forming dipeptidyl linker is constructed in such a way, that the four principal cleavage steps
1. the cleavage of each N-terminal protecting group of the amino acids during the cycles of SPPS,
2. the cleavage of the fragment C-PEP from the resin by cleaving the protecting group PG2 from Xaa2, and then cleaving Xaa1 from the resin by forming the diketopiperazine residue comprising C-terminal protecting group, and
3. the cleavage of the diketopiperazine residue comprising C-terminal protecting group from the peptide PEP, which is the cleavage of the peptide from HG in the diketopiperazine residue comprising C-terminal protecting group;
4. cleavage of any side chain PG;

can be done under different reaction conditions, therefore each cleavage can be done separately and independently from the other cleavage at the appropriate point of time in the reaction sequence.

To achieve this function, the chemical nature of the various PGs involved in the reaction strategy and the chemical nature of the connection of the handle group HG of the linker to the peptide is chosen in such a way, that any PG belongs to one of the four types of PGs in such a way, and that the connection of the handle group HG to the peptide is cleavable under such reaction conditions, that this grouping of the protecting groups and this selection of the nature of the connection of the handle group HG to the peptide allow for the desired and necessary separate and stepwise cleavage.

If there are one or more side chain PGs in the desired peptide C-PEP, one preferred embodiment is, that
1. any side chain protecting group is a strong, reductive or mixed type PG; and
2. any N-terminal PG of the amino acids used in SPPS in the synthesis of C-PEP except for the last one, i.e. except for the N-terminal PG of the N-terminal amino acid of the peptide C-PEP, is a basic type PG, or
   any N-terminal PG of the amino acids used in SPPS in the synthesis of C-PEP except for the last one, i.e. except for the N-terminal PG of the N-terminal amino acid of the peptide C-PEP, is a basic, a reductive or a mixed type PG, if any side chain protecting group is not a reductive or mixed type PG; and
3. PG2 is a weak, a reductive or a mixed type PG, if any side chain protecting group and any N-terminal PG of the amino acids used in SPPS in the synthesis of C-PEP except for the last one, i.e. except for the N-terminal PG of the N-terminal amino acid of the peptide C-PEP, is not a reductive or mixed type PG, or
   PG2 is a weak type PG; and
4. the N-terminal PG of the last amino acid used in SPPS in the synthesis of C-PEP, i.e. of the N-terminal amino acid of the peptide C-PEP, is a basic or a weak type PG, or
   the N-terminal PG of the last amino acid used in SPPS in the synthesis of C-PEP, i.e. of the N-terminal amino acid of the peptide C-PEP, is a basic, a weak, a reductive or a mixed type PG, if any side chain protecting group is not a reductive or mixed type PG; and
5. the diketopiperazine residue comprising C-terminal protecting group of PEP or C-PEP is cleavable from the peptide PEP or C-PEP
   in strong cleaving conditions, or
   in strong or reductive cleaving conditions, if PG2 and any N-terminal PG of the amino acids used in SPPS in the synthesis of C-PEP are not reductive or mixed type PGs, or in weak cleaving conditions, if PG2 and any N-terminal PG of the amino acids used in SPPS in the synthesis of C-PEP are not weak type PGs, or in weak 1 cleaving conditions, if PG2 and any N-terminal PG of the amino acids used in SPPS in the synthesis of C-PEP are not weak 1 type PG.

If there are one or more side chain PGs in the desired peptide C-PEP, one more preferred embodiment is, that 1. any side chain protecting group is a strong type PG; and
2. any N-terminal PG of the amino acids used in SPPS in the synthesis of C-PEP except for the last one, i.e. except for the N-terminal PG of the N-terminal amino acid of the peptide C-PEP, is a basic type PG; and
3. PG2 is a weak, a reductive or a mixed type PG, if any side chain protecting group and any N-terminal PG of the amino acids used in SPPS in the synthesis of C-PEP except for the last one, i.e. except for the N-terminal PG of the N-terminal amino acid of the peptide C-PEP, is not a reductive or mixed type PG; and
4. the N-terminal PG of the last amino acid used in SPPS in the synthesis of C-PEP, i.e. of the N-terminal amino acid of the peptide C-PEP, is a basic, a weak, a reductive or a mixed type PG, if any side chain protecting group is not a reductive or mixed type PG; and
5. the diketopiperazine residue comprising C-terminal protecting group of PEP or C-PEP is cleavable from the peptide PEP or C-PEP in strong cleaving conditions, or in strong or reductive cleaving conditions, if PG2 and any N-terminal PG of the amino acids used in SPPS in the synthesis of C-PEP are not reductive or mixed type PGs, or in weak cleaving conditions, if PG2 and any N-terminal PG of the amino acids used in SPPS in the synthesis of C-PEP are not weak type PGs, or in weak 1 cleaving conditions, if PG2 and any N-terminal PG of the amino acids used in SPPS in the synthesis of C-PEP are not weak 1 type PG.

If there are one or more side chain PGs in the desired peptide C-PEP, another more preferred embodiment is, that 1. any side chain protecting group is a strong, reductive or mixed type PG; and
2. any N-terminal PG of the amino acids used in SPPS in the synthesis of C-PEP except for the last one, i.e. except for the N-terminal PG of the N-terminal amino acid of the peptide C-PEP, is a basic type PG; and
3. PG2 is a weak type PG; and
4. the N-terminal PG of the last amino acid used in SPPS in the synthesis of C-PEP, i.e. of the N-terminal amino acid of the peptide C-PEP, is a basic or a weak type PG; and
5. the diketopiperazine residue comprising C-terminal protecting group of PEP or C-PEP is cleavable from the peptide PEP or C-PEP in strong or reductive cleaving conditions, if PG2 and any N-terminal PG of the amino acids used in SPPS in the synthesis of C-PEP are not reductive or mixed type PGs, or in weak 1 cleaving conditions, if PG2 and any N-terminal PG of the amino acids used in SPPS in the synthesis of C-PEP are not weak 1 type PG.

If there are no side chain PGs in the desired peptide C-PEP, one preferred embodiment is, that 1. any N-terminal PG of the amino acids used in SPPS in the synthesis of C-PEP except for any N-terminal PG of the amino acids used in SPPS in the synthesis of C-PEP except for the last one, i.e. except for the N-terminal PG of the N-terminal amino acid of the peptide C-PEP, is a basic, a reductive or a mixed type PG; and
2. PG2 is a strong, weak, a reductive or a mixed type PG, if any N-terminal PG of the amino acids used in SPPS in the synthesis of C-PEP except for the last one, i.e. except for the N-terminal PG of the N-terminal amino acid of the peptide C-PEP, is not a reductive or mixed type PG, or PG2 is a strong, a weak or a mixed type PG; and 3. the N-terminal PG of the last amino acid used in SPPS in the synthesis of C-PEP, i.e. of the N-terminal amino acid of the peptide C-PEP, is a basic, a strong, a weak, a reductive or a mixed type PG; and
4. the diketopiperazine residue comprising C-terminal protecting group of PEP or C-PEP is cleavable from the peptide PEP or C-PEP in strong cleaving conditions, if PG2 and any N-terminal PG of the amino acids used in SPPS in the synthesis of C-PEP are not strong type PGs, or in strong or reductive cleaving conditions, if PG2 and any N-terminal PG of the amino acids used in SPPS in the synthesis of C-PEP are not strong, reductive and mixed type PGs, or in weak cleaving conditions, if PG2 and any N-terminal PG of the amino acids used in SPPS in the synthesis of C-PEP are not strong or weak type PGs, or in weak 1 cleaving conditions, if PG2 and any N-terminal PG of the amino acids used in SPPS in the synthesis of C-PEP are not strong or weak 1 type PGs.

If there are no side chain PG in the desired peptide C-PEP, one more preferred embodiment is, that 1. any N-terminal PG of the amino acids used in SPPS in the synthesis of C-PEP except for any N-terminal PG of the amino acids used in SPPS in the synthesis of C-PEP except for the last one, i.e. except for the N-terminal PG of the N-terminal amino acid of the peptide C-PEP, is a basic type PG; and
2. PG2 is a strong, weak, a reductive or a mixed type PG, or
3. the N-terminal PG of the last amino acid used in SPPS in the synthesis of C-PEP, i.e. of the N-terminal amino acid of the peptide C-PEP, is a basic, a strong, a weak, a reductive or a mixed type PG; and
4. the diketopiperazine residue comprising C-terminal protecting group of PEP or C-PEP is cleavable from the peptide PEP or C-PEP in strong cleaving conditions, if PG2 and any N-terminal PG of the amino acids used in SPPS in the synthesis of C-PEP are not strong type PGs, or in strong or reductive cleaving conditions, if PG2 and any N-terminal PG of the amino acids used in SPPS in the synthesis of C-PEP are not strong, reductive and mixed type PGs, or in weak cleaving conditions, if PG2 and any N-terminal PG of the amino acids used in SPPS in the synthesis of C-PEP are not strong or weak type PGs, or in weak 1 cleaving conditions, if PG2 and any N-terminal PG of the amino acids used in SPPS in the synthesis of C-PEP are not strong or weak 1 type PGs.

Subject of the invention is a method(C-PEP) for the preparation of a peptide C-PEP, C-PEP comprises a peptidyl radical PEP-C, the C-terminus of PEP-C is protected by a protecting group DKP-PG, DKP-PG comprises a handle group HG, optionally a spacer group SG, and a diketopiperazine residue DKP;

SG is a spacer group conventionally used in peptide chemistry;

DKP is a diketopiperazine residue derived from a dipeptide residue DPR;
DPR comprises alpha amino acid residues Xaa1 and Xaa2;
Xaa1 is the C-terminal amino acid residue of DPR;
Xaa2 is the N-terminal amino acid residue of DPR, and Xaa2 has a side chain, said side chain is substituted by a functional group FG;
PEP-C is connected via $XaaC^{(1)}$ to HG;
XaaC is an amino acid residue of PEP-C;
index (1) in $XaaC^{(1)}$ denotes the C-terminal position of PEP-C;
$XaaC^{(1)}$ is the C-terminal amino acid residue of PEP-C;
HG is a handle group conventionally used in solid phase peptide synthesis SPPS for connecting the C-terminus of a peptide to the solid phase, which allows for cleavage of the C-terminus from HG under conditions, which do not cleave an amide bond connecting two amino acid residues in a peptide;
HG is either directly connected to FG, or, if a SG is present, HG is connected to SG and SG is connected to FG;
method(C-PEP) comprises a step (iii);
step (iii) comprises a reaction(INRIFO);
reaction(INRIFO) is a reaction which comprises an intramolecular ring formation and a simultaneous cleavage reaction in a peptide PEP-C-DKP-L-ResinA;
PEP-C-DKP-L-ResinA is the precursor of C-PEP and comprises PEP-C and a resin DKP-L-ResinA, with PEP-C being connected to DKP-L-ResinA;
DKP-L-ResinA comprises a ResinA and a DKP-PG forming linker DKP-L, with ResinA being connected to DKP-L,
ResinA is a resin used conventionally as solid phase in SPPS,
DKP-L comprises HG, optionally SG, and DPR, with the C-terminal carboxylic acid group of DPR, which is the carboxylic acid group of Xaa1, being connected to ResinA;
the intramolecular ring formation in reaction(INRIFO) is a reaction of the N-terminal amino group of DPR, which is the alpha amino group of Xaa2, with the C-terminal carboxylic acid group of DPR, thereby forming DKP, thereby Xaa1 is simultaneously cleaved from ResinA and DKP-PG is formed;
HG is chosen in such a way, that the bond between HG and $XaaC^{(1)}$ is not cleaved during reaction(INRIFO).
By the use of HG, a cleaving site between $XaaC^{(1)}$ and ResinA is provided which can be selectively cleaved without cleaving any amide bond between two amino acids in the peptide; the cleaving site being the bond between $XaaC^{(1)}$ and HG. By this cleavage, the C-terminus of $XaaC^{(1)}$ is set free, either in form of a unprotected, free carboxylic acid group, or the C-terminal carboxylic acid group is set free in form of an amide group, preferably as $C(O)NH_2$, depending on the chemical nature of HG.
By the use of HG, this specific DKP comprising C-terminal protecting group acts as a conventionally in peptide chemistry used C-terminal protecting group.
Preferably, PEP-C is prepared prior to the reaction (INRIFO) by a solid phase peptide synthesis SPPS(PEP-C), more preferably the SPPS(PEP-C) uses DKP-L-ResinA as solid phase.
Therefore further subject of the invention is the method(C-PEP), with the method(C-PEP) as defined above, also with all its preferred embodiments, wherein PEP-C is prepared prior to step (iii) by a solid phase peptides synthesis SPPS(PEP-C), more preferably the SPPS(PEP-C) uses DKP-L-ResinA as solid phase. In SPPS(PEP-C), PEP-C is built by coupling the XaaC consecutively, first to the solid phase, then to the growing peptide chain. The various XaaC can be coupled individually and sequentially, but two or more of them can also be coupled e.g. as dipeptides, tripeptides or oligopeptides to the solid phase or to the growing peptide chain.
ResinA is chosen in such a way, that the bond between ResinA and Xaa1 is not cleaved during SPPS(PEP-C).
Preferably, SPPS(PEP-C) comprises further a step (i) and a step (ii);
in step (i) $XaaC^{(1)}$ is attached to DKP-L-ResinA;
in step (ii) the further amino acids XaaC according to the sequence of PEP-C are consecutively connected by SPPS(PEP-C) initially to $XaaC^{(1)}$ and then to the N-terminus of the growing peptidyl chain, which is bound via DKP-L to the ResinA;
HG is chosen in such a way, that the bond between HG and $XaaC^{(1)}$ is not cleaved during SPPS(PEP-C); and
that the bond between HG and $XaaC^{(1)}$ is not cleaved during reaction(INRIFO);
with C-PEP, ResinA, DKP-PG, HG, SG, DPR, DKP, Xaa1, $XaaC^{(1)}$, XaaC, PEP-C, SC-PG, reaction(INRIFO) as defined above, also with all their preferred embodiments;
and with the connectivities between PEP-C, HG, SG and DPR and ResinA as defined above, also with all their preferred embodiments.
Prior to reaction(INRIFO), the N-terminus of DPR, which is alpha amino group of Xaa2, is protected by a protecting group PG2.
Therefore further subject of the invention is a method(C-PEP), with the method(C-PEP) as defined above, also with all its preferred embodiments, wherein step (iii) comprises cleavage of the protecting group PG2;
PG2 is an N-terminal protecting group conventionally used in peptide chemistry and is selected from the group consisting of basic cleavable type protecting groups, acid cleavable type protecting groups and reductively cleavable type protecting groups.
PG2 is cleaved from Xaa2 before the reaction(INRIFO) in step (iii).
Preferably, PG2 is cleaved from Xaa2 after SPPS(PEP-C).
Preferably, PG2 is cleaved from Xaa2 after the addition of the N-terminal amino acid residue of PEP-C in step (ii).
The cleavage of PG2 from Xaa2 and the reaction(INRIFO) can occur consecutively or simultaneously.
PG2 is chosen in such a way, that the bond between PG2 and Xaa2 is not cleaved during SPPS(PEP-C).
PG2 and HG are chosen in such a way, that the bond between HG and $XaaC^{(1)}$ is not cleaved during the cleavage of PG2 from Xaa2.
Any side chain of C-PEP or PEP-C can be protected independently from any other side chain of C-PEP or PEP-C by a protecting group SC-PG, in case of more than one SC-PG being present in C-PEP or PEP-C, these SC-PG are independently from each other identical or different. Any SC-PG is a protecting group which is conventionally used in peptide chemistry for protecting side chains of amino acid residues of a peptide or for protecting side chains of amino acids during SPPS or during HSPPS.
Preferably, any SC-PG is chosen in such a way, that no SC-PG is cleaved during SPPS(PEP-C).
Preferably, any SC-PG is chosen in such a way, that no SC-PG is cleaved during reaction(INRIFO).
Preferably, PG2 and any protecting group SC-PG are chosen in such a way, that no SC-PG is cleaved during the cleavage of PG2 from Xaa2.
In order to avoid complexity of the description, the abbreviation XaaC is used either for the amino acids used to synthesis PEP-C and C-PEP, or it is used for the amino acid residues of PEP-C and C-PEP, or PEP-N respectively; and likewise XaaN is used either for the amino acids used to synthesis PEP-N, or it is used for the amino acid residues of PEP-N.

Therefore these abbreviations do not differentiate between amino acids and amino acid residues. The skilled person can unambiguously distinguish from the context, whether an amino acid or an amino acid residue is meant.

To summarize the connectivities:

PEP-C is connected via XaaC$^{(1)}$ to HG.

HG is either directly connected via FG to Xaa2, or, if a SG is present, HG is connected to SG and SG is connected via FG to Xaa2.

Xaa2 is connected with Xaa1 via a peptide bond, Xaa2 is the N-terminal and Xaa1 the C-terminal amino acid in DPR.

In PEP-C-DKP-L-ResinA, the carboxylic acid group of Xaa1 is connected to ResinA.

ResinA is chosen in such a way, that the bond between ResinA and Xaa1 is not cleaved during SPPS (PEP-C).

HG is chosen in such a way, that the bond between HG and XaaC$^{(1)}$ is not cleaved during reaction(INRIFO).

HG is chosen in such a way, that the bond between HG and XaaC$^{(1)}$ is not cleaved during SPPS(PEP-C).

PG2 is chosen in such a way, that the bond between PG2 and Xaa2 is not cleaved during SPPS(PEP-C).

PG2 and HG are chosen in such a way, that the bond between HG and XaaC$^{(1)}$ is not cleaved during the cleavage of PG2 from Xaa2.

Preferably, any SC-PG is chosen in such a way, that no SC-PG is cleaved during SPPS(PEP-C).

Preferably, any SC-PG is chosen in such a way, that no SC-PG is cleaved during reaction(INRIFO).

Preferably, PG2 and any protecting group SC-PG are chosen in such a way, that no SC-PG is cleaved during the cleavage of PG2 from Xaa2.

Preferably, C-PEP is PEP-C, whose C-terminus is protected by DKP-PG.

Preferably, DPR consists of the amino acid residues Xaa1 and Xaa2.

Xaa1 and Xaa2 are chosen in such a way, that they allow the formation of DKP by reaction(INRIFO).

Preferably, any side chain of C-PEP is protected by a protecting group SC-PG

If any SC-PG is present in C-PEP, then preferably HG is chosen in such a way, that HG, and thereby DKP-PG, is cleaved from XaaC$^{(1)}$ simultaneously in the reaction which cleaves SC-PG, preferably all SC-PGs.

Preferably, SC-PG is selected from the group consisting of basic cleavable type protecting groups, acid cleavable type protecting groups and reductively cleavable type protecting groups.

More preferably, any SC-PG is a strong type PG.

Preferably, FG, when connected to HG or to SG, is present as a connecting group CG.

Preferably, FG is selected from the group consisting of COOH, NH$_2$, OH and SH, more preferably consisting of NH$_2$ and OH; therefore CG is preferably selected from the group consisting of —C(O)O—, —N(H)—, —O— and —S—, more preferably consisting of —N(H)— and —O—.

The bond between HG and FG, or, if a SG is present in DKP-PG, the bonds between HG and SG and between SG and FG, are chosen to be of such a chemical nature, that they are not cleaved during SPPS (PEP-C);
and that they are not cleaved during reaction(INRIFO), step (i), step (ii) or step (iii); preferably, they are also not cleaved during any cleavage of any protecting group. Preferably, the bond between HG and FG, or, if a SG is present in DKP-PG, the bonds between HG and SG and between SG and FG, are amide or ester bonds, more preferably amide bonds. Especially, these bonds are of similar nature or stability as a conventional amide bond between two amino acid residues in a peptide.

The N-terminus of C-PEP can be protected by a protecting group N-PG, N-PG is an N-terminal protecting group conventionally used in peptide chemistry.

Preferably, N-PG is selected from the group consisting of basic cleavable type protecting groups, acid cleavable type protecting groups and reductively cleavable type protecting groups.

Therefore, C-PEP comprises both the N-terminally unprotected embodiment and the embodiment, wherein the N-terminus of PEP-C is protected by N-PG.

Further subject of the invention is a method(C-PEP) for the preparation of C-PEP, characterized by the steps (i), (ii) and (iii), which steps comprise a solid phase peptides synthesis SPPS(PEP-C) and a subsequent reaction(INRIFO);

the SPPS(PEP-C) is done on a resin DKP-L-ResinA as solid support, the DKP-L-ResinA is a ResinA, which carries as a functional group a DKP-PG forming linker DKP-L, DKP-L comprises HG, optionally SG, and DPR, with the Xaa1 of the DPR being connected via its C-terminal carboxylic acid group to ResinA, reaction(INRIFO) is a intramolecular ring formation reaction of the N-terminal amino group of DPR with the C-terminal carboxylic acid group of DPR, thereby forming DKP;

and by reaction(INRIFO) Xaa1 is simultaneously cleaved from ResinA and DKP-PG is formed;

in step (i) XaaC$^{(1)}$ is attached to DKP-L-ResinA;

in step (ii) the further amino acids XaaC according to the sequence of PEP-C are consecutively connected by SPPS (PEP-C) initially to XaaC$^{(1)}$ and then to the N-terminus of the growing peptide chain, which is bound via DKP-L to the ResinA;

in step (iii), which is done after the addition of the N-terminal amino acid residue of PEP-C in step (ii), C-PEP is formed by reaction(INRIFO), ResinA is chosen in such a way, that the bond between ResinA and Xaa1 is not cleaved during SPPS(PEP-C);

HG is chosen in such a way, that the bond between HG and XaaC$^{(1)}$ is not cleaved during SPPS(PEP-C); and that the bond between HG and XaaC$^{(1)}$ is not cleaved during reaction(INRIFO);

any SC-PG protecting a side chain of C-PEP is chosen in such a way, that SC-PG is not cleaved during SPPS(PEP-C); and that SC-PG is not cleaved during reaction(INRIFO);

with C-PEP, ResinA, DKP-PG, HG, SG, DPR, DKP, Xaa1, XaaC$^{(1)}$, XaaC, PEP-C, SC-PG, reaction(INRIFO) as defined above, also with all their preferred embodiments;

and with the connectivities between PEP-C, HG, SG and DPR and ResinA as defined above, also with all their preferred embodiments.

Further subject of the invention is a method(DKP-L) for preparation of a DKP-PG forming linker DKP-L, method(DKP-L) comprises a step (DKP-L-i), a step (DKP-L-iii) and optionally a step (DKP-L-ii);

in step (DKP-L-i) Xaa2 is coupled to Xaa1;

in optional step (DKP-L-ii) SG is coupled to Xaa2, if SG is present in DKP-L;

in step (DKP-L-iii) HG is coupled either to SG, if SG is present in DKP-L, or to Xaa2;

with DKP-PG, DKP-L, DKP, Xaa2, Xaa1, HG and SG as defined above, also with all their preferred embodiments.

The steps (DKP-L-i), (DKP-L-iii) and the optional step (DKP-L-ii) can be done in any order.

Preferably, at first the step (DKP-L-i) is done, then the optional step (DKP-L-ii) is done, if SG is present in DKP-L, and the step (DKP-L-iii) is done as the last step.

Further subject of the invention is a method(DKP-L-ResinA) for preparation of DKP-L-ResinA, method(DKP-L-ResinA) is a method(X1) or a method(X2);

method(X1) comprises a step (X1-i), a step (X1-ii), a step (X1-iv) and optionally a step (X1-iii);

in step (X1-i) the amino acid Xaa1 is coupled to ResinA;
in step (X1-ii) the amino acid Xaa2 is coupled to Xaa1;
in the optional step (X1-iii) SG is coupled to the side chain of Xaa2, if SG is present in DKP-L-ResinA;
in step (X1-iv) HG is coupled either to SG, if SG is present in DKP-L-ResinA, or to Xaa;

method(X2) comprises a step (X2-i);

in step (X2-i) DKP-L is coupled to ResinA;

with DKP-L-ResinA, ResinA, DKP-PG, DKP-L, DKP, Xaa2, Xaa1, HG and SG as defined above, also with all their preferred embodiments.

In method(X1), the steps (X14), (X1-ii), (X1-iv) and the optional step (X1-iii) can be done in any order.

Preferably, at first the step (X14), then the step (X1-ii) is done, then the optional step (X1-iiii) is done, if SG is present in DKP-L-ResinA, and the step (X1-iv) is done as the last step.

HG, any SG, Xaa2 and Xaa1, when used as building blocks in method(DKP-L-ResinA) or in method(DKP-L), can carry a protecting group:

Xaa1, used as building block in method(X1) or method(DKP-L), is used as a conventionally C-terminally protected amino acid, the protecting group being a protecting group C-PG. The alpha amino group of Xaa1 is unprotected and is the coupling site in the respective coupling reaction.

Xaa2, used as building block in method(X1) or method(DKP-L), is used as a conventionally N-terminally protected amino acid, the protecting group being a protecting group N-PG. The 1-carboxylic acid group of Xaa2 is unprotected and is the coupling sites in the respective coupling reaction.

Any side chain of Xaa1 or Xaa2 is preferably also protected by a SC-PG.

C-PG is a protecting group conventionally used in peptide chemistry for protecting the carboxylic acid group of an amino acid or for protecting the C-terminus of a peptide.

Preferably, C-PG is selected from the group consisting of basic cleavable type protecting groups, acid cleavable type protecting groups and reductively cleavable type protecting groups.

Each HG and SG, in form of individual building blocks used in the respective coupling reactions, has at least two reactive functional groups. The first reactive functional group is used as a functionality resembling the alpha amino group of an amino acid building block in peptide synthesis and can be protected by a suitable protecting group, preferably by a protecting group N-PG; preferably, this functional group is OH or $NH_2$ and is present in the protected state as —O— or —N(H)—.

The other reactive functional group of HG and SG is used as a functionality resembling the carboxylic acid group of an amino acid building block in peptide synthesis and is usually unprotected and is the coupling site in the respective coupling reaction. Preferably, this unprotected site is a carboxylic acid group. After this coupling reaction, any protecting group of the first reactive functional group, preferably said N-PG, can be cleaved in order to make this first functional group available for the next coupling reaction.

The DKP-PG forming linker DKP-L, obtainable by method(DKP-L), usually still carries any protecting group of HG in order to be usable in the coupling to ResinA in method (X2).

Prior to the coupling in method(X2), a C-PG of Xaa1 must be cleaved off. Preferably, method(DKP-L) comprises this cleaving of C-PG from Xaa1. Therefore, DKP-L comprises both embodiments, one embodiment with a protecting group C-PG on Xaa1, the other embodiment without a protecting group C-PG on Xaa1.

In DKP-L-ResinA, HG can still carry a protecting group which was present in the building block HG used for preparing DKP-L-ResinA. Any protecting group on HG must be cleaved prior to step (i) in method(C-PEP). Preferably, method(DKP-L-ResinA) comprises this cleaving of any protecting group from HG. Therefore, DKP-L-ResinA comprises both embodiments, one with any protecting group on HG, the other without any protecting group on HG.

Further subject of the invention is a method(PEP-HSPPS) for the preparation of a peptide PEP, method(PEP-HSPPS) comprises a step (i-pep) and a step (ii-pep), in step (i-pep) a peptide C-PEP is prepared according to method(C-PEP); then in step (ii-pep) C-PEP obtained in step (i-PEP) is coupled with an N-terminally protected amino acid or with an N-terminally protected peptide PEP-N by homogeneous solution phase peptide synthesis HSPPS;

with method(C-PEP), C-PEP and PEP-N being as defined above, also with all its preferred embodiments.

Method(PEP-HSPPS) is a method(C-PEP) comprising the further step (ii-pep).

Any side chain of PEP-N can be protected independently from any other side chain of PEP-N by a protecting group SC-PG, in case of more than one SC-PG being present in PEP-N, these SC-PG are independently from each other identical or different; with SC-PG being as defined above, also with all its preferred embodiment.

C-PEP in method(PEP-HSPPS) is used N-terminally unprotected. Therefore, any protecting group N-PG, which protects the N-terminus of C-PEP, is cleaved prior to the coupling reaction of method(PEP-HSPPS). This cleaving reaction is preferably comprised in method(C-PEP). Since PEP-C is made by SPPS(PEP-C), the N-terminal amino acid of PEP-C used in SPPS(C-PEP) is usually used with a protected amino group N-PG on its alpha amino group. Depending on the nature of this protecting group N-PG of the N-terminus of PEP-C this N-PG can be cleaved from the N-terminus simultaneously under the condition of the ring formation in reaction(INRIFO), or it can be cleaved from the N-terminus simultaneously with the cleaving of PG2 from Xaa2 prior to the reaction (INRIFO).

Further subject of the invention are following methods:

1. a method(PEP-HSPPS), wherein
   the DKP-L-ResinA of method(C-PEP) has been prepared by the method(DKP-L-ResinA);
2. a method(PEP-HSPPS), wherein
   the DKP-L-ResinA of method(C-PEP) has been prepared by method(X1) of the method(DKP-L-ResinA);
3. a method(PEP-HSPPS), wherein
   the DKP-L-ResinA of method(C-PEP) has been prepared by method(X2) of the method(DKP-L-ResinA); and wherein the DKP-L of method(DKP-L-ResinA) has been prepared by the method(DKP-L);
4. a method(C-PEP), wherein
the DKP-L-ResinA has been prepared by the method (DKP-L-ResinA);
5. a method(C-PEP), wherein
the DKP-L-ResinA has been prepared by method(X1) of the method(DKP-L-ResinA);
6. a method(C-PEP), wherein
the DKP-L-ResinA has been prepared by method(X2) of the method(DKP-L-ResinA);
and wherein
the DKP-L of method(DKP-L-ResinA) has been prepared by the method(DKP-L).

Further subject of the invention is a compound selected from the group consisting of C-PEP, PEP-C-DKP-L-ResinA, DKP-L-ResinA and DKP-L, with C-PEP, PEP-C-DKP-L-ResinA, DKP-L-ResinA and DKP-L as defined above, also with all their preferred embodiments.

Further subject of the invention is the use of C-PEP, with C-PEP being as defined above, also with all its preferred embodiments, in homogeneous solution phase peptide synthesis HSPPS for the preparation of a peptide PEP by a coupling reaction of C-PEP with an N-terminally protected amino acid or with an N-terminally protected peptide PEP-N.

Further subject of the invention is the use of a compound selected from the group consisting of C-PEP, PEP-C-DKP-L-ResinA, DKP-L-ResinA and DKP-L; or the use of DKP-L as a DKP-PG forming linker,
in peptide chemistry; or
for the preparation of a peptide; or
in a method for the preparation of a peptide; or
in a step of a method for the preparation of a peptide; or
in a peptide coupling reaction; or
in SPPS for the preparation of a peptide; or
in HSPPS for the preparation of a peptide;
with C-PEP, PEP-C-DKP-L-ResinA, DKP-L-ResinA, DKP-L and DKP-PG as defined above, also with all their preferred embodiments.

Any of the following embodiments of the invention are comprised in the hitherto described embodiments of the invention.

Further subject of the invention is a method(A) for the preparation of a compound of formula (III-PEP-PG)

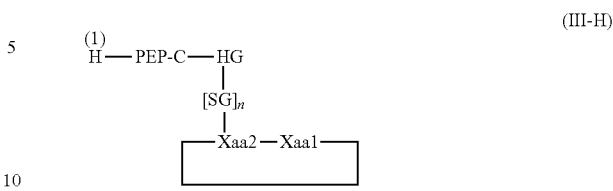
(III-PEP-PG)

by homogenous solution phase coupling of
an amino acid, which is N-terminally protected by a protecting group PGIII, or of
an N-terminally protected peptide fragment PEP-N, the N-terminally protected peptide fragment PEP-N being a compound of formula (III-PEP-N-PG), PGIII-(XaaN$^{(ipn)}$)$_{pn}$      (III-PEP-N-PG)

with a compound of formula (III-H);

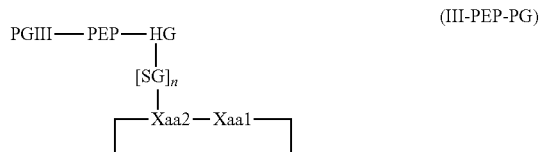
(III-H)

HG is a handle group conventionally used in solid phase peptide synthesis SPPS for connecting the C-terminus of a peptide to the solid phase, which allows for cleavage of the C-terminus from HG under conditions, which do not cleave an amide bond connecting two amino acid residues in a peptide;
n is 0 or 1;
SG is a spacer group conventionally used in peptide chemistry;
Xaa1 is an alpha amino acid residue;
Xaa2 is a 2-($C_{1-5}$ alkyl)-alpha amino acid residue, wherein the $C_{1-5}$ alkyl group is substituted by a functional group FG, FG is selected from the group consisting $NH_2$, OH, SH and COOH; FG is bonded with SG when n is 1; FG is bonded to HG when n is 0, and therefore FG is present in the compound of formula (III-PEP-PG) as a connecting group CG selected from the group consisting —N(H)—, —O—, —S— and —C(O)O—;
PEP-C is a peptidyl radical of formula (XaaC$^{(ipc)}$)$_{pc}$;
the hydrogen H denoted with (1) in formula (III-H) is a hydrogen of the unprotected N-terminus of PEP-C;
XaaC is an amino acid residue of the peptidyl radical PEP-C;
in XaaC$^{(ipc)}$, (ipc) signifies the index of XaaC of PEP-C at the position ipc, with the position count starting from the C-terminus of PEP-C,
pmax is 502;
pc is an integer of from 2 to (pmax-2) and represents the total number of amino acid residues in PEP-C;
ipc is an integer of from 1 to pc;
PGIII in formulae (III-PEP-PG) and (III-PEP-N-PG) are identical and is an N-terminal protecting group commonly used in peptide chemistry;
PEP is a peptidyl radical of formula (XaaP$^{(ip)}$)$_p$;
pn is an integer of from 2 to (pmax-pc) and represents the total number of amino acid residues in PEP-N;
p is pc+pn;
XaaN is an amino acid residues of the peptide fragment PEP-N;
in XaaN$^{(ipn)}$, (ipn) signifies the index of XaaN of PEP-N at the position ipn, with the position count starting from the C-terminus of PEP-N;
XaaP is an amino acid residue;
in XaaP$^{(ip)}$, (ip) signifies the index of XaaP of PEP at the position ip, with the position count starting from the C-terminus of PEP;
ipn is an integer of from 1 to pn;
ip is an integer of from 1 to p;
with the proviso, that XaaP$^{(ip)}$ is identical with XaaC$^{(ipc)}$ for ip having a value from 1 to ipc;
and XaaP$^{(ip)}$ is identical with XaaN$^{(ipn)}$ for ip having the value (pc+ipn);
with pmax, pc, XaaC, XaaC$^{(ipc)}$, ipc and compound of formula (III-H) being as defined above, also with all their preferred embodiments;

XaaC in formula (III-H) and XaaN are independently from each other identical or different.

Therefore, PEP-C is a peptidyl radical having pc amino acid residues XaaC.

Preferably, the alpha amino group of Xaa1 is coupled to the 1-carboxy group of Xaa2 by a peptide bond.

Compound of formula (III-H) is an embodiment of the above defined C-PEP.

HG, SG, Xaa2 and Xaa1 are embodiments of the respective HG, SG, Xaa2 and Xaa1 of the above defined peptide C-PEP. The cyclic dipeptide in e.g. formula (III-H) is one embodiment of the above mentioned DKP, i.e. the diketopiperazine residue derived from DPR.

Preferably, PEP-C is prepared by SPPS.

The SPPS, by which PEP-C is prepared, is called above SPPS(PEP-C).

Preferably, PEP-C is a peptidyl radical of formula $(XaaC^{(ipc)})_{pc}$, which has been synthesized by SPPS using amino acids of formula $PGXaaC^{(ipc)}$-$XaaC^{(ipc)}$-OH.

PGXaaC is an N-terminal protecting group conventionally used in SPPS and is selected from the group consisting of basic cleavable type protecting groups, acid cleavable type protecting groups and reductively cleavable type protecting groups.

In $PGXaaC^{(ipc)}$, the index (ipc) defines $PGXaaC^{(ipc)}$ as the protecting group of the amino acid $PGXaaC^{(ipc)}$-$XaaC^{(ipc)}$-OH, with each $PGXaaC^{(ipc)}$ being independently from each other identical or different from another $PGXaaC^{(ipc)}$.

Preferably, PGXaaC and $PGXaaC^{(ipc)}$ respectively is an N-terminal protecting group conventionally used in SPPS to protect the alpha amino group of any amino acid PGXaaC-XaaC-OH and $PGXaaC^{(ipc)}$-$XaaC^{(ipc)}$-OH respectively used in the SPPS to synthesize PEP-C.

In order to avoid complexity of the description, the abbreviations PGXaaC in the text is used either for the protecting group of the amino acids used to synthesis PEP-C and C-PEP, or it is used for the N-terminal protecting group of the N-terminal amino acid residues of PEP-C and C-PEP at the various stages during SPPS. The skilled person can unambiguously distinguish from the context, which of the two meanings is meant.

Therefore, PEP-N is a peptidyl radical having pn amino acid residues XaaN.

Therefore, PEP is a peptidyl radical having p amino acid residues XaaP.

The residue of formula (III-res)

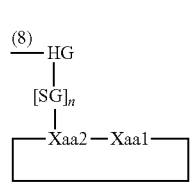

(III-res)

which appears e.g. in the formulae (III-PEP-PG) and (III-H), is an embodiment of the DKP-PG mentioned above;
with HG, SG, n, Xaa2 and Xaa1 being as defined above;
with Xaa2 and Xaa1 forming the DKP mentioned above;
and with (8) denoting the bond between the peptidyl radical PEP-C and HG.

Compound of formula (III-PEP-PG) is an embodiment of above defined peptide PEP and can also be an embodiment of above defined C-PEP.

PEP-N can be prepared by conventional peptide synthesis, either by SPPS, by HSPPS or by a combination of SPPS and HSPPS, preferably by SPPS.

In case that the compound of formula (III-PEP-PG) shall be used in a next HSPPS coupling according to method(A) as a next fragment C-PEP with a next fragment PEP-N, only the N-terminal protecting group PGIII of said compound of formula (III-PEP-PG) needs to be removed, to provide for said next fragment C-PEP, i.e. for the next compound of formula (III-H), for said next HSPPS coupling according to method (A).

Since both the compound of formula (III-H) and PEP-N may themselves have been prepared by method(A) in one of their preparation steps, they can have practically any number of amino acids as long as the solution phase coupling still works in a reasonable time.

Preferably, pmax is 500, more preferably pmax is 400 or 402, even more preferably 300 or 302, especially 200 or 202, more especially 150 or 152, even more especially 100 or 102, particularly 80 or 82, more particularly 50 or 52, even more particularly 25 or 27.

Preferably, the peptidyl radical PEP-C is a linear peptidyl radical, and preferably PEP-N is a linear peptide, resulting in a linear peptidyl radical PEP.

Preferably, if PEP-C in compound of formula (III-H) and/or PEP-N have been prepared using SPPS, they have independently from each other of from 2 to 100, more preferably of from 2 to 50, even more preferably of from 2 to 40, especially preferably of from 2 to 25 amino acid residues.

Preferably, if PEP-C in compound of formula (III-H) and/or PEP-N have been prepared using HSPPS, they have independently from each other from of 2 to 250, more preferably of from 2 to 200, even more preferably of from 2 to 100, especially preferably of from 2 to 50, in particular of from 2 to 25 amino acid residues.

Any functional groups on the side chains of the individual amino acid residues of peptidyl radical PEP-C and of PEP-N are independently from each protected or unprotected by protecting groups SC-PG;

preferably, all functional groups on the side chains of the individual amino acid residues of peptidyl radical PEP-C and of PEP-N are protected by protecting groups SC-PG or unprotected;

more preferably, all functional groups on the side chains of the individual amino acid residues of peptidyl radical PEP-C and of PEP-N are protected during the solution phase coupling according to method(A) of fragment PEP-N with compound of formula (III-H), even more preferably, all functional groups on the side chains of the individual amino acid residues of peptidyl radical PEP-C and of PEP-N are protected by strong type PG.

Preferably, the C terminus or, in case that the C-terminal amino acid residue has a side chain, the side chain of the C-terminal amino acid residue of the peptidyl radical PEP or PEP-C respectively, is bonded to HG;

more preferably, the C terminus of the peptidyl radical PEP or PEP-C respectively, is bonded to HG.

Preferably,

HG is a handle group conventionally used in solid phase peptide synthesis SPPS to connect an amino acid, which will become the C-terminal amino acid residue of a peptide, which is to be synthesised by SPPS, via said HG to a solid phase, preferably to a ResinA.

HG allows for cleavage of the C-terminal amino acid residue from HG under conditions, which do not cleave an amide bond connecting two amino acid residues in a peptide.

More preferably,

HG is a handle group selected from the group consisting of handle group of formula (HGF-I), handle group of formula (HGF-II), handle group of formula (HGF-III), handle group of formula (HGF-IV), handle group of formula (HGF-V) and handle group of formula (HGF-VI),

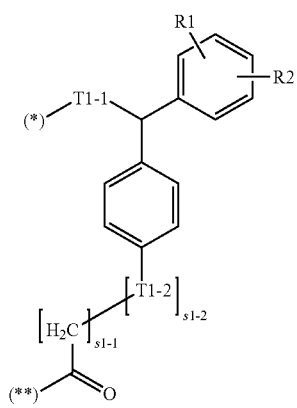
(HGF-I)

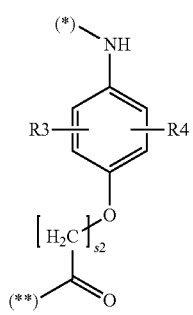
(HGF-II)

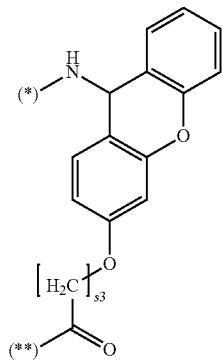
(HGF-III)

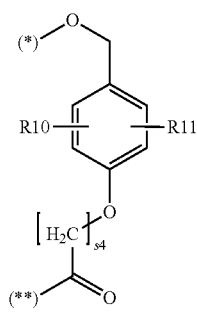
(HGF-IV)

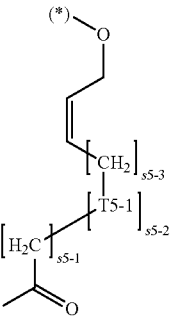
(HGF-V)

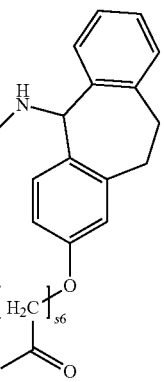
(HGF-VI)

wherein
(*) denotes the bond between the C atom of the C terminus of the respective peptidyl radical, e.g. of PEP for formulae (III-PEP-PG), of PEP-C for formula (III-H) or of PEP-C in method(C-PEP), and HG,
or denotes, in case that the C-terminal amino acid residue of the respective peptidyl radical, e.g. of PEP for formulae (III-PEP-PG), of PEP-C for formula (III-H) or of PEP-C in method(C-PEP), has a side chain and is connected via this side chain to HG, the bond between the side chain of the C terminal amino acid residue of the respective peptidyl radical, e.g. of PEP for formulae (III-PEP-PG), of PEP-C for formula (III-H) or of PEP-C in method(C-PEP), and HG,
(**) denotes the bond between HG and SG when n is 1, or denotes the bond between HG and FG when n is 0, with SG and FG as defined above, also with all their preferred embodiments;
R1, R2, R3, R4, R10 and R11 are identical or different and independently from each other selected from the group consisting of hydrogen and O—$C_{1-4}$ alkyl,
s1-1, s2, s3, s4 and s6 are identical or different and independently from each other selected from the group consisting of 1, 2, 3 and 4,
s5-1 is 0, 1, 2, 3 or 4,
s1-2, s5-2 and s5-3 are identical or different and independently from each other 0 or 1,
T1-1 is O or NH,
T1-2 and T5-1 are O,
with n, SG, FG, PEP-C and method(C-PEP) as defined above, also with all their preferred embodiments.

Preferably,
(*) denotes the bond between the C atom of the C terminus of the respective peptidyl radicals, e.g. of PEP for formulae (III-PEP-PG), of PEP-C for formula (III-H) or of PEP-C in method(C-PEP), and HG.

Preferably,

SG is a spacer group conventionally used in SPPS, preferably comprising one or more, more preferably 1 to 500, ethylenoxide units.

More preferably,

SG is a spacer group selected from the group consisting of spacer group of formula (SG-I), spacer group of formula (SG-II), spacer group of formula (SG-III), spacer group of formula (SG-IV) and spacer group of formula (SG-V);

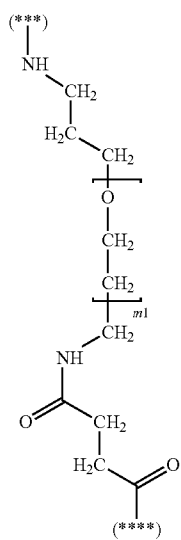
(SG-I)

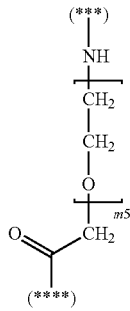
(SG-II)

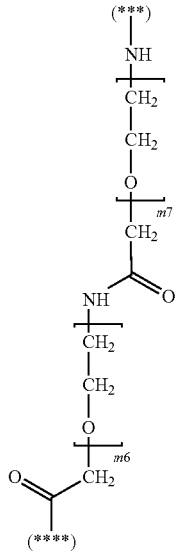
(SG-III)

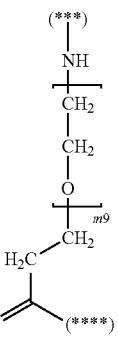
(SG-IV)

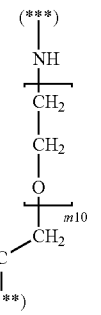
(SG-V)

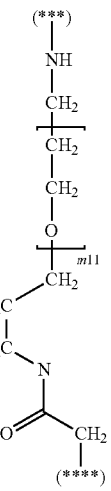
(SG-VI)

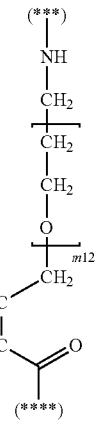
(SG-VII)

m1, m5, m6, m7, m9, m10, m11 and m12 are identical or different and independently from each other an integer of 1 to 500;

m2, m3 and m4 are identical or different and independently from each other 1, 2, 3 or 4, (*) is the bond from SG to HG when n is 1, (**) is the bond between SG and Xaa2 when n is 1.

(*) is the bond denoted by () in the respective embodiments of HG, when n is 1.

(****) is the bond between SG and FG, when n is 1;

with HG, Xaa2 and n as defined above, also with all their preferred embodiments.

Preferably, XaaC and XaaN are alpha amino acid residues.

More preferably, XaaC and XaaN are naturally occurring alpha amino acid residues.

If XaaC or XaaN carries a side chain with a functional group, this functional group of the side chain of XaaC or XaaN is either protected or unprotected, preferably it is protected.

More preferably, XaaC and XaaN are identical or different and are independently from each other selected from the group consisting of Ala, Aib, Cys, Asp, Glu, Phe, Gly, His, Ile, Lys, Leu, Met, Asn, Pro, Gln, Arg, Ser, Thr, Val, Trp, Tyr, Asp, Asn, Glu and Gln;

where any functional group in the side chain is either protected or unprotected, preferably protected.

Preferably, PGIII is selected from the group consisting of basic type PGs, strong type PGs, weak type PGs and reductive type PGs.

If all functional groups on the side chains of the individual amino acid residues of peptidyl radical PEP-C and of PEP-N are protected by strong acid cleavable type protecting groups, and in case that the compound of formula (III-PEP-PG) shall be used in a next HSPPS coupling according to method(A) as a next fragment C-PEP with a next fragment PEP-N, then PGIII is preferably selected from the group consisting of basic type PGs, weak type PGs and reductive type PGs.

Handle groups of formula (HGF-I) and handle groups of formula (HGF-IV) are cleavable from the PEP-C by strong cleaving conditions, handle groups of formula (HGF-II) are cleavable by strong cleaving conditions, handle groups of formula (HGF-III) are cleavable by weak or by strong cleaving conditions, handle groups of formula (HGF-V) are cleavable by reductive cleaving conditions, and handle groups of formula (HGF-VI) are cleavable by weak or by strong cleaving conditions Preferably, HG is a handle group selected from the group consisting of handle group of formula (HGF-I), handle group of formula (HGF-IV) and handle group of formula (HGF-VI).

Preferably, R1, R2, R3, R4, R10 and R11 are identical or different and independently from each other selected from the group consisting of hydrogen and O—CH$_3$.

More preferably, R1 and R2 are identical and selected from the group consisting of hydrogen and O—CH$_3$.

More preferably, R3, R4, R10 and R11 are O—CH$_3$.

Preferably, s1-1 and s6 are 1.

Preferably, s1-2, s5-1, s5-2 and s5-3 are independently from each other 0 or 1.

Preferably, s2 and s3 are 4.

Preferably, s4 is 1 or 2.

Preferably, T1-1 is NH, s1-1 is 1 and s1-2 is 1.

Preferably, T1-1 is O, s1-1 is 1 and s1-2 is 0.

Preferably, T1-1 is O, s1-1 is 1 and s1-2 is 1.

Especially, HG is a handle group selected from the group consisting of handle group of formula (HG-Ia), handle group of formula (HG-Ib), handle group of formula (HG-Ic), handle group of formula (HG-Id), handle group of formula (HG-II), handle group of formula (HG-III), handle group of formula (HG-IVa), handle group of formula (HG-IVb), handle group of formula (HG-Va), handle group of formula (HG-Vb) and handle group of formula (HG-VI),

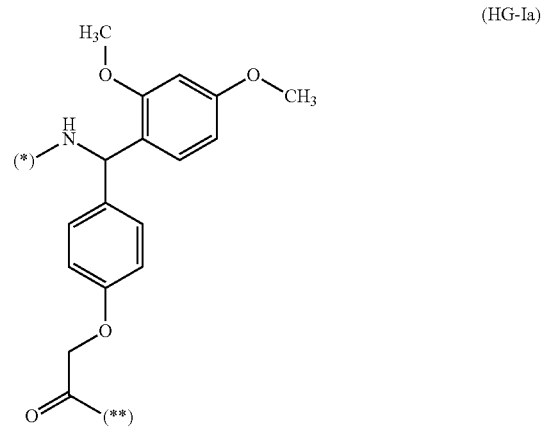

(HG-Ia)

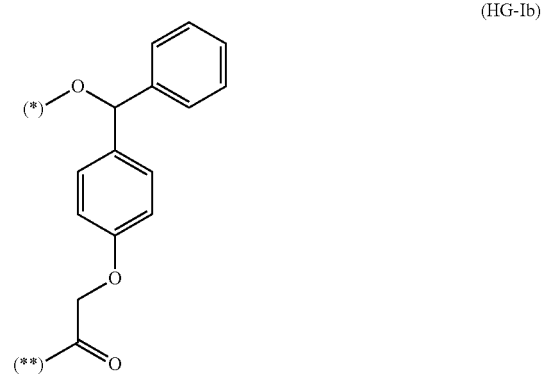

(HG-Ib)

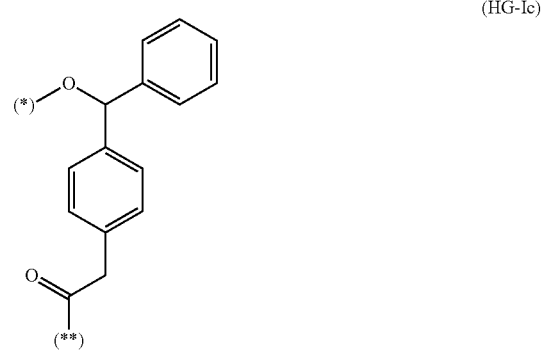

(HG-Ic)

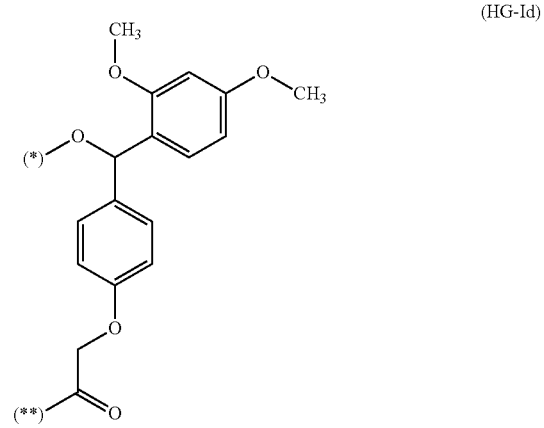

(HG-Id)

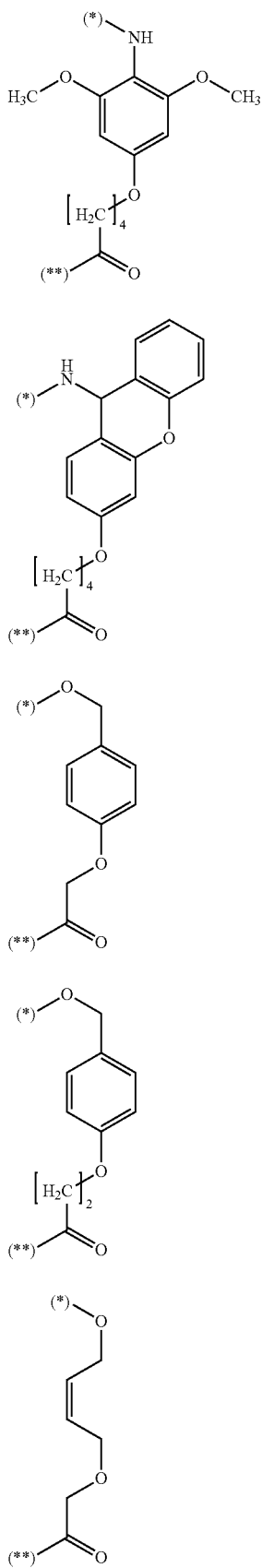
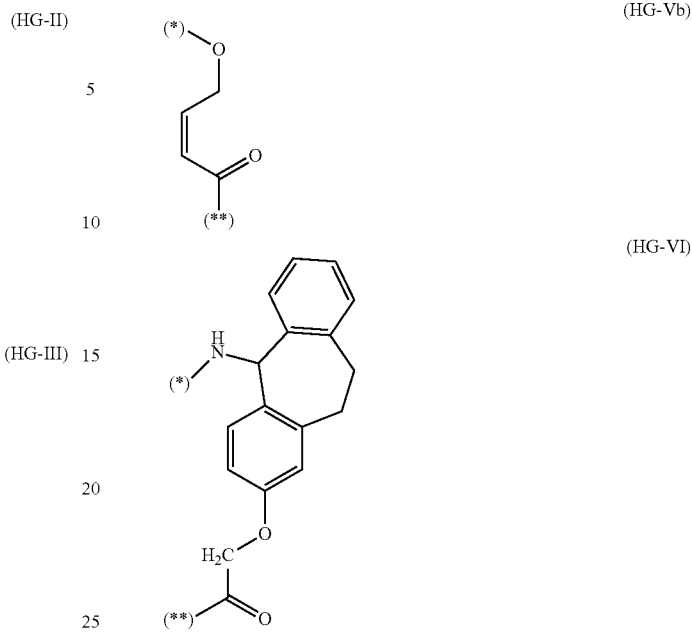

wherein
(*) is as defined above, also with all its preferred embodiments,
(**) is as defined above, also with all its preferred embodiments.

More especially, HG is a handle group selected from the group consisting of handle group of formula (HG-Ia), handle group of formula (HG-Ib), handle group of formula (HG-Ic), handle group of formula (HG-Id), handle group of formula (HG-IVa), handle group of formula (HG-IVb), and handle group of formula (HG-VI).

Even more especially, HG is a handle group of formula (HG-Ia), a handle group of formula (HG-IVa) or a handle group of formula (HG-VI).

The various handle groups HG are known handle groups or are structurally closely related derivatives of known handle groups. The reaction conditions necessary for cleaving any of these handle groups HG from a peptidyl radical connected to the respective handle group HG, are also known in peptide chemistry.

The handle group of formula (HG-Ia) is derived from the Rink amide handle, (HG-Ib), (HG-Ic) and (HG-Id) from benzhydryl handles, (HG-II) from the PAL handle, (HG-III) from the Sieber handle, (HG-IVa) from the HMPA(-Wang) handle, (HG-IVb) from the HMPP(-Wang) handle, and (HG-Va) and (HG-Vb) from allyl handles, (HG-VI) from Ramage handle.

Preferably, m1, m5, m6, m7, m9, m10, m11 and m12 are identical or different and independently from each other 1, 2, 3, 4, 5, 6, 7, 8, 9, 10, 11, 12, 13, 14, 15, 16, 17, 18, 19, 20, 21, 22, 23, 24, 25, 26, 27, 28, 29, 30;

more preferably, m1, m5, m6, m7, m9, m10, m11 and m12 are identical or different and independently from each other 1, 2, 3, 4, 5, 6, 7, 8, 9, 10, 11, 12, 23 or 27;

even more preferably m1, m5, m6, m7, m10, m11 and m12 are identical or different and independently from each other 1, 2, 3, 4, 5, 6, 7, 8, 9 or 10; m9 is 4, 8, 12 or 27;

especially m1 is 3; m5 is 1 or 2; m6 and m7 are 2; m9 is 4, 8, 12 or 27; m10 is 1; m11 is 3.

Xaa1 is preferably selected from the group consisting of non-naturally occurring alpha amino acids, naturally occurring alpha amino acid residues;

more preferably selected from the group consisting of naturally occurring alpha amino acid residues, alpha-N-methylamino acid residues, L-Hpr residue, D-Hpr residue, DL-Hpr residue, 2-($C_{1-5}$-alkyl)-D-amino acid residues, 2-($C_{1-5}$-alkyl)-L-amino acid residues, 2-($C_{1-5}$-alkyl)-DL-amino acid residue and a residue derived from compound of formula (HypX);

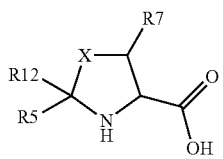

(HypX)

wherein
X is O, S or C(R13)R14;
R5, R7, R12, R13 and R14 are identical or different and independently from each other selected from the group consisting of hydrogen, $C_{1-4}$ alkyl and O—R8;
R8 is a protecting group conventionally used for side chain protection in peptide chemistry, or a substituent of formula (Sub-R8);

(Sub-R8)

wherein
m8 is 1, 2, 3, 4, 5, 6, 7, 8, 9 or 10;
R9 is $C_{1-4}$ alkyl.
Preferably,
X is C(R13)R14;
R5, R7, R12 and R14 are hydrogen;
R13 is O—R8;
R8 is a protecting group conventionally used for side chain protection in peptide chemistry.
The alpha-N-methylamino acid residues is preferably selected from the group consisting of L-alpha-N-methylamino acid residues, D-alpha-N-methylamino acid residues and DL-alpha-N-methylamino acid residues;
more preferably selected from the group consisting of N-methylglycine residue (sarcosine), L-N-methylphenylalanine residue, D-N-methylphenylalanine residue, DL-N-methylphenylalanine residue, L-N-methylalanine residue, D-N-methylalanine residue, DL-N-methylalanine residue, L-N-methylvaline residue, D-N-methylvaline residue, DL-N-methylvaline residue, L-N-methyltryptophane residue, D-N-methyltryptophane residue, DL-N-methyltryptophane residue.
The naturally occurring alpha amino acid residue is preferably selected from the group consisting of Pro residue and Gly residue; more preferably selected from the group consisting of L-Pro residue, D-Pro residue, DL-Pro residue and Gly residue.
Preferably, compound of formula (HypX) is derived from L-Hyp, D-Hyp or DL-Hyp, more preferably from L-4Hyp, D-4Hyp or DL-4Hyp.
Especially, Xaa1 is selected from the group consisting of L-N-methylglycine residue, D-N-methylglycine residue, DL-N-methylglycine residue, L-N-methylphenylalanine residue, D-N-methylphenylalanine residue, DL-N-methylphenylalanine residue, L-Pro residue, D-Pro residue, DL-Pro residue, side chain protected L-Hyp residue, side chain protected D-Hyp residue, side chain protected DL-Hyp residue, L-Hpr residue, D-Hpr residue and DL-Hpr residue; with Hyp being preferably 4Hyp.

More especially, Xaa1 is L-N-methylphenylalanine residue, D-N-methylphenylalanine residue, DL-N-methylphenylalanine residue, L-Pro residue, D-Pro residue, DL-Pro residue, side chain protected L-Hyp residue, side chain protected D-Hyp residue, side chain protected DL-Hyp residue; with Hyp being preferably 4Hyp.

Even more especially, Xaa1 is D-Pro residue, D-N-methylphenylalanine residue or side chain protected D-Hyp residue; with Hyp being preferably 4Hyp.

FG is bonded with SG via the bond (*) in the respective embodiments of SG, when n is 1, or FG is bonded to HG via the bond () in the respective embodiments of HG.

Preferably, Xaa9 is selected from the group consisting of L-Lys residue, D-Lys residue, DL-Lys residue, L-Orn residue, D-Orn residue, DL-Orn residue, L-4-aminoproline residue, D-4-aminoproline residue, DL-4-aminoproline residue, L-alpha,gamma-diamino¬butanoic acid residue, D-alpha,gamma-diaminobutanoic acid residue, DL-alpha,gamma-diamino¬butanoic acid residue, L-alpha,beta-diaminopropanoic acid residue, D-alpha,beta-diamino¬propanoic acid residue, DL-alpha,beta-diaminopropanoic acid residue, L-Ser residue, D-Ser residue, DL-Ser residue, L-Thr residue, D-Thr residue, DL-Thr residue, L-Cys residue, D-Cys residue, DL-Cys residue, L-homocysteine residue, D-homocysteine residue, DL-homocysteine residue, L-Asp residue, D-Asp residue, DL-Asp residue, L-Glu residue, D-Glu residue and DL-Glu residue.

Preferably, FG is $NH_2$ or OH, more preferably $NH_2$; therefore CG is preferably —N(H)— or —O—, more preferably —N(H)—; therefore Xaa2 is preferably selected accordingly.

More preferably, Xaa2 is selected from the group consisting of L-Lys residue, D-Lys residue, DL-Lys residue, L-alpha,beta-diamino¬propanoic acid residue, D-alpha,beta-diamino¬propanoic acid residue and DL-alpha,beta-diamino¬propanoic acid residue.

Even more preferably, Xaa2 is L-Lys residue or L-alpha,beta-diamino¬propanoic acid residue.

A preferred embodiment is the combination, wherein the Xaa2 is an L-alpha amino acid residue and Xaa1 is a D-alpha amino acid residue, or alternatively Xaa2 is a D- and Xaa1 is a L-alpha-amino acid residue, with Xaa1 and Xaa2 as defined above, also with all their preferred embodiments.

More preferably, Xaa1 is selected from the group consisting of L-Pro residue, D-Pro residue, DL-Pro residue, L-N-methylphenylalanine residue, D-N-methylphenylalanine residue and DL-N-methylphenylalanine residue; and Xaa2 is selected from the group consisting of L-Lys residue, D-Lys residue, DL-Lys, L-alpha,beta-diamino¬propanoic acid residue, D-alpha,beta-diamino¬propanoic acid residue and DL-alpha,beta-diamino¬propanoic acid residue.

Even more preferably, Xaa1 is D-Pro or D-N-methylphenylalanine residue, and Xaa2 is L-Lys or L-alpha,beta-diamino¬propanoic acid residue; or Xaa1 is L-Pro or L-N-methylphenylalanine residue, and Xaa2 is D-Lys or D-alpha,beta-diamino¬propanoic acid residue.

Especially, Xaa2 is of L- and Xaa1 is of D-configuration, with Xaa1 and Xaa2 as defined above, also with all their preferred embodiments.

More especially, Xaa1 is D-Pro or D-N-methylphenylalanine residue, and Xaa2 is L-Lys or L-alpha,beta-diamino¬propanoic acid residue.

The homogenous solution phase coupling in method(A), i.e. HSPPS, is carried out using conventional process parameters and reagents typical for HSPPS.

HSPPS is conventionally done in a solvent and using one or more coupling reagents, and is done preferably in the presence of one or more coupling additives, and preferably in the presence of one or more tertiary bases.

Preferable coupling reagents used in HSPPS are phoshonium or uronium salts and carbodiimide coupling reagents.

Phosphonium and uronium salts are preferably derivatives of benzotriazol; more preferably Phosphonium and uronium salts are selected from the group consisting of BOP (Benzotriazole-1-yl-oxy-tris-(dimethyl amino)-phosphonium hexafluorophosphate),
PyBOP (Benzotriazol-1-yl-oxy-trispyrrolidinophosphonium hexafluorophosphate),
HBTU (O-(1H-benzotriazole-1-yl)-1,1,3,3-tetramethyluronium hexafluorophosphate),
HCTU (O-(1H-6-chloro-benzotriazole-1-yl)-1,1,3,3-tetramethyluronium hexafluorophosphate),
TCTU (O-(1H-6-chlorobenzotriazole-1-yl)-1,1,3,3-tetramethyluronium tetrafluoroborate),
HATU (O-(7-azabenzotriazol-1-yl)-1,1,3,3-tetramethyluronium hexafluorophosphate),
TATU (O-(7-azabenzotriazol-1-yl)-1,1,3,3-tetramethyluronium tetrafluoroborate),
TBTU (O-(benzotriazol-1-yl)-1,1,3,3-tetra¬methyluronium tetrafluoroborate),
TOTU (O-[cyano(ethoxycarbonyl)methyleneamino]-1,1,3,3-tetramethyluronium tetrafluoroborate),
HAPyU (O-(benzotriazol-1-yl)oxybis-(pyrrolidino)-uronium hexafluorophosphate,
PyAOP (Benzotriazole-1-yl-oxy-tris-pyrrolidino-phosphonium hexafluorophosphate),
COMU (1-[(1-(cyano-2-ethoxy-2-oxoethylideneaminooxy)-dimethylamino-morpholinomethylene)]methanaminium-hexafluorophosphate),
PyClock (6-chloro-benzotriazole-1-yl-oxy-tris-pyrrolidino-phosphonium hexafluorophosphate),
PyOxP (O-[(1-cyano-2-ethoxy-2-oxoethylidene)amino]-oxytri(pyrrolidin-1-yl) phosphonium hexafluorophosphate) and
PyOxB (O-[(1-cyano-2-ethoxy-2-oxoethylidene)amino]-oxytri(pyrrolidin-1-yl) phosphonium tetrafluoroborate).

Carbodiimide coupling reagents are preferably selected from the group consisting of diisopropyl-carbodiimide (DIC), dicyclohexyl-carbodiimide (DCC) and water-soluble carbodiimides (WSCDI) such as 1-ethyl-3-(3-dimethylaminopropyl)¬carbo¬diimide (EDC)

Other coupling techniques use pre-formed active esters, such as hydroxysuccinimide (HOSu) and p-nitrophenol (HONp) esters, pre-formed symmetrical anhydrides, non-symmetrical anhydrides such as N-carboxyanhydrides (NCAs) and acid halides, such as acyl fluoride or acyl chloride.

Preferred coupling reagents are phoshonium or uronium coupling reagents, especially TCTU, TOTU or PyBop.

Preferably, the conjugated acid of said tertiary base used in HSPPS has a pKa value of from 7.5 to 15, more preferably of from 7.5 to 10. Said tertiary base is preferably trialkylamines, such as diisopropylethylamine (DIEA) or triethylamine (TEA), further N,N'-di-$C_{1-4}$ alkylanilines, such as N,N-diethylaniline, 2,4,6-tri-$C_{1-4}$ alkylpyridines, such as collidine (2,4,6-trimethylpyridine), or N—$C_{1-4}$ alkyl-morpholines, such as N-methylmorpholine, with any $C_{1-4}$ alkyl being identical or different and independently from each other straight or branched $C_{1-4}$ alkyl.

A coupling additive is preferably a nucleophilic hydroxy compound capable of forming activated esters, more preferably having an acidic, nucleophilic N-hydroxy function wherein N is imide or is N-acyl or N-aryl substituted triazeno, the triazeno type coupling additive being preferably a N-hydroxy-benzotriazol derivative (or 1-hydroxy-benzotriazol derivative) or a N-hydroxybenzotriazine derivative. Such coupling additives have been described in WO 94/07910 and EP 410 182. Since they also act as scavengers, they are also called scavengers.

Preferred coupling additives are selected from the group consisting of

N-hydroxy-succinimide (HOSu), 6-Chloro-1-hydroxy-benzotriazole (Cl-HOBO, N-hydroxy-3,4-dihydro-4-oxo-1,2,3-benzotriazine (HOOBt), 1-hydroxy-7-azabenzotriazole (HOAt), 1-hydroxy-benzotriazole (HOBt) and
ethyl 2-cyano-2-hydroxyimino¬acetate (CHA).

CHA is available under trade name OXYMAPURE®. CHA has proved to be an effective scavenger as racemization is more suppressed compared to benzotriazole-based scavengers. In addition, CHA is less explosive than e.g. HOBt or Cl-HOBt, so that its handling is advantageous, and, as a further advantage, the coupling progress can be visually monitored by a colour change of the reaction mixture.

Preferably, HOBt or CHA, more preferably HOBt is used.

In a preferred embodiment, the combination of reagents in the HSPPS reaction is selected from the group consisting of TCTU/Cl-HOBt/DIPEA, TOTU/CHA/DIPEA and PyBop/HOBt/DIPEA.

As solvent, any inert liquid solvent, which can dissolve the reactants, may be used in HSPPS.

Preferred solvents are selected from the group consisting of dimethyl sulfoxide (DMSO), dioxane, tetrahydrofuran (THF), 1-methyl-2-pyrrolidone (NMP), N,N-dimethylformamide (DMF), N,N-dimethylacetamide (DMA), pyridine, dichloromethane (DCM), dichloroethane (DCE), chloroform, dioxane, tetrahydropyran, ethyl acetate, toluene, acetonitrile and mixtures thereof.

More preferred solvents are NMP, DMF and mixtures thereof.

Preferably, HSPPS is done at a temperature of from 0 to 50° C., more preferably of from 5 to 30° C., even more preferably of from 15 to 25° C.

Preferably, HSPPS is done at atmospheric pressure.

Preferably, the reaction time for HSPPS is of from 15 min to 20 h, more preferably of from 30 min to 5 h, even more preferably of from 30 min to 2 h.

The term "part" in this description of reaction conditions of HSPPS is meant to be a factor of the parts by weight of the combined peptide material, if not otherwise stated.

Preferably, of from 1 to 30 parts, more preferably of from 5 to 10 parts, of solvent are used.

Preferably, of from 0.9 to 5 mol equivalents, more preferably of from 1 to 1.5 mol equivalents, of coupling reagent is used, the mol equivalent being based on the mol of reactive C-terminal carboxy groups.

Preferably, of from 0.1 to 5 mol equivalents, more preferably of from 0.5 to 1.5 mol equivalents, of coupling additive is used, the mol equivalent being based on the mol of coupling reagent.

Preferably, of from 1 to 10 mol equivalents, more preferably of from 2 to 3 mol equivalents, of tertiary base is used, the mol equivalent being based on the mol of coupling reagent.

If the N-terminally and C-terminally protected PEP, which was prepared according to method(A), represents the target peptide, preferably the N-terminal protecting group and the C-terminal protecting group and any side chain protecting group are removed after the preparation according to method (A), to provide for the unprotected peptide PEP. This is usually called global deprotection.

The global deprotection conditions, which need to be applied, depend on the nature of the chosen PG. Preferably, the involved PGs are selected to allow global deprotection under weak, strong or reductive cleaving conditions, as defined above, depending on the nature of PGs.

The C-terminal protecting group of PEP, i.e. the DKP-PG, can be cleaved by conditions applicable for cleaving the respective handle group HG from the peptidyl radical, these conditions are known in peptide chemistry. Usually, the conditions are either reductive, weak or strong cleaving conditions, as defined above.

Preferably, the handle group HG is chosen to be cleavable under acidic conditions from the peptidyl radical PEP, and in this case, if the N-terminal protecting group of fragment PEP-N is a basic cleavable type protecting group or a reductively cleavable type protecting group, the N-terminal protecting group and the C-terminal protecting group and any side chain protecting group are removed preferably after the preparation according to method(A) in two steps; but if the N-terminal protecting group of fragment PEP-N is acid type removable protecting group, the N-terminal protecting group and the C-terminal protecting group and any side chain protecting group are removed preferably after the preparation according to method(A) in one step.

Any side chain protecting groups are typically retained until the end of the HSPPS. This deprotection reaction can be carried out under conditions applicable for the various side chain protecting groups, which have been used, and these conditions are known in peptide chemistry. In the case that different types of side chain protecting groups are chosen, they may be cleaved successively. Advantageously, the side chain protecting groups are chosen, so that they are cleavable simultaneously, and more advantageously concomitantly with N-terminal protecting group of PEP.

Usually, side chain PGs are cleaved by strong, weak or reductive cleaving conditions as defined above.

Further subject of the invention is the use (A) of compound of formula (III-H), with the compound of formula (III-H) being as defined above, also with all its preferred embodiments, for the preparation of a peptide PEP;

preferably the use (A) of compound of formula (III-H), with the compound of formula (III-H) being as defined above, also with all its preferred embodiments, in homogeneous solution phase peptide synthesis for the preparation of a peptide PEP by a coupling reaction of the compound of formula (III-H) with an N-terminally protected amino acid or with an N-terminally protected PEP-N, with PEP-N being as defined above, also with all its preferred embodiments.

Use (A) is an embodiment of the above defined use of C-PEP in HSPPS.

Further subject of the invention is a method(B) for the preparation of a compound of formula (III-H), with the compound of formula (III-H) being as defined above, also with all its preferred embodiments, characterized by cleaving a protecting group PGXaaC$^{(pc)}$ from a compound of formula (III-PGXaaC$^{(pc)}$);

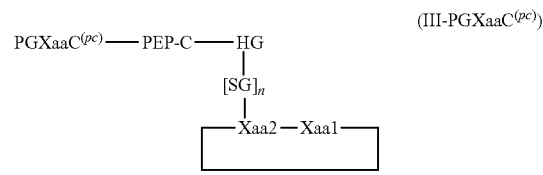

wherein
PGXaaC is an N-terminal protecting group conventionally used in SPPS and is selected from the group consisting of basic cleavable type protecting groups, acid cleavable type protecting groups and reductively cleavable type protecting groups;
pc, XaaC, PEP-C, HG, n, SG, Xaa1 and Xaa2 have the same definition as above, also with all their preferred embodiments,
in PGXaaC$^{(pc)}$, the index (pc) defines PGXaaC$^{(pc)}$ as the N-terminal protecting group of PEP-C;
with the proviso, that PGXaaC$^{(pc)}$ is chosen to be of such a cleavable type protecting group, that PGXaaC$^{(pc)}$ can be cleaved from PEP-C without cleaving PEP-C from HG.

Preferably, if PEP-C carries side chain PGs, PGXaaC$^{(pc)}$ is chosen to be of such a cleavable type protecting group, that PGXaaC$^{(pc)}$ can be cleaved from PEP-C without cleaving any side chain PGs from PEP-C.

PGXaaC$^{(pc)}$ therefore is the protecting group of the N-terminal amino acid residue of PEP-C, which is an embodiment of N-PG.

Method(B) is comprised in above defined method(C-PEP).
Compound of formula (III-PGXaaC$^{(pc)}$) is an embodiment of the above defined C-PEP.

If PGXaaC$^{(pc)}$ is a basic type PG, it is preferably Fmoc.
If PGXaaC$^{(pc)}$ is a strong type PG, it is preferably Boc.
If PGXaaC$^{(pc)}$ is a weak type PG, it is preferably Trt.
If PGXaaC$^{(pc)}$ is a reductive type PG, it is preferably Alloc.
PGXaaC$^{(pc)}$ is, depending on its type, cleaved by strong, weak, basic or reductive cleaving conditions, these conditions being as defined above.

Further subject of the invention is a method(C) for the preparation of a compound of formula (III-PGXaaC$^{(pc)}$), with the compound of formula (III-PGXaaC$^{(pc)}$) being as defined above, also with all its preferred embodiments, method(C) comprises the consecutive steps a) and b), wherein
in step a) a protecting group PG2 is cleaved from a compound of formula (II-PG2)

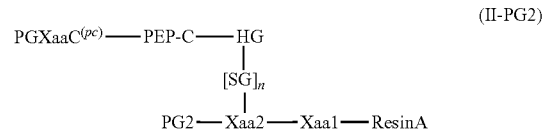

wherein in formula (II-PG2)
PGXaaC$^{(pc)}$, PGXaaC, pc, PEP-C, HG, n, SG, Xaa1 and Xaa2 have the same definition as above, also with all their preferred embodiments;
PG2 is an N-terminal protecting group conventionally used in peptide chemistry and is selected from the group consisting of basic cleavable type protecting groups, acid cleavable type protecting groups and reductively cleavable type protecting groups;
the alpha amino group of Xaa2 is protected by PG2, ResinA being a resin used conventionally as solid phase in SPPS;
the 1-carboxy group of Xaa1 is coupled to a functional group of ResinA;
to provide the compound of formula (II-H);

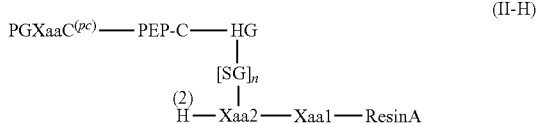

(II-H)

wherein in formula (II-H)
PGXaaC$^{(pc)}$, PGXaaC, pc, PEP-C, HG, n, SG, Xaa1, Xaa2 and ResinA have the same definition as above, also with all their preferred embodiments;
the hydrogen H denoted with (2) is a hydrogen of the unprotected alpha amino group of the amino acid residue Xaa2;
with the proviso, that PG2 is chosen to be of such a cleavable type protecting group, that PG2 can be cleaved from Xaa2 without cleaving PEP-C from HG;
and
in step b) the ResinA is cleaved from Xaa1 by an intra molecular ring formation reaction reaction(INRIFO) between the alpha amino group of Xaa2 and the carboxylic group of Xaa1 of compound of formula (II-H), reaction(INRIFO) forms a cyclic dipeptide of Xaa1 and Xaa2, to provide the compound of formula (III-PGXaaC$^{(pc)}$);
with the proviso, that the connection between ResinA and Xaa1 is chosen to be cleavable under such cleaving condition, that ResinA can be cleaved from Xaa1 by said reaction(INRIFO) without cleaving PEP-C from HG.

This means, that PG2 is chosen to be of such a cleavable type protecting group and HG is chosen to be cleavable under such cleaving condition different from those cleaving conditions needed to cleave PG2 from Xaa2, that PG2 can be cleaved from Xaa2 without cleaving PEP-C from HG;
and this means also,
that the connection between ResinA and Xaa1 is chosen, i.e. ResinA is chosen, to be cleavable under such cleaving condition, that ResinA can be cleaved from Xaa1 by reaction (INRIFO) without cleaving PEP-C from HG.

Preferably, if PEP-C carries side chain PGs, PG2 is chosen to be of such a cleavable type protecting group, that PG2 can be cleaved from Xaa2 without cleaving any side chain PGs from PEP-C.

Preferably, if PEP-C carries side chain PGs, the connection between ResinA and Xaa1 is chosen to be of such a cleavable type protecting group, that ResinA can be cleaved from Xaa1 by reaction(INRIFO) without cleaving any side chain PGs from PEP-C.

Compound of formula (II-PG2) is an embodiment of the above defined PEP-C-DKP-L-ResinA.

The dipeptide in e.g. formula (II-H) is one embodiment of the above mentioned DPR, which forms the DKP, i.e. the diketopiperazine residue.

PGXaaC$^{(pc)}$ and PG2 can be different protecting groups, which are cleaved under different reaction conditions; in this case, deprotection of the N-terminus of PEP-C and deprotection of Xaa2, i.e. method(B) and method(C) are done consecutively.

But preferably, PGXaaC$^{(pc)}$ and PG2 are identical or at least such different protecting groups, which are cleavable under the same reaction conditions; in this case, deprotection of the N-terminus of PEP-C and deprotection of Xaa2, i.e. cleavage of PGXaaC$^{(pc)}$ from the compound of formula (III-PGXaaC$^{(pc)}$), which is method(B), and cleavage of PG2 from the compound of formula (II-PG2), which is step (a) of method(C), can be done simultaneously in one step.

PG2 is, depending on its type, cleaved by strong, weak, basic or reductive cleaving conditions, these conditions being as defined above.

Preferably, PG2 is selected from the group consisting of Fmoc, Alloc, Boc, Trt, Mtt, Mmt and Ddz.
If PG2 is a strong type PG it is preferably Boc.
If PG2 is a weak type PG it is preferably Trt.
If PG2 is a reductive type PG it is preferably Alloc.
If PG2 is a basic type PG it is preferably Fmoc.

ResinA is a resin conventionally used as solid phase in SPPS and the bond between ResinA and Xaa1 can be cleaved under conditions, which do not cleave an amide bond between two amino acid residues of a peptide.

Preferably, ResinA is a resin with functional groups, which is conventionally used as solid support in SPPS, the functional groups being $NH_2$ or OH.

Preferably, ResinA is coupled to the 1-carboxylic acid group of Xaa1 by an ester or amide bond.

More preferably, ResinA is chosen to be such a resin, that ResinA is coupled to the Cl-atom of the carboxy group of Xaa1 by an ester or amide bond, neither of the bonds being cleavable under basic, weak or reductive cleaving conditions.

Preferably, ResinA is selected from the group consisting of hydroxymethylpolystyrene (HMPS) resins, polyethyleneglycol (PEG) based resins, resins, wherein PEG is grafted on a resin different from a PEG resin, polystyrene resin, p-benzyloxybenzyl alcohol resins, chloromethyl polystyrene-divinylbenzene resins, poly(vinyl alcohol)-graft-poly (ethylene glycol) (PVA-g-PEG) resins.

Resins, wherein PEG is grafted on a resin different from a PEG resin, are preferably PEG grafted on polystyrene resin, on p-benzyloxybenzyl alcohol resin or on chloromethyl polystyrene-divinylbenzene resin.

More preferably, ResinA is a HMPS resin or a chloromethyl polystyrene-divinylbenzene resin.

HydroxyChemMatrix® resins have a ChemMatrix® support, which is a polyethylene glycol (PEG) support, and are an example for polyethylene glycol based resins.

HydroxyTentagel® resins have a Tentagel® support, which is a grafted copolymer consisting of a low cross-linked polystyrene matrix on which polyethylene glycol (PEG) is grafted, and are an example for polystyrene based resins.

p-Benzyloxybenzyl alcohol resins are called Wang resins.
Chloromethyl polystyrene-divinylbenzene resin are called Merrifield resins.

Step (a) and step (b) may require different reaction condition, i.e. step (a) and step (b) can be done consecutively.

Preferably, step (a) and step (b) require the same reaction conditions, i.e. step (a) and step (b) are done simultaneously in one step.

Preferably, method(B), i.e. cleavage of PGXaaC$^{(pc)}$ from the compound of formula (III-PGXaaC$^{(pc)}$), step (a) of method(C), i.e. cleavage of PG2 from the compound of formula (II-PG2), and step (b) of method(C), i.e. the reaction(INRIFO), require the same reaction conditions and therefore can be done simultaneously in one step.

Preferably, step (b), the reaction(INRIFO), which cleaves Xaa1 from the ResinA, is done in a solvent (b).

Step (b) preferably is done at conditions, which afford for the alpha amino group of Xaa2 to be in a deprotonated state as an unprotonated amino group, i.e. not to be present as an ammonium ion.

More preferably, step (b) is done by the addition of at least one base (b).

If step (a) was done in acidic conditions, the pH is preferably neutralised by the addition of a base, preferably a tertiary base, more preferably the tertiary base is one of those used in HSPPS as mentioned above. To induce the reaction(INRIFO) of step (b), a base (b) is added, preferably the base (b) is a secondary amine, more preferably the conjugated acid of said secondary amine has a pKa value of from 5.0 to 15, more preferably of from 7.5 to 10. Said secondary amine is preferably a dialkylamine, more preferably it is selected from the group consisting of dimethylamine, di-n-propylamine, diethylamine, alpha-(p-tolyl)pyrroline, pyrrolidine, alpha-ethylpyrrolidine, alpha-benzylpyrrolidine, alpha-cyclohexylpyrrolidine, morpholine, piperidine, 2-methylpiperidine, N,N-dimethylhydroxylamine and N—$C_{1-4}$ alkylanilines, with the $C_{1-4}$ alkyl in the N—$C_{1-4}$ alkylanilines being linear or branched and selected from the group consisting of methyl, ethyl, n-propyl, iso-propyl, n-butyl and isobutyl, more preferably said $C_{1-4}$ alkyl being ethyl.

As solvent (b), any inert solvent, which can dissolve the reactants, may be used.

Preferably, solvent (b) is selected from the group consisting of dimethyl sulfoxide (DMSO), dioxane, tetrahydrofuran (THF), 1-methyl-2-pyrrolidone (NMP), N,N-dimethylformamide (DMF), N,N-dimethylacetamide (DMA), pyridine, dichloromethane (DCM), dichloroethane (DCE), chloroform, dioxane, tetrahydropyran, ethyl acetate, toluene, acetonitrile and mixtures thereof.

More preferably, solvent (b) is selected from the group consisting of NMP, DMF, THF and mixtures thereof.

Preferably, step (b) is done at a temperature of from 0 to 50° C., more preferably of from 5 to 30° C., even more preferably of from 15 to 25° C.

Preferably, step (b) is done at atmospheric pressure.

Preferably, the reaction time for step (b) is of from 1 min to 1 h, more preferably of from 1 min to 30 min, even more preferably of from 5 min to 15 min.

The term "part" in this description of step (b) is meant to be a factor of the parts by weight of the treated material, which is the compound of formula (II-H), if not otherwise stated.

Preferably, of from 5 to 20 parts, more preferably of from 5 to 15 parts of solvent are used.

Preferably, the amount of base (b) is of from 30 to 1% by weight, more preferably of from 15 to 2% by weight, even more preferably of from 10 to 5% by weight, with the % by weight being based on the total weight of the compound of formula (II-H).

Further subject of the invention is a method(D) for the preparation of a compound of formula (II-PG2), with the compound of formula (II-PG2) being as defined above, also with all its preferred embodiments, characterized by the sequential addition of the amino acids of PEP-C of compound of formula (II-PG2), except for the C-terminal amino acid of PEP-C, to a compound of formula (II-XaaC$^{(1)}$) by conventional solid phase peptide synthesis SPPS methodology, comprising the necessary and conventional steps of repetitive SPPS cycles such as deprotecting the N-terminus of the C-terminal amino acid attached to the resin, coupling the next amino acid, deprotecting, if more amino acids have to be coupled, the N-terminus of the thus coupled amino acid and so on, starting the SPPS with deprotecting the N-terminus of Xaa$^{(1)}$ and coupling of the amino acid of the second position from the C-terminus of PEP-C, said amino acid of the second position from the C-terminus of PEP-C having the formula PGXaaC$^{(2)}$-XaaC$^{(2)}$-OH; and, continuing the SPPS, in case that pc is 3 or greater, consecutively with any next amino acid of formula PGXaaC$^{(iippcc)}$-XaaC$^{(iippcc)}$-OH according to the sequence of PEP-C, with iippcc being an integer of from 3 to (pc-1); and ending the SPPS with the addition of the N-terminal amino acid of PEP-C, said N-terminal amino acid having the formula PGXaaC$^{(pc)}$-XaaC$^{(pc)}$-OH;

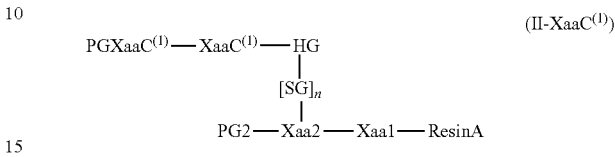

(II-XaaC$^{(1)}$)

wherein

PGXaaC$^{(pc)}$, PGXaaC, XaaC, pc, PEP-C, HG, n, SG, PG2, Xaa1, Xaa2 and ResinA have the same definition as above, also with all their preferred embodiments;

in PGXaaC$^{(1)}$, PGXaaC$^{(2)}$ and PGXaaC$^{(iippcc)}$, the indices (1), (2) and (iippcc) define the respective PGXaaC as the protecting group of the amino group of the respective amino acid residue XaaC of PEP-C;

in XaaC$^{(1)}$, XaaC$^{(2)}$ and XaaC$^{(iippcc)}$, the indices (1), (2) and (iippcc) define the respective XaaC as the respective amino acid residue XaaC of PEP-C;

with the proviso, that PGXaaC$^{(1)}$, PGXaaC$^{(2)}$ and any PGXaaC$^{(iippcc)}$ are protecting groups different from PG2 and that they are cleavable under reaction conditions different from those needed to cleave PG2 from Xaa2, and with the further proviso, that the reaction conditions used to cleave PGXaaC$^{(1)}$, the reaction conditions used to cleave the N-terminal protecting group PGXaaC$^{(2)}$ of said second amino acid and the reaction conditions used to cleave any N-terminal protecting group PGXaaC$^{(iippcc)}$ of said next amino acids, do not cleave PG2 from Xaa7;

and with the further proviso, that the bond between Xaa1 and ResinA is of such a type, that is it not cleaved during the SPPS.

Preferably, if any XaaC carries side chain PGs, any PGXaaC is chosen to be of such a cleavable type protecting group, that any PGXaaC can be cleaved from its amino acid XaaC without cleaving any side chain PGs from any side chain protected XaaC.

Therefore, PGXaaC$^{(1)}$ and PGXaaC$^{(2)}$ are identical or different and independently from each other N-terminal protecting groups conventionally used in SPPS and are the N-terminal protecting groups of the amino acids XaaC$^{(1)}$ and XaaC$^{(2)}$ of PEP-C respectively, to which the next amino acid of PEP-C is added by the SPPS, and are selected from the group consisting of basic cleavable type protecting groups, acid cleavable type protecting groups and reductively cleavable type protecting groups.

In the case, that pc is 2, then PEP-C is a dipeptidyl radical, and said amino acid of the second position from the C-terminus of PEP-C, having the formula PGXaaC$^{(2)}$-XaaC$^{(2)}$-OH, is identical with PGXaaC$^{(pc)}$-XaaC$^{(pc)}$-OH, and no said amino acid PGXaaC$^{(iippcc)}$-XaaC$^{(iippcc)}$-OH is used.

In stead of using only individual amino acids as building blocks, also oligopeptides, preferably di- or tripeptides, more preferably dipeptides, can be used as building blocks in SPPS. This is e.g. known, when pseudoproline is used as a side chain protecting group, in this case conventionally the respective dipeptide is used in SPPS as building block.

Preferably, PG2 is Fmoc or Alloc, and
PGXaaC$^{(1)}$, PGXaaC$^{(2)}$ and any PGXaaC$^{(iippcc)}$ are Boc.
In another preferred embodiment, PG2 is selected from the group consisting of Boc, Trt, Mtt, Mmt, Ddz and Alloc, and
PGXaaC$^{(1)}$, PGXaaC$^{(2)}$ and any PGXaaC$^{(iippcc)}$ are Fmoc.
More preferably, PG2 is Trt, Boc or Alloc, and
PGXaaC$^{(1)}$, PGXaaC$^{(2)}$ and any PGXaaC$^{(iippcc)}$ are Fmoc.
Even more preferably, PG2 is Trt or Alloc, and
PGXaaC$^{(1)}$, PGXaaC$^{(2)}$ and any PGXaaC$^{(iippcc)}$ are Fmoc.

Typical reaction conditions and parameters and reagents and standard protocols for SPPS are known in the art, e.g. Lloyd-Williams et al., "Chemical Approaches to the Synthesis of Peptides and Proteins", CRC Press, 1997, or Chan et al., "Fmoc solid phase peptide synthesis", Oxford University Press, 2000.

SPPS may be carried out by standard methods known in peptide chemistry. Usually, in SPPS the amino acids are added from the C-terminus to the N-terminus. Thus, the C-terminal amino acid or the peptide group proximal to the C terminus of a desired peptide fragment is the first to be added to the solid support, the resin. This occurs by reacting the carboxy group of the C-terminus to a complementary functional group on the resin support, the N-terminal amino group being usually protected by a protecting group in order to prevent undesired side reactions. In case that any amino acid or peptide group to be added has reactive groups on side chains, they are protected by protecting groups as well in order to avoid undesired side reactions. After coupling the first amino acid or peptide fragment to the solid support, the N-terminal protecting group is removed, and the next, N-terminally protected amino acid or peptide fragment is coupled to the first one. Then in successive cycles of removal of the N-terminal protecting group and coupling, the amino acids or peptide groups are consecutively attached to previously elongated peptidyl radical until the desired peptidyl radical is formed. The product of solid phase synthesis is thus a peptidyl radical bound to a solid support.

A wide variety of solid supports for SPPS are known. Preferably, the solid support comprises a resin that is made from one or more polymers, copolymers or combinations of polymers such as polyamide, polysulfamide, substituted polyethylenes, polyethyleneglycol, phenolic resins, polysaccharides, or polystyrene.

The solid support should be sufficiently insoluble and inert to solvents used in peptide synthesis.

The solid support typically includes a linking moiety having the functional group, to which the first amino acid or first peptide is initially coupled. The peptidyl radical is cleaved from the solid support under the appropriate reaction conditions to release the peptide from the support. Suitable solid supports can have linkers that are photo-cleavable, acid cleavable, preferably by TFA or HF, fluoride ion cleavable, reductively cleavable, preferably by Pd(0) catalysis; nucleophilically cleavable or cleavable by radicals. Preferably, the linking moiety of the solid support is chosen, that either the peptidyl radical is cleavable under such conditions that the side chain protecting groups of the peptide are not removed, or that the peptidyl radical is cleavable under such conditions that the side chain protecting groups of the peptide are simultaneously and completely removed as well.

Preferably, SPPS is done with an acid cleavable solid support, more preferably the linking moiety of the solid support comprises trityl groups, such as chlorinated trityl resins, preferably 2-chlorotrityl chloride (2-CTC) resin, or 4-methyltrityl chloride resins, 4-methoxytrityl chloride resins, 4-aminobutanl-ol 2-chlorotrityl resins, 4-aminomethylbenzoyl-2-chlorotrityl resins, 3-aminopropan-1-ol 2-chlorotrityl resins, bromoacetic acid 2-chlorotrityl resins, cyanoacetic acid 2-chlorotrityl resins, 4-cyanobenzoic acid 2-chlorotrityl resins, glicinol-2-chlorotrityl resins, propionic 2-chlorotrityl resins, ethyleneglycol-2-chlorotrityl resins, N-Fmoc hydroxylamine 2-chlorotrityl resins or hydrazine 2-chlorotrityl resins. Other preferred solid supports are polystyrene resins, or resins based on copolymers of styrene and divinylbenzene, having functional groups to bond the C-terminal carboxy group, preferably Wang resins, which comprise a copolymer of styrene and divinylbenzene with 4-hydroxymethylphenyloxymethyl anchoring groups, further resins such as 4-hydroxymethyl-3-methoxyphenoxybutyric acid resin.

Preferred resins are Wang, (2-CTC) and 4-hydroxymethyl-3-methoxyphenoxy butyric acid resins.

In order to prepare a resin for solid phase synthesis, the resin can be pre-washed with one or more suitable solvents.

As solvents, which are preferably used in SPPS, the preferred solvents mentioned above under HSPPS may also be used in SPPS. More preferred solvents are NMP, DMF, DCM mixtures thereof.

More preferred mixtures are DMF:DCM with a volume ratio of from 9:1 to 1:9, more preferred of from 4:1 to 1:4.

The SPPS preferably is done with any side chain of amino acids, which has a reactive functional group, being protected by side chain protecting groups in order to avoid undesired side reactions. The nature and use of side chain protecting groups is well known in the art.

The choice of a side chain-protecting group can depend on various factors, for example, type of synthesis performed, processing to which the peptide will be subjected, and the desired intermediate product or final product. The nature of the side chain protecting group also depends on the nature of the amino acid itself. Generally, a side chain protecting group is chosen that is not removed during deprotection of the alpha-amino groups during the solid phase synthesis. Therefore the protecting group of the alpha amino group and any side chain protecting group are typically not the same, preferably they represent an orthogonal system.

The term "orthogonal system" is defined in Baranay, G., and Merrifield, R. B., JACS, 1977, 99, 22, 7363-7365.

Examples of side chain protecting groups include acetyl (Ac), benzoyl (Bz), tert-butyl (tBu), triphenylmethyl (Trt), tetrahydropyranyl, benzyl ether (Bzl), 2,6-dichlorobenzyl ether (DCB), tert-butoxycarbonyl (Boc), 4-nitrobenzenesulfonyl (Ns), p-toluenesulfonyl (Tos), pentamethyldihydrobenzohran-5-sulfonyl (Pbf), 1,2-dimethyl¬indole-3-sulfonyl (MIS), adamantyloxycarbonyl, xanthyl (Xan), methyl ester, ethyl ester, tert-butyl ester (OtBu), benzyloxycarbonyl (Z), 2-chlorobenzyloxycarbonyl(2-Cl-Z), tert-amyloxycarbonyl (Aoc), aromatic or aliphatic urethane type protecting groups, photo labile groups such as nitro veratryloxycarbonyl (NVOC); and fluoride labile groups such as trimethylsilyloxycarbonyl (TEOC).

Preferred side chain groups are tBu, Trt, Boc, Tos, Pbf, OtBu and Z.

Preferably, functional groups containing amino acids commonly used with side chain protecting groups are Arg(Pbf), Asp(OtBu), Gln(Trt), Glu(OtBu), His(Trt), Lys(Boc), Ser (tBu), Thr(tBu), Trp(Boc) and Tyr(tBu), with Arg also sometimes used without side chain protecting group.

E.g. Fmoc-Arg(Pbf)-OH has formula (ARG-PBF).

(ARG-PBF)

An N-terminal protecting group is removed in a deprotection reaction prior to the addition of the next amino acid to be added to the growing peptide chain, but can be maintained when the peptide is cleaved from the support. The choice of an N-terminal protecting group can depend on various factors, for example, type of synthesis performed and the desired intermediate product or final product.

Examples of amino-terminal protecting groups include
(1) acyl-type protecting groups, such as formyl, acrylyl (Acr), benzoyl (Bz) and acetyl (Ac);
(2) aromatic urethane-type protecting groups, such as benzyloxycarbonyl Z and substituted Z, such as p-chlorobenzyloxycarbonyl, p nitrobenzyloxycarbonyl, p-bromobenzyloxycarbonyl, p-methoxybenzyloxycarbonyl;
(3) aliphatic protecting groups such as t-butyloxycarbonyl (Boc), 2-phenylpropyl (2)-oxycarbonyl (Poc), 2-(4-biphenylyl)-propyl (2) oxycarbonyl (Bpoc), diisopropylmethoxycarbonyl, isopropyloxycarbonyl, ethoxycarbonyl, allyloxycarbonyl (Alloc);
(4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl;
(5) thiourethantype protecting groups, such as phenylthiocarbonyl.

Preferred N-terminal protecting groups are Fmoc, Bpoc, Poc and Boc.

Fmoc or Fmoc-like chemistry is highly preferred for solid phase peptide synthesis, inasmuch as cleaving the resultant peptide in a protected state from the resin is relatively straightforward to carry out using mildly acidic cleaving agents. This kind of cleaving reaction is relatively clean in terms of resultant by-products, impurities, etc.

Furthermore, the Fmoc protecting group of the N-terminus fits well with the above mentioned side chain protecting groups in order to represent an orthogonal system.

Coupling in SPPS is usually done with a coupling reagent, preferably in the presence of a tertiary base, further preferably in the presence of a coupling additive, and further preferably the coupling reagent and any other compound is dissolved in a SPPS solvent as mentioned above.

The reaction conditions and reaction reagents for SPPS and for HSPPS are often similar.

Typical coupling reagents used in SPPS are phosphonium and uronium salts, mixed anhydrides, carbodiimides, other acylating agents such as activated esters or acid halogenides, and activated benzotriazinderivatives.

Phosphonium and uronium salts are preferably those used in HSPPS as mentioned above.

A mixed anhydride is for instance propane phosphonic acid anhydride (T3P).

Carbodiimide coupling reagents are preferably those used in HSPPS as mentioned above.

An activated esters is for instance isobutyl-chloroformiate (ICBF).

An activated benzotriazinderivatives is for instance 3-(diethoxyphosphoryloxy)-1,2,3-benzotriazin-4(3H)-one (DEPBT).

The tertiary base is preferably one of those used in HSPPS as mentioned above.

Coupling additives used in SPPS are those used in HSPPS as mentioned above.

The amount of the second and of the subsequent amino acids used is usually of from 1 to 3 mol equivalents relative to the loading factor achieved by the first coupling reaction on the resin support, preferably of from 1.3 to 3 mol equivalents, more preferably of from 1.5 to 3 mol equivalents.

Preferably, SPPS is done at a temperature of from 0 to 50° C., more preferably of from 5 to 30° C., even more preferably of from 15 to 25° C.

Preferably, SPPS is done at atmospheric pressure.

Preferably, the reaction time for SPPS is of from 15 min to 20 h, more preferably of from 30 min to 5 h, even more preferably of from 30 min to 2 h.

The term "part" in this description of reaction conditions of SPPS is meant to be a factor of the parts by weight of the solid support material, if not otherwise stated.

Preferably, of from 1 to 30 parts, more preferably of from 5 to 10 parts, of solvent are used.

Preferably, of from 0.9 to 5 mol equivalents, more preferably of from 1 to 1.5 mol equivalents, of coupling reagent is used, the mol equivalent being based on the mol of reactive carboxy groups, in case of SPPS of reactive C-terminal carboxy groups.

Preferably, of from 0.1 to 5 mol equivalents, more preferably of from 0.5 to 1.5 mol equivalents, of coupling additive is used, the mol equivalent being based on the mol of coupling reagent.

Preferably, of from 1 to 10 mol equivalents, more preferably of from 2 to 3 mol equivalents, of tertiary base is used, the mol equivalent being based on the mol of coupling reagent.

These SPPS conditions are general condition, which are applicable to coupling a carboxy group comprising building block to an amino group comprising reaction partner. In case of SPPS, the carboxy group comprising building block is the N-terminally protected amino acid which is to be coupled, and the amino group comprising reaction partner is the C-terminal amino acid or the growing peptide chain, which are connected to the support material.

This means, that the amount of carboxy group comprising building block used is usually of from 1 to 3 mol equivalents relative to mol of the amino group comprising reaction partner, preferably of from 1.3 to 3 mol equivalents, more preferably of from 1.5 to 3 mol equivalents.

Further subject of the invention is a method(E) for the preparation of a compound of formula (II-XaaC$^{(1)}$), with the compound of formula (II-XaaC$^{(1)}$) being as defined above, also with all its preferred embodiments, characterized by a coupling of an amino acid PGXaaC$^{(1)}$-XaaC$^{(1)}$-OH to a compound of formula (I-HG);

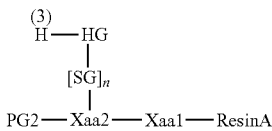
(I-HG)

wherein
the hydrogen denoted with (3) is a hydrogen of an unprotected functional group of HG;
PGXaa$^{(1)}$, XaaC$^{(1)}$, PGXaaC, XaaC, HG, n, SG, PG2, Xaa1, Xaa2 and ResinA have the same definition as above, also with all their preferred embodiments.

In case of formula (I-HG), the (*) in the any of the above definitions of HG now denotes in formula (I-HG) the bond between the hydrogen denoted with (3) and HG.

Method(E) is analogous to above defined step (i).

In case, that HG is a handle group selected from the group consisting of handle group of formula (HGF-I) in case that T1-1 is NH, handle group of formula (HGF-II), handle group of formula (HGF-III) and handle group of formula (HGF-VI),
the hydrogen denoted with (3) is connected to the terminal nitrogen of HG, and reaction conditions and parameters and reagents and standard protocols for the method(E) are preferably those which have been described above for the SPPS; with the carboxy group comprising building block being the amino acid PGXaaC$^{(1)}$-XaaC$^{(1)}$-OH, and the amino group comprising reaction partner being the compound of formula (I-HG), which are connected to the support material.

In case, that HG is a handle group selected from the group consisting of handle group of formula (HGF-I) in case that T1-1 is O, handle group of formula (HGF-IV) and handle group of formula (HGF-V),
the hydrogen denotes with (3) is connected to the terminal oxygen of HG, and
preferably, the coupling according to method(E) is done according to a method(E-OH) using in a solvent (E-OH), using one or more coupling reagents (E-OH), and is done preferably in the presence of one or more coupling additives (E-OH).

Preferable coupling reagents (E-OH) are carbodiimide coupling reagents (E-OH).

Carbodiimide coupling reagents (E-OH) are preferably selected from the group consisting of diisopropyl-carbodiimide (DIC), dicyclohexyl-carbodiimide (DCC) and water-soluble carbodiimides (WSCDI) such as 1-ethyl-3-(3-dimethylaminopropyl)-carbo-diimide (EDC)

Preferred coupling reagent (E-OH) is DIC.

A coupling additive (E-OH) is preferably DMAP or a nucleophilic hydroxy compound capable of forming activated esters, more preferably the nucleophilic hydroxy compound having an acidic, nucleophilic N-hydroxy function wherein N is imide or is N-acyl or N-aryl substituted triazeno, the triazeno type coupling additive being preferably a N-hydroxy-benzotriazol derivative (or 1-hydroxy-benzotriazol derivative) or a N-hydroxybenzotriazine derivative. Such coupling additives (E-OH) have been described in WO 94/07910 and EP 410 182. Since they also act as scavengers, they are also called scavengers.

Preferred coupling additives (E-OH) are selected from the group consisting of DMAP, N-hydroxy-succinimide (HOSu), 6-Chloro-1-hydroxy-benzotriazole (Cl-HOBt), N-hydroxy-3,4-dihydro-4-oxo-1,2,3-benzotriazine (HOOBt), 1-hydroxy-7-azabenzotriazole (HOAt), 1-hydroxy-benzotriazole (HOBt) and
ethyl 2-cyano-2-hydroxyimino-acetate (CHA).

CHA is available under tradename OXYMAPURE®. CHA has proved to be an effective scavenger as racemization is more suppressed compared to benzotriazole-based scavengers. In addition, CHA is less explosive than e.g. HOBt or Cl-HOBt, so that its handling is advantageous, and, as a further advantage, the coupling progress can be visually monitored by a colour change of the reaction mixture.

Preferably, DMAP is used as coupling additive (E-OH).

As solvent, any inert liquid solvent (E-OH) may be used.

Preferred solvents (E-OH) are selected from the group consisting of dimethyl sulfoxide (DMSO), dioxane, tetrahydrofuran (THF), 1-methyl-2-pyrrolidone (NMP), N,N-dimethylformamide (DMF), N,N-dimethylacetamide (DMA), pyridine, dichloromethane (DCM), dichloroethane (DCE), chloroform, dioxane, tetrahydropyran, ethyl acetate, toluene, acetonitrile and mixtures thereof.

More preferred solvents (E-OH) are NMP, DMF, DCM and mixtures thereof.

Preferably, the coupling according to method(E-OH) is done at a temperature of from 0 to 50° C., more preferably of from 5 to 30° C., even more preferably of from 15 to 25° C.

Preferably, the coupling according to method(E-OH) is done at atmospheric pressure.

Preferably, the reaction time for the coupling according to method(E-OH) is of from 15 min to 20 h, more preferably of from 30 min to 5 h, even more preferably of from 30 min to 2 h.

The term "part" in this description of reaction conditions of the coupling according to method(E-OH) is meant to be a factor of the parts by weight of the combined solid support material, if not otherwise stated.

Preferably, of from 1 to 30 parts, more preferably of from 5 to 10 parts, of solvent (E-OH) are used in the coupling according to method(E-OH).

Preferably, of from 0.1 to 5 mol equivalents, more preferably of from 1 to 1.5 mol equivalents, of coupling reagent (E-OH) is used in the coupling according to method(E-OH), the mol equivalent being based on the mol of reactive groups of HG.

Preferably, of from 0.1 to 5 mol equivalents, more preferably of from 0.5 to 1.5 mol equivalents, of coupling additive (E-OH) is used in the coupling according to method(E-OH), the mol equivalent being based on the mol of coupling reagent (E-OH).

In method(E) and method(E-OH) respectively, preferably of from 0.1 to 5 mol equivalents, more preferably of from 1 to 1.5 mol equivalents, of PGXaaC$^{(1)}$-XaaC$^{(1)}$-OH is used, the mol equivalent being based on the mol of reactive groups of HG.

Reactive groups of HG, which remain unreacted after the coupling of PGXaaC$^{(1)}$-XaaC$^{(1)}$-OH, are preferably capped, preferably the capping is done with acetic anhydride.

These conditions for method(E-OH) are general condition, which are applicable to coupling a carboxy group comprising building block to an OH or SH group comprising reaction partner. In case of method(E-OH), the carboxy group comprising building block is the amino acid PGXaaC$^{(1)}$-XaaC$^{(1)}$-OH, and the OH or SH group comprising reaction partner is the compound of formula (I-HG).

Further subject of the invention is a method(F) for the preparation of a compound of formula (I-HG), with the compound of formula (I-HG) being as defined above, also with all its preferred embodiments, method(F) comprises a step (F1A) for the case that n is 0; or method(F) comprises
a step (F3A) and a step (F3B) for the case that n is 1, with the step (F3B) being done after the step (F3A); or method(F) comprises
a step (F4);
with n as defined above, also with all its preferred embodiments;
wherein
step (F3A) comprises a coupling reaction (F3A-Coup) of a compound of formula (I-PG2),

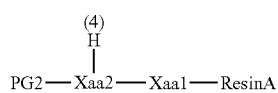

(I-PG2)

wherein
PG2, Xaa1, Xaa2 and ResinA have the same definition as above, also with all their preferred embodiments;
the H denoted with (4) is the hydrogen of FG, FG being as defined above, also with all it preferred embodiments as defined above;
with a compound SGroup;
the compound SGroup is a conventional building block used in peptide chemistry having two reactive functional groups SGroup-FunSiteN and SGroup-FunSiteC, the reactive functional group SGroup-FunSiteN is OH, SH or $NH_2$ and is used as a functionality resembling the alpha amino group of an amino acid building block in peptide synthesis and can be protected by a suitable protecting group PGSG, the reactive functional group SGroup-FunSiteC is used as a functionality resembling the carboxylic acid group of an amino acid building block in peptide synthesis;
PGSG is a protecting group conventionally used in peptide chemistry for protecting the alpha amino group of an amino acid or the N-terminus of a peptide, and is selected from the group consisting of basic cleavable type protecting groups, acid cleavable type protecting groups and reductively cleavable type protecting groups;
the compound SGroup is the precursor of SG, with SG being as defined above, also with all its preferred embodiments;
in case, that the reactive functional group SGroup-FunSiteN of compound SGroup is protected by a protecting group PGSG, than in a consecutive step (F-ConC) after step (F3A) PGSG is cleaved from SG;
with the proviso, that PGSG is different from PG2 and that PGSG is cleavable under reaction conditions different from those needed to cleave PG2 from Xaa2,
and with the further proviso, that the reaction conditions used to cleave PGSG do not cleave PG2 from Xaa;
and with the further proviso, that the reaction conditions used to cleave PGSG in a step (F-ConC) do not cleave Xaa 1 from ResinA;
providing a compound of formula (I-SG);

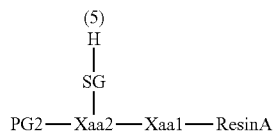

(I-SG)

-continued

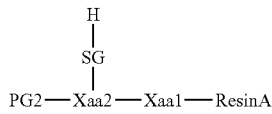

(I-SG)

wherein
SG, PG2, Xaa1, Xaa2 and ResinA have the same definition as above, also with all their preferred embodiments;
the H denoted with (5) is a hydrogen of the reactive functional group SGroup-FunSiteN;
step (F3B) is a coupling reaction (F3B-Coup) of the compound of formula (I-SG) with a compound HGroup;
the compound HGroup is a conventional building block used in peptide chemistry having two reactive functional groups HGroup-FunSiteN and HGroup-FunSiteC, the reactive functional group HGroup-FunSiteN is OH, SH or $NH_2$ and is used as a functionality resembling the alpha amino group of an amino acid building block in peptide synthesis and can be protected by a suitable protecting group PGHG, the reactive functional group HGroup-FunSiteC is used as a functionality resembling the carboxylic acid group of an amino acid building block in peptide synthesis;
PGHG is a protecting group conventionally used in peptide chemistry for protecting the alpha amino group of an amino acid or the N-terminus of a peptide, and is selected from the group consisting of basic cleavable type protecting groups, acid cleavable type protecting groups and reductively cleavable type protecting groups;
the compound HGroup is the precursor of HG, with HG being as defined above, also with all its preferred embodiments;
step (F1A) comprises a coupling reaction (F1A-Coup) of the compound of formula (I-PG2) with the compound HGroup, with the compound HGroup being as defined above, also with all its preferred embodiments;
in case, that the reactive functional group HGroup-FunSiteN of compound HGroup is protected by a protecting group PGHG, than in a consecutive step (F-ConA) after step (F3B) or after step (F1A), PGHG is cleaved from HG;
with the proviso, that PGHG is a protecting group different from PG2 and that PGHG is cleavable under reaction conditions different from those needed to cleave PG2 from Xaa2,
and with the further proviso, that the reaction conditions used to cleave PGHG do not cleave PG2 from Xaa2;
and with the further proviso, that the reaction conditions used to cleave PGHG in a step (F-ConA) do not cleave Xaa1 from ResinA;
the step (F4) comprises a coupling reaction of a compound of formula (pDKP) with a ResinA,

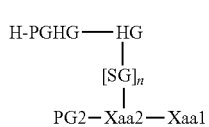

(pDKP)

wherein
HG, n, SG, PG2, Xaa1 and Xaa2 have the same definition as above, also with all their preferred embodiments;
with the ResinA having the same definition as above, also with all its preferred embodiments;
H-PGHG is hydrogen in case that the reactive functional group HGroup-FunSiteN is OH or SH;

H-PGHG is a protecting group PGHG in case that the reactive functional group HGroup-FunSiteN is NH₂;
with PGHG as defined above, also with all its preferred embodiments;
in case, that H-PGHG is PGHG, than in a consecutive step (F-ConB) after the reaction F4, PGHG is cleaved from HG;
with the proviso, that PGHG is different from PG2 and that PGHG is cleavable under reaction conditions different from those needed to cleave PG2 from Xaa2,
and with the further proviso, that the reaction conditions used to cleave PGHG do not cleave PG2 from Xaa2;
and with the further proviso, that the reaction conditions used to cleave PGHG in step (F-ConB) do not cleave Xaa1 from ResinA.

The compound of formula (pDKP) ends C-terminally with the free carboxylic acid group of Xaa1.

Compound HGroup is an embodiment of above mentioned HG used as building block in method(DKP-L-ResinA) or in method(DKP-L).

Compound SGroup is an embodiment of above mentioned SG used as building block in method(DKP-L-ResinA) or in method(DKP-L).

The compound of formula (DKP-L-ResinA-F) and the compound of formula (I-HG) are embodiments of above defined DKP-L-ResinA,

(DKP-L-ResinA-F)

with H-PGHG, HG, SG, n PG2, Xaa2, Xaa1 and ResinA being as defined above, also with all their preferred embodiments.

Compound of formula (DKP-L-ResinA-F) is the product of the reaction F1 or F3, optionally with the consecutive step (F-ConA) or (F-ConC), or of the reaction F4 optionally with the consecutive step (F-ConB).

The compound of formula (pDKP) is an embodiment of above defined DKP-L.

Compound of formula (I-PG2) and compound of formula (I-SG) are embodiments of intermediates of above defined method(DKP-L-ResinA).

In case of step (F3A) or in case of step (F1A), and FG being NH₂, the coupling reaction (F3A-Coup) or the coupling reaction (F1A-Coup) is preferably done under reaction conditions and parameters and reagents and protocols as described above for the SPPS, also with all the described preferred embodiments, with the mentioned carboxy group comprising building block being the compound SGroup or the compound HGroup respectively, and the amino group comprising reaction partner being the compound of formula (I-PG2).

In case of step (F3A) or in case of step (F1A), and FG being OH or SH, the coupling reaction (F3A-Coup) or the coupling reaction (F1A-Coup) is preferably done under the reaction conditions and parameters and reagents and protocols as described above for the method(E-OH), with the carboxy group comprising building block being the compound SGroup or the compound HGroup respectively, and the OH or SH group comprising reaction partner being the compound of formula (I-PG2).

In case of step (F3B) and the reactive functional group SGroup-FunSiteN being NH₂, the coupling reaction (F3B-Coup) is preferably done under reaction conditions and parameters and reagents and protocols as described above for the SPPS, also with all the described preferred embodiments, with the mentioned carboxy group comprising building block being the compound HGroup, and the amino group comprising reaction partner being the compound of formula (I-SG).

In case of step (F3B) and the reactive functional group SGroup-FunSiteN being OH or SH, the coupling reaction (F3B-Coup) is preferably done under the reaction conditions and parameters and reagents and protocols as described above for the method(E-OH), with the carboxy group comprising building block being the compound HGroup, and the OH or SH group comprising reaction partner being the compound of formula (I-SG).

In the compound of formula (pDKP), the carboxylic acid group of Xaa1 is unprotected. This unprotected carboxylic acid group of Xaa1 is reacted with an unprotected functional group of ResinA in the step (F4). Therefore, the coupling reaction in step (F4) is analogue to a conventional coupling reaction of an amino acid to a resin, i.e. the solid support. The coupling of an amino acid to a solid support is a known reaction, therefore the reaction conditions and parameters of the coupling reaction in step (F4) are known.

Preferably, if the functional group of ResinA, which is to be coupled to the carboxylic acid group of Xaa1 of compound of formula (pDKP), is a NH₂ group, the coupling reaction in step (F4) is preferably done under reaction conditions and parameters and reagents and protocols as described above for the SPPS, also with all the described preferred embodiments, with the mentioned carboxy group comprising building block being the compound of formula (pDKP), and the amino group comprising reaction partner being the ResinA.

Preferably, if the functional group of ResinA, which is to be coupled to the carboxylic acid group of Xaa1 of compound of formula (pDKP), is OH or SH, the coupling reaction in step (F4) is preferably done under the reaction conditions and parameters and reagents and protocols as described above for the method(E-OH), with the mentioned carboxy group comprising building block being the compound of formula (pDKP), and the OH or SH group comprising reaction partner being ResinA.

Preferably, PG2 is Fmoc or Alloc, and
a possible PGHG or PGSG is Boc.
In another preferred embodiment, PG2 is selected from the group consisting of Boc, Trt, Mtt, Mmt, Ddz and Alloc, and
a possible PGHG or PGSG is Fmoc.
More preferably, PG2 is Trt, Boc or Alloc, and
a possible PGHG or PGSG is Fmoc.
Even more preferably, PG2 is Trt or Alloc, and
a possible PGHG or PGSG is Fmoc.
Compound SGroup is the precursor of SG, with SG being as defined above, also with all its preferred embodiments, and has two reactive functional groups SGroup-FunSiteN and SGroup-FunSiteC, as explained above in the context of method(DKP-L-ResinA). The reactive functional group SGroup-FunSiteN preferably is OH or NH₂, more preferably NH₂. The reactive functional group SGroup-FunSiteN is present in the protected or coupled state as a connecting group CG-SG, CG-SG being —O—, —S— or —N(H)—. The reactive functional group SGroup-FunSiteC can be unprotected or can be preactivated and is the coupling site in the respective coupling reaction. Preferably, the reactive functional group SGroup-FunSiteC is a carboxylic acid group, if it is unprotected, or it is a preactivated carboxylic acid group. After this coupling reaction, any protecting group of the reactive functional group SGroup-FunSiteN is cleaved in order to make the reactive functional group SGroup-FunSiteN available for the next coupling reaction.

When the reactive functional group SGroup-FunSiteC a preactivated carboxylic acid group, the preactivation is preferably in a way as common in peptide chemistry. For example, reactivated carboxylic acid groups are used in form of their ester with N-hydroxysuccinimid or with penta flouro phenol.

Compound SGroup and SG respectively, can comprise ethylenoxid units of a defined and discrete number, or they can comprise a distribution of ethylene oxide units as is the case, when PEG chains are synthesized by polymerization of ethylene oxide without subsequent separation of the individual molecules of same chain length. In case of a distribution, compound SGroup, and thereby indirectly also SG, is specified rather by its average molecular weight and not by a discrete number of ethylene oxide units. Preferably, molecular weights of compound SGroup are from 1500 to 5000, preferably from 1500 to 4000, more preferably from 1500 to 3500.

Preferably, PGSG is Alloc, Fmoc, Mmt or Z.

Preferably, compound SGroup is a compound SGroup1, SGroup2, SGroup3, SGroup4, SGroup5, SGroup 6, SGroup7 or SGroup8;

compound SGroup1 is the compound of formula (SG-I), wherein Fmoc is connected via the bond denoted with (*) and OH is connected via the bond denoted with (**) in formula (SG-I), preferably m1 is 3;

compound SGroup2 is the compound of formula (SG-II), wherein Z, Fmoc or Alloc is connected via the bond denoted with (*) and OH is connected via the bond denoted with (**) in formula (SG-II), preferably m5 is 2;

compound SGroup3 is the compound of formula (SG-II), wherein Boc or Fmoc is connected via the bond denoted with (*) and OH is connected via the bond denoted with (**) in formula (SG-II), preferably m5 is 1;

compound SGroup4 is the compound of formula (SG-III), wherein Boc is connected via the bond denoted with (*) and OH is connected via the bond denoted with (**) in formula (SG-III), preferably m6 and m7 are 2;

compound SGroup5 is the compound of formula (SG-IV), wherein Mmt or Boc is connected via the bond denoted with (*) and OH is connected via the bond denoted with (**) in formula (SG-IV), preferably m9 is 4, 8, 12 or 27; especially the combination of Boc and m9 being 4, 8, 12 or 27; or the combination of Mmt and m9 being 4;

compound SGroup6 is the compound of formula (SG-V), wherein Boc or Fmoc is connected via the bond denoted with (*) and OH is connected via the bond denoted with (**) in formula (SG-V), preferably m10 is 1 or the molecular weight is 1500 to 3500, more preferably 3000; especially the combination Fmoc with m10 being 1, or the combination of Boc and the molecular weight being 1500 to 3500, more preferably 3000;

compound SGroup7 is the compound of formula (SG-VI), wherein Boc is connected via the bond denoted with (*) and Br is connected via the bond denoted with (**) in formula (SG-VI), preferably m11 is 3;

compound SGroup8 is the compound of formula (SG-VII), wherein Boc or Fmoc is connected via the bond denoted with (*) and OH or N-hydroxysuccinimid is connected via the bond denoted with (**) in formula (SG-VII), preferably the molecular weight is 1500 to 3500, more preferably 3000; and preferably Boc and OH or N-hydroxysuccinimid, or Fmoc and N-hydroxysuccinimid.

The OH connected via the bond denoted with (****) makes SGroup, the carboxylic acid group or the OH can also be used in its preactivated form, as outlined further above.

As an illustration, when compound SGroup is compound SGroup1 or SGroup2 with Alloc, then the compound of formula (I-SG) is the compound of formula (I-SGroup1-Fmoc) or (I-SGroup2-Alloc) respectively;

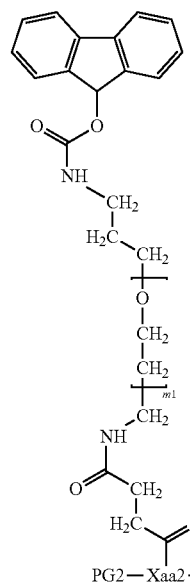

(I-SGroup1-Fmoc)

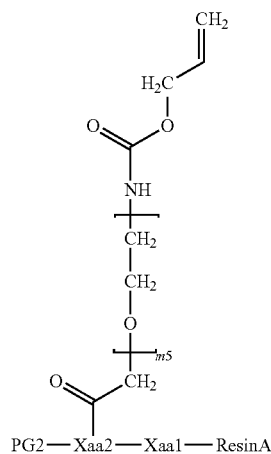

(I-SGroup2-Alloc)

wherein
m1, m5, PG2, Xaa1, Xaa2 and ResinA have the same definition as above, also with all their preferred embodiments.

The compound HGroup is the precursor of HG, with HG being as defined above, also with all its preferred embodiments, and has two reactive functional groups HGroup-FunSiteN and HGroup-FunSiteC, as explained above in the context of method(DKP-L-ResinA). The reactive functional group HGroup-FunSiteN preferably is OH or $NH_2$, more preferably $NH_2$. The reactive functional group HGroup-FunSiteN is present in the protected or coupled state as a connecting group CG-HG, CG-HG being —O—, —S— or —N(H)—.

The reactive functional group HGroup-FunSiteC is usually unprotected and is the coupling site in the respective coupling reaction. Preferably, the reactive functional group HGroup-FunSiteC is a carboxylic acid group. After this coupling reaction, any protecting group of the reactive functional group HGroup-FunSiteN is cleaved in order to make the reactive functional group HGroup-FunSiteN available for the next coupling reaction.

Preferably, compound HGroup is selected from the group consisting of compound of formula (HGroupF-I), compound of formula (HGroupF-II), compound of formula (HGroupF-III), compound of formula (HGroupF-IV), compound of formula (HGroupF-V) and compound of formula (HGroupF-VI),

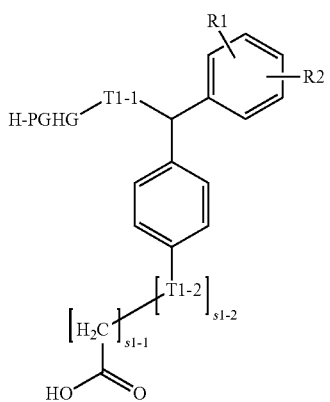
(HGroupF-I)

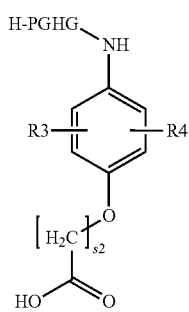
(HGroupF-II)

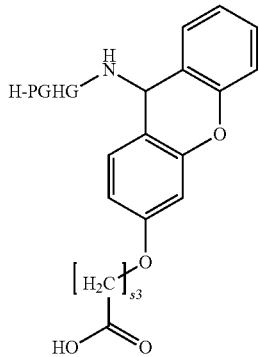
(HGroupF-III)

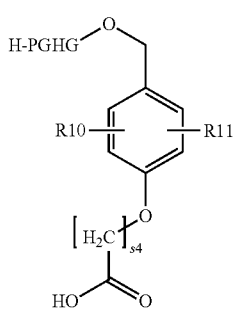
(HGroupF-IV)

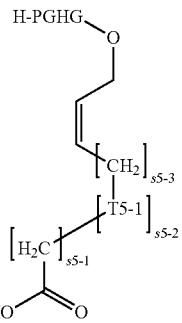
(HGroupF-V)

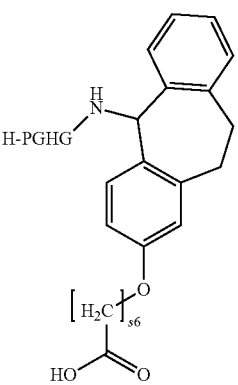
(HGroupF-VI)

wherein

R1, R2, R3, R4, R10 and R11 are as defined above, also with all their preferred embodiments, s1-1, s2, s3, s4 and s6 are as defined above, also with all their preferred embodiments, s5-1 is as defined above, also with all its preferred embodiments, s1-2, s5-2 and s5-3 are as defined above, also with all their preferred embodiments, T1-1 is as defined above, also with all its preferred embodiments, T1-2 and T5-1 are as defined above, also with all their preferred embodiments;

H-PGHG is hydrogen in case of compound HGroup being selected from the group consisting of compound of formula (HGroupF-I) in case that T1-1 is O, compound of formula (HGroupF-IV) and compound of formula (HGroupF-V);

H-PGHG is a protecting group PGHG in case of compound HGroup being selected from the group consisting of compound of formula (HGroupF-I) in case that T1-1 is NH, compound of formula (HGroupF-II), compound of formula (HGroupF-III) and compound of formula (HGroupF-VI).

Since the compound HGroup is derived from the HG, with HG being as defined above, also with all its preferred embodiments, the (*) in any of the above definitions of HG denoting, in case of compound HGroup, a bond between a HG and a hydrogen in case of HG being a handle group selected from the group consisting of handle group of formula (HGF-I) in case that T1-1 is O, handle group of formula (HGF-IV) and handle group of formula (HGF-V);

the (*) in any of the above definitions of HG denoting, in case of compound HGroup, a bond between a HG and a protecting group PGHG in case of HG being a handle group selected from the group consisting of handle group of formula (HGF-I) in case that T1-1 is NH, handle group of formula (HGF-II), handle group of formula (HGF-III) and handle group of formula (HGF-VI); and the (**) in any of the above definitions of HG denoting in case of compound HGroup a bond between HG and an OH.

This means, that in case, that the (*) in any of the above definitions of HG denotes, in case of compound HGroup, a bond between a HG and a protecting group PGHG, than the protecting PGHG is cleaved from HG after the coupling of compound HGroup.

Therefore, especially preferred compounds HGroup are derived from the group consisting of compound of formula (HG-Ia), compound of formula (HG-Ib), compound of formula (HG-Ic), compound of formula (HG-Id), compound of formula (HG-II), compound of formula (HG-III), compound of formula (HG-IVa), compound of formula (HG-IVb), compound of formula (HG-Va), compound of formula (HG-Vb) and compound of formula (HG-VI); with PGHG being as defined above, also with all its preferred embodiments.

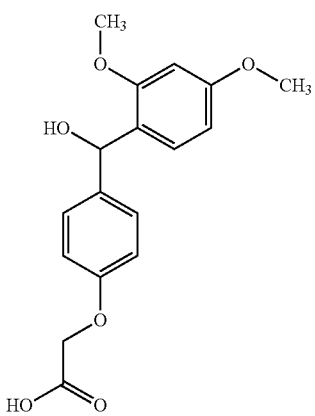
(HGroup-Id)

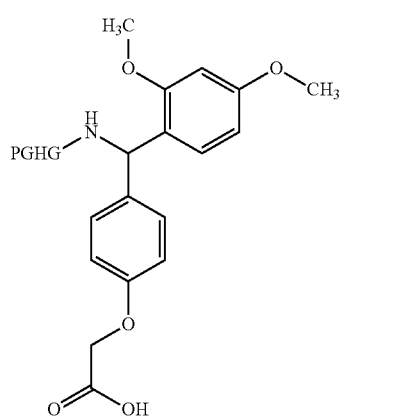
(HGroup-Ia)

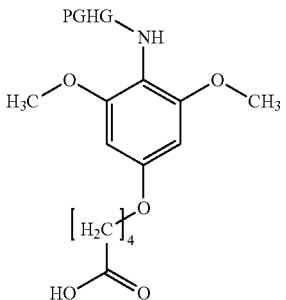
(HGroup-II)

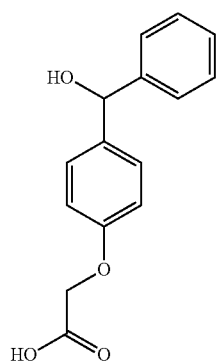
(HGroup-Ib)

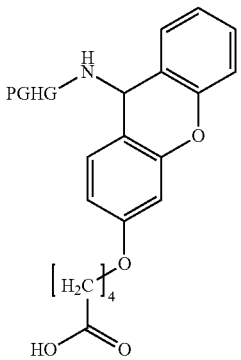
(HGroup-III)

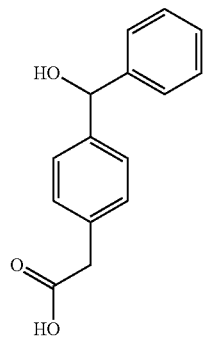
(HGroup-Ic)

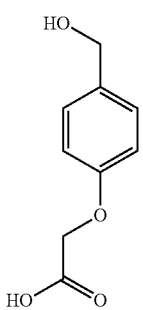
(HGroup-IVa)

-continued

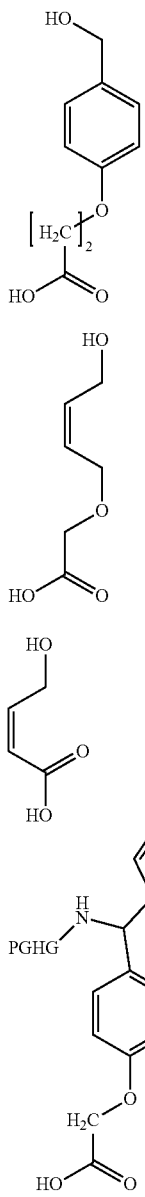

(HGroup-IVb)

(HGroup-Va)

(HGroup-Vb)

(HGroup-VI)

The protection group of the side chain of Xaa2 residue is different from PG2 and is cleavable under conditions different from those needed to cleave PG2 from Xaa2, and different from those needed to cleave Xaa1 from ResinA.

Further subject of the invention is a method(G) for the preparation of a compound of formula (pDKP), with the compound of formula (pDKP) being as defined above, also with all its preferred embodiments, characterized by a cleaving reaction (pDKP-Cleav) of a protecting group CPG from a compound of formula (pDKP-CPG);

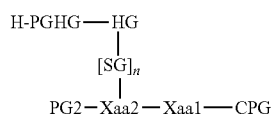

(pDKP-CPG)

wherein
H-PGHG, HG, n, SG, PG2, Xaa1 and Xaa2 have the same definition as above, also with all their preferred embodiments;
CPG is protecting group conventionally used in peptide chemistry for protecting the carboxylic acid group of an amino acid or of the C-terminus of a peptide, and is selected from the group consisting of basic cleavable type protecting groups, acid cleavable type protecting groups and reductively cleavable type protecting groups;
with the proviso, that the protecting group CPG is a protecting group different from PG2 and that CPG is cleavable under reaction conditions different from those needed to cleave PG2 from Xaa2,
and with the proviso, that the reaction conditions used to cleave the protecting group CPG do not cleave PG2 from Xaa2;
and in case, that H-PGHG is a protecting group PGHG, than with the proviso, that the protecting group CPG is a protecting group different from PGHG and that CPG is cleavable under reaction conditions different from those needed to cleave PGHG from HG,
and with the proviso, that the reaction conditions used to cleave the protecting group CPG do not cleave PGHG from HG.
CPG is an embodiment of C-PG.
Compound of formula (pDKP-CPG) is an embodiment of above defined DKP-L.
Preferably, CPG is selected from the group consisting of allyl ester, Bzl (benzyl, also abbreviated with Bn) ester, Fm (9-fluorenylmethyl) ester, Me (methyl) ester, Et (ethyl) ester, Trt (triphenylmethyl or trityl or Tr) ester, tBu ester and SiEt$_3$ (triethylsilyl ester or TES).
Preferably, in case of protecting group CPG being a basic cleavable type protecting group, the protecting group CPG is selected from the group consisting of Fm, Me and Et;
in case of protecting group CPG being an acid cleavable type protecting group, the protecting group CPG is selected from the group consisting of Trt, tBu and SiEt$_3$;
and in case of protecting group CPG being a reductively cleavable type protecting group, the protecting group CPG is selected from the group consisting of allyl and Bzl.
More preferably, CPG is Trt or Bzl.
Preferably, PG2 is Fmoc and
CPG is allyl;
preferably, a possible PGHG is Boc.
In another preferred embodiment, PG2 is Alloc and
CPG is Fmoc;
preferably, a possible PGHG is selected from the group consisting of tBu, Trt, Mtt, Mmt and Ddz.
In another preferred embodiment, PG2 is selected from the group consisting of tBu, Trt, Cl-Trt, Mtt, Mmt and Ddz; and
CPG is Allyl;
preferably, a possible PGHG is Fmoc.
More preferably, PG2 is Trt and
CPG is Allyl;
preferably, a possible PGHG is Fmoc.
Further subject of the invention is a method(H) for the preparation of a compound of formula (pDKP-CPG), with the compound of formula (pDKP-CPG) being as defined above, also with all its preferred embodiments, method(H) comprises
a step (H1A) for the case that n is 0; or method(H) comprises a step (H3A) and a step (H3B) for the case that n is 1, with the step (H3B) being done after the step (H3A);
with n as defined above, also with all its preferred embodiments;

wherein
step (H3A) is a coupling reaction (H3A-Coup) of a compound of formula (pDKP-PG2),

(pDKP-PG2)

wherein
PG2, Xaa1, Xaa2 and CPG have the same definition as above, also with all their preferred embodiments;
the H denoted with (6) is the hydrogen of FG, FG being as defined above, also with all it preferred embodiments as defined above;
with a compound SGroup, the compound SGroup being as defined above, also with all its preferred embodiments;
in case, that the reactive functional group SGroup-FunSiteN of compound SGroup is protected by a protecting group PGSG, than in a consecutive step (H-ConC) after step (H3A) the protecting PGSG is cleaved from SG;
with the proviso, that the protecting group PGSG is a protecting group different from PG2 and that PGSG is cleavable under reaction conditions different from those needed to cleave PG2 from Xaa2,
and with the further proviso, that the reaction conditions used to cleave the protecting group PGSG do not cleave PG2 from Xaa7;
and with the further proviso, that the reaction conditions used to cleave the protecting group PGSG in a step (H-ConC) do not cleave Xaa1 from ResinA;
providing a compound of formula (pDKP-SG);

(pDKP-SG)

wherein
SG, PG2, Xaa1, Xaa2 and CPG have the same definition as above, also with all their preferred embodiments;
the H denoted with (7) is a hydrogen of the reactive functional group SGroup-FunSiteN;
step (H3B) is a coupling reaction (H3B-Coup) of the compound of formula (pDKP-SG) with a compound HGroup, with the compound HGroup being as defined above, also with all its preferred embodiments;
step (H1A) is a coupling reaction (H1A-Coup) of the compound of formula (pDKP-PG2) with the compound HGroup, with the compound HGroup being as defined above, also with all its preferred embodiments;
in case, that the reactive functional group HGroup-FunSiteN of compound HGroup is protected by a protecting group PGHG, than in a consecutive step (H-ConA) after step (H3B) or after step (H1A), the protecting PGHG is cleaved from HG;
with the proviso, that the protecting group PGHG is a protecting group different from PG2 and that PGHG is cleavable under reaction conditions different from those needed to cleave PG2 from Xaa2;
and with the further proviso, that the reaction conditions used to cleave the protecting group PGHG do not cleave PG2 from Xaa7;
and with the further proviso, that the reaction conditions used to cleave the protecting group PGHG in a step (H-ConA) do not cleave Xaa1 from ResinA.

Method(H) is comprised in above defined method(DKP-L).
Compound of formula (pDKP-PG2) and compound of formula (pDKP-SG) are embodiments of intermediates of above defined method(DKP-L).
The protection group of the side chain of Xaa2 residue is different from PG2 and is cleavable under conditions different from those needed to cleave PG2 from Xaa7, and different from those needed to cleave CPG from Xaa1.
Preferably, the above defined methods are done consecutively, method(B) is done after method(C), method(C) is done after method(D), method(D) is done after method(E) and method(E) is done after method(F); a method(G) is optionally done before method(F) and a method(H) before a method(G); and the above defined respective compounds are in this case intermediates in this sequence of methods for the preparation of compound of formula (III-H).
Further subject of the invention are following methods:
1. a method(A), wherein
   the compound of formula (III-H) has been prepared by the method(B);
2. a method(A), wherein
   the compound of formula (III-H) has been prepared by the method(B); and wherein
   the compound of formula (III-PGXaaC$^{(pc)}$) of method(B) has been prepared by method(C);
3. a method(A), wherein
   the compound of formula (III-H) has been prepared by the method(B); and wherein
   the compound of formula (III-PGXaaC$^{(pc)}$) of method(B) has been prepared by method(C); and wherein
   the compound of formula (II-PG2) of method(C) has been prepared by method(D);
4. a method(A), wherein
   the compound of formula (III-H) has been prepared by the method(B); and wherein the compound of formula (III-PGXaaC$^{(pc)}$) of method(B) has been prepared by method(C); and wherein
   the compound of formula (II-PG2) of method(C) has been prepared by method(D); and wherein
   the compound of formula (II-XaaC$^{(1)}$) of method(D) has been prepared by method(E);
5. a method(A), wherein
   the compound of formula (III-H) has been prepared by the method(B); and wherein
   the compound of formula (III-PGXaaC$^{(pc)}$) of method(B) has been prepared by method(C); and wherein
   the compound of formula (II-PG2) of method(C) has been prepared by method(D); and wherein
   the compound of formula (II-XaaC$^{(1)}$) of method(D) has been prepared by method(E); and wherein
   the compound of formula (I-HG) of method(E) has been prepared by method(F);
6. a method(A), wherein
   the compound of formula (III-H) has been prepared by the method(B); and wherein
   the compound of formula (III-PGXaaC$^{(pc)}$) of method(B) has been prepared by method(C); and wherein
   the compound of formula (II-PG2) of method(C) has been prepared by method(D); and wherein
   the compound of formula (II-XaaC$^{(1)}$) of method(D) has been prepared by method(E); and wherein
   the compound of formula (I-HG) of method(E) has been prepared by method(F); and wherein the compound of formula (pDKP) of method(F) has been prepared by method(G);

7. a method(A), wherein
the compound of formula (III-H) has been prepared by the method(B); and wherein
the compound of formula (III-PGXaaC$^{(pc)}$) of method(B) has been prepared by method(C); and wherein
the compound of formula (II-PG2) of method(C) has been prepared by method(D); and wherein
the compound of formula (II-XaaC$^{(1)}$) of method(D) has been prepared by method(E); and wherein
the compound of formula (I-HG) of method(E) has been prepared by method(F); and wherein
the compound of formula (pDKP) of method(F) has been prepared by method(G); and wherein
the compound of formula (pDKP-CPG) of method(G) has been prepared by method(H).

Method(A) is an embodiment of step (ii-pep) of method(PEP-HSPPS).
Method(B) is preferably comprised in method(C-PEP).
Step (b) of method(C) is an embodiment of step (iii) of method(C-PEP).
Step (a) of method(C) is comprised in a preferred embodiment of step (iii) of method(C-PEP).
Method(D) is an embodiment of step (ii) of method(C-PEP).
Method(E) is an embodiment of step (i) of method(C-PEP).
Step (F4) of method(F) is an embodiment of method(X2).
Step (F3A) of method(F) is an embodiment of the step (X1-iii) of method(X1).
Step (F3B) of method(F) is an embodiment of the step (X1-iv) of method(X1).
Step (F1A) of method(F) is an embodiment of the step (X1-iv) of method(X1).
Method(G) is an embodiment of method(DKP-L).
If step (DKP-L-i), optional step (DKP-L-ii) and the step (DKP-L-iii) of method(DKP-L) are done consecutively, then step (H1) of method(H) is an embodiment of step (DKP-L-i), and steps (H3A) and (H3B) of method(H) are embodiments of steps (DKP-L-ii) and (DKP-L-iii).

Therefore further subject of the invention are following methods:
(a) a method(PEP-HSPPS), wherein step (ii-pep) is method (A);
(b) a method(C-PEP) comprising method(B);
(c) a method(C-PEP), wherein step (iii) comprises step (b) of method(C);
(d) a method(C-PEP), wherein step (iii) comprises step (a) of method(C);
(e) a method(C-PEP), wherein step (ii) comprises method (D);
(f) a method(C-PEP), wherein step (i) comprises method(E);
(g) a method(DKP-L-ResinA), wherein method(X2) comprises step (F4) of method(F);
(h) a method(DKP-L-ResinA), wherein step (X1-iii) of method(X1) comprises step (F3A) of method(F);
(i) a method(DKP-L-ResinA), wherein step (X1-iv) of method(X1) comprises step (F3B) of method(F);
(j) a method(DKP-L-ResinA), wherein step (X1-iv) of method(X1) comprises step (F1A) of method(F);
(k) a method(DKP-L) comprising method(G);
(l) a method(DKP-L), wherein the step (DKP-L-i), the optional step (DKP-L-ii) and the step (DKP-L-iii) are done consecutively, and wherein step (DKP-L-i) comprises step (H1) of method(H), and steps (DKP-L-ii) and (DKP-L-iii) comprise the steps (H3A) and (H3B) of method(H).

Further subject of the invention is compound of formula (III-H), compound of formula (III-PGXaaC$^{(pc)}$), compound of formula (II-PG2), compound of formula (II-H), compound of formula (II-XaaC$^{(1)}$), compound of formula (I-HG), compound of formula (I-SG), compound of formula (pDKP), compound of formula (pDKP-CPG) and compound of formula (pDKP-SG);
with the compound of formula (III-H), the compound of formula (III-PGXaaC$^{(pc)}$), the compound of formula (II-PG2), the compound of formula (II-H), the compound of formula (II-XaaC$^{(1)}$), the compound of formula (I-HG), the compound of formula (I-SG), the compound of formula (pDKP), the compound of formula (pDKP-CPG) and the compound of formula (pDKP-SG) as defined above, also with all their preferred embodiments.

Compound of formula (I-HG) is one embodiment of DKP-L-ResinA.

The compounds of formula (I-PG2) are known compounds and can be prepared by conventional SPPS with subsequent deprotection of the side chain of the Xaa2 residue.

The compounds of formula (pDKP-PG2) are known compounds and can be prepared by conventional coupling of an N-terminally and side chain protected amino acid PG2-Xaa2 with a C-terminally protected amino acid Xaa1-CPG, and with subsequent deprotection of the side chain of the Xaa2 residue.

Further subject of the invention are
(u1) the use of a compound selected from the group consisting of compound of formula (III-H), compound of formula (III-PGXaaC$^{(pc)}$), compound of formula (II-PG2), compound of formula (II-H), compound of formula (II-XaaC$^{(1)}$), compound of formula (I-HG), compound of formula (I-SG), compound of formula (pDKP), compound of formula (pDKP-CPG) and compound of formula (pDKP-SG); or the use of compound of formula (pDKP) or of compound of formula (pDKP-CPG) as a DKP-PG forming linker;
in peptide chemistry;
for the preparation of a peptide; or
in a method for the preparation of a peptide; or
in a step of a method for the preparation of a peptide; or
in a peptide coupling reaction; or
in SPPS for the preparation of a peptide; or
in HSPPS for the preparation of a peptide;
(u2) the use of a compound of formula (III-PGXaaC$^{(pc)}$) for the preparation of a compound of formula (III-H);
(u3) the use of a compound of formula (II-PG2) for the preparation of a compound of formula (II-H) or of a compound of formula (III-PGXaaC$^{(pc)}$);
(u4) the use of a compound of formula (II-H) for the preparation of a compound of formula (III-PGXaaC$^{(pc)}$);
(u5) the use of a compound of formula (II-XaaC$^{(1)}$) for the preparation of a compound of formula (III-PGXaaC$^{(pc)}$);
(u6) the use of a compound of formula (I-HG) for the preparation of a compound of formula (II-XaaC$^{(1)}$);
(u7) the use of a compound of formula (I-SG) for the preparation of a compound of formula (I-HG);
(u8) the use of compound of formula (pDKP) for the preparation of a compound of formula (I-HG);
(u9) the use of a compound of formula (pDKP-CPG) for the preparation of a compound of formula (pDKP);
(u9) the use of a compound of formula (pDKP-SG) for the preparation of a compound of formula (pDKP-CPG).
(u10) the use of a compound of formula (pDKP-PG2) for the preparation of a compound of formula (pDKP-SG) or for the preparation of a compound of formula (pDKP-CPG).
(u11) the use of a compound of formula (I-PG2) for the preparation of a compound of formula (I-SG) or for the preparation of a compound of formula (I-HG);

(u12) the use of a compound selected from the group consisting of compound of formula (III-PGXaaC$^{(pc)}$), compound of formula (II-PG2), compound of formula (II-H), compound of formula (II-XaaC$^{(1)}$), compound of formula (I-HG), compound of formula (I-SG), compound of formula (pDKP), compound of formula (pDKP-CPG) and compound of formula (pDKP-SG), for or in the preparation of compound of formula (III-H);

(u13) the use of the residue DKP-PG or the residue of formula (III-res) as a protecting group, preferably as a protecting group in peptide chemistry, preferably as a C-terminal protecting group.

with these compounds and residues as defined above, also with all their preferred embodiments.

The present invention allows cleavage of the C-terminal fragment of the desired peptide from the supporting resin after its preparation with SPPS and its C-terminal protection in one single step, and this provides in comparison to the conventional two step procedure, i.e. firstly cleavage from supporting resin and secondly protecting of the C-terminus, for higher yield due to more complete reaction and/or less undesired side-reactions, no need for additional process step, reaction time, reagents and equipment, i.e. faster and more economic overall procedure, less solubility issues, as protected peptides are often not very well soluble in organic solvents, and less risk of epimerization of the peptide.

Also for hybrid synthesis of a peptide amide, the invention provides for a method of preparation the C-terminal fragment, which omits a multi step approach such as first preparing the C-terminal fragment starting with the amino acid of position 2 from the C-terminus and addition of the amino acid in position 1 from the C-terminus in separate steps. The method avoids partial loss of side chain protecting groups, avoids the risk of epimerization of the peptide due to the coupling of the amino carboxamide, it needs less process steps, time, reagents and equipment, and the method thereby has a higher yield due to more complete reaction, less process steps and less undesired side-reactions.

Further advantage of the invention is the use of Rink amide handle in HSHSPPS. Usually, when cleaving a peptide after SPPS from a Rink amide handle modified resin, total deprotection of the side chains of the peptide occurs simultaneously, thereby the Rink amide handle is usually not used in HSHSPPS. Due to the invention, the Rink amide handle remains in the C-terminal DKP linker group, thereby making the peptide fragment usable as C-terminal fragment in HSPPS, and the Rink amide handle comprising C-terminal linker group is finally cleaved together with the side chain protecting groups in the final step providing the target peptide.

Another advantage of the method of the invention is the possibility to produce side chain protected fragments C-PEP to be used in HSPPS, which have an amide as C-terminus. Such peptides are usually prepared using the Sieber Amide resin comprising the Sieber handle. Specific cleavage conditions in case of the use of the Sieber Amide resin are necessary to cleave the peptide from the resin without side chain deprotection, whereas common cleavage condition lead also in case of the Sieber Amide resin to at least partial deprotection of some of the side chains. When using the method of the invention for the preparation of a fragment C-PEP having an amide at its C-terminus, the applicability of Sieber handle is broadened, since the Sieber handle is used as the handle group HG in the linker and the cleavage of the peptide from the handle group of the linker is postponed to the very last step in HSH-SPPS and can be done under global deprotection conditions, whereas the necessary cleavage from the resin providing the DKP linker group comprising peptide fragment used as C-terminal fragment in HSPPS is done under conditions different from those which would cleave side chain protecting groups, and these conditions used to cleave the linker from the resin by simultaneous generation of the DKP linker group do not lead to the cleavage of the peptide from the Sieber handle moiety nor to side chain deprotection. This broadens the scope of use of the Sieber handle with respect to side chain protected peptide fragment synthesis without necessitating specific cleavage conditions.

In case of Xaa1 being a compound of formula (HypX), the solubility of the peptidyl fragment comprising the DKP linker group can be greatly enhanced by using a solubility enhancing substituent of formula (Sub-R8) for R8, and therefore the HSPPS with C-terminal fragments with long amino acid chains becomes possible, which is necessary, if target peptides having many amino acid residues are to be synthesized from many fragments, and the first C-terminal fragment comprising the DKP linker group is consecutively coupled to the successive PEP-N fragments by repetitive HSPPS.

Furthermore, the possibility of using a spacer group SG can provide for higher solubility of the fragment C-PEP in HSPPS, and therefore the HSPPS with C-terminal fragments with long amino acid chains becomes possible, which is necessary, if target peptides having many amino acid residues are to be synthesized from many fragments, and the first C-terminal fragment comprising the DKP linker group is consecutively coupled to the successive PEP-N fragments by repetitive HSPPS.

Furthermore, the spacer group SG removes spatially the reaction centre, which is the N-terminus to which the amino acids building blocks are sequentially coupled, during SPPS away from the solid support, thereby the accessibility of the reaction centre for the dissolved reagents, additives, amino acids building blocks and so on is greatly improved.

EXAMPLES

Abbreviations and Raw Materials

The following abbreviations and raw materials have been and are used in the following, if not otherwise stated.

| | |
|---|---|
| Ac | acetyl |
| ACN | acetonitrile |
| CTC resin | 2-chlorotrityl chloride resin (beads, 100 to 200 mesh (the mesh is measured according to American Society for Testing and Materials international, ASTM international), 1.57 mmol/g, "mmol/g" means "mmol active sites/g resin") |
| DBF-Adduct | 1-(9H-fluoren-9-ylmethyl)piperidine |
| DCM | dichloromethane |
| DIEA | diisopropylethylamine |
| DIPE | diisopropyl ether |
| DIPCDI | N,N'-diisopropylcarbodiimide |
| DMAP | 4-dimethylaminopyridin |
| DMB | 1,3-dimethoxybenzene |
| DMF | N,N-dimethylformamide |
| eq | equivalent(s) eq refers to the mol-equivalents, with regard to the mol of reactive sites of the resin, if not mentioned otherwise |
| Fmoc-Rink-OH | 4'-{(R,S)-alpha-[1-(9-Fluorenyl)methoxycarbonylamino]-2,4-dimethoxybenzyl}-phenoxyacetic acid, also called p-{(R,S)-a-[1-(9H-Fluoren-9-yl)-methoxyformamido]-2,4-dimethoxybenzyl}-phenoxyacetic acid, also called Fmoc-Rink amide handle Fmoc-Rink-OH is the handle group of formula (HG-Ia), wherein the bond denoted with |

| | |
|---|---|
| | (*) is connected to the 9-Fluorenylmethyloxycarbonyl group of Fmoc and the bond denoted with (**) to OH. Fmoc-Rink-OH is the compound of formula (HGroup-Ia) with PGHG being Fmoc. |
| Fmoc-Ramage-OH | [R,S]-2-{[5-(9-Fluorenylmethyloxycarbonylamino)-dibenzo[a,d]cycloheptane-2-yl]oxy}-acetic acid, also called Fmoc-Suberol, CAS 212783-75-0, also called Fmoc-Ramage handle Fmoc-Ramage-OH is the handle group of formula (HG-VI), wherein the bond denoted with (*) is connected to the 9-Fluorenylmethyloxycarbonyl of Fmoc and the bond denoted with (**) to OH. Fmoc-Ramage-OH is the compound of formula (HGroup-VI) with PGHG being Fmoc. |
| Fmoc-TTDS-OH | [N-1[9-Fluorenylmethoxycarbonyl]-1,13-diamino-4,7,10-trioxatridecan-succinamic acid, CAS 172089-14-4 TTDS is the spacer group of formula (SG-I) wherein m1 is 3. Fmoc-TTDS-OH is the compound SGroup1 wherein m1 is 3. |
| HMPA | 4-hydroxymethylphenoxyacetic acid, CAS 68858-21-9 HMPA is the handle group of formula (HG-IVa), wherein the bonds denoted with (*) and (**) are connected to OH. HMPA is the compound of formula (HGroup-IVa). |
| HCTU | 2-(6-chloro-1H-benzotriazole-1-yl)-1,1,3,3-tetramethylaminium hexafluorophosphate |
| HMPS resin | hydroxymethylpolystyrene resin (beads, of from 100 to 200 mesh (the mesh is measured according to American Society for Testing and Materials international, ASTM international), 0.98 mmol/g, "mmol/g" means "mmol active sites/g resin") |
| HOBt | 1-hydroxybenzotriazole. water content ca. 12% (w/w) |
| min | minute(s) |
| MW | molecular weight |
| Oxyma | ethyl 2-cyano-2-(hydroxyimino)acetate |
| PVDF | polyvinylidene fluoride |
| RP-HPLC | reverse phase high-performance liquid chromatography |
| RP-HPLC-ESMS | reverse phase high-performance liquid chromatography electrospray mass spectrometry |
| resin loading | mmol of peptide per g of resin |
| RT | room temperature |
| s | second(s) |

Sequence Abbreviations:

| | |
|---|---|
| T20 | Ac[T20-1-36]NH$_2$. This sequence is registered under CAS 159519-65-0. |
| T20C | H[T20-27-36]NH$_2$ |
| BocT20N | Boc[T20-17-26]OH |
| HT20N | H[T20-17-26]OH |
| HT20F | H[T20-17-36]NH$_2$ |
| TIS | triisopropylsilane |
| UV | ultraviolet |

The sequence listing links the abbreviations of the sequences to the sequences.

E.g., [T20-1-36] is the sequence of the T20 peptide consisting of the amino acid residues 1 to 36, with the left number representing the N-terminal amino acid residue and the right number representing the C-terminal amino acid residue.

Methods Description

A) Determination of Resin Loading

The resin loading was quantified by Fmoc group determination measuring the UV absorbance at 290 nm. UV absorbance measures were carried out on a Shimadzu UV-Vis recording spectrophotometer (UV-2501 PC).

Step1 Collect the Solution from Fmoc Group Deprotection:

The Fmoc group was removed as described in the examples. In a $V_A$-ml glass volumetric flask A the resulting solutions from the Fmoc group deprotection were collected. The $V_A$-ml glass volumetric flask A was totally filled with DMF.

Step2 Diluted Solution for UV Measurements:

A $V_C$-ml aliquot from VA-ml glass volumetric flask A was transferred to another $V_B$-ml glass volumetric flask B and then it was totally filled with DMF. Three different diluted $V_B$-ml solutions were prepare and measured by UV spectroscopy at 290 nm to have representative absorbance values.

Step3 Quantification by UV Spectrophotometry:

A UV quartz cell of 1 cm path length was filled with DMF (reference solution), and placed into the spectrophotometer at 290 nm (maximum absorbance wavelength of dibenzofulvene) to obtain the zero. The UV cell was washed twice with the diluted solution B and then filled with this solution and its absorbance was measured at 290 nm.

Finally, the resin loading is calculated following the equation:

$$\frac{[A290 \times \text{cell length} \times V_A \times V_B]}{[epsilon290 \times \text{g of resin} \times V_C]}$$

A290: measured absorbance value
cell length: 1 (cm)
$V_A$: volume of the glass volumetric flask A (ml)
$V_B$: volume of the glass volumetric flask B (ml)
$V_C$: aliquot volume transferred from A to B (ml)
epsilon290: molar extinction coefficient of dibenzofulvene at 290 nm; 5800 M$^{-1}$ cm$^{-1}$ B) Characterization by RP-HPLC and RP-HPLC-ESMS Analysis B1) RP-HPLC Analysis Analytical RP-HPLC was carried out on a Waters instrument comprising a separations module (Waters 2695), an automatic injector (Waters 717 auto sampler), and a UV photodiode array detector (Waters 2998), and linear gradients of mobile phase B into mobile phase A were used and are specified in each case.

Step1 Sample Preparation:
Mobile Phase A: 0.045% (v/v) aqueous TFA
Mobile Phase B: 0.036% (v/v) TFA in ACN A specific amount of sample in the range of from 0.5 to 1 mg was dissolved in ca. of from 0.5 to 1 ml of a mixture of H$_2$O/ACN (1:1, (v/v)), the solution was filtered through a 0.45 micrometer size pore, 4 mm diameter PVDF hydrophobic filter.

Step2 Chromatography Conditions:
Column: SunFire C18, 3.5 micrometer, 4.6×100 mm
Oven: RT
Flow rate: 1.0 ml/min
Detector wavelength: 220 nm
Gradient run time: 8 min
Gradient composition: x to y % (v/v) of mobile phase B as specified in the examples Prior to the injection, the column was conditioned at initial conditions for 3 min, and after each run the column was washed with ACN for 3 min.

Step3 Chromatographic Profile Analysis:

Measure of the area of all chromatography peaks related with the products from the synthesis. The areas proportion is taken as a percentage of purity of the expected products.

B2) RP-HPLC-ESMS Analysis

Analytical RP-HPLC-ESMS was performed on a Waters Micromass ZQ spectrometer comprising a separations module (Waters 2695), an automatic injector (Waters 717 auto sampler), and a UV photodiode array detector (Waters 2998), and linear gradients of mobile phase B into mobile phase A were used.

Step1 Sample Preparation:
Mobile Phase A: 0.1% (v/v) aqueous formic acid
Mobile Phase B: 0.07% (v/v) formic acid in ACN A specific amount of sample in the range of 0.5 to 1 mg was dissolved in ca. of from 0.5 to 1 ml of a mixture of $H_2O$/ACN (1:1 (v/v)), the solution was filtered through a 0.45 micrometer size pore, 4 mm diameter PVDF hydrophobic filter.

Step2 Chromatography-Mass Spectrometry Conditions:
Column: SunFire C18, 3.5 micrometer, 2.1×100 mm
Oven: RT
Flow rate: 0.3 ml/min
Detector wavelength: 220 nm
Gradient run time: 8 min
Gradient composition: x to y % (v/v) of mobile phase B as specified in the examples
Mass range m/z (positive ion mode): 500 to 2500 Da Prior to the injection, the column was conditioned at initial conditions for 3 min, and after each run the column was washed with ACN for 3 min.

Step3 Chromatography-Mass Spectrometry Analysis
The UV and MS spectres for each peak were analyzed to determine the molecular ion mass for each peak.

B3) RP-HPLC Analysis
Analytical RP-HPLC was carried out on a Agilent 1100 Series instrument comprising a separations module, an automatic injector, and a UV photodiode array detector, and gradients of mobile phases C and D.

Step1 Sample Preparation:
Mobile Phase D: 0.1% v/v aqueous TFA
Mobile Phase C: 0.085% (v/v) TFA in ACN A specific amount of sample in the range of from 0.5 to 1 mg was dissolved in ca. of from 0.5 to 1 ml of a mixture of $H_2O$/ACN (1:2 (v/v))

Step2 Chromatography Conditions:
Column: Waters X-Terra MS C18, 3.5 micrometer, 4.6×150 mm
Oven: 35° C.
Flow rate: 1.0 ml/min
Detector wavelength: 220 nm
Gradient run time: 25 min
Gradient composition: 10 to 97% (v/v) of mobile phase C Prior to the injection, the column was conditioned at initial conditions for 2 min, and after each run the column was washed for 2 min.

Step3 Chromatographic Profile Analysis:
Measure of the area of all chromatography peaks related with the products from the synthesis. The areas proportion is taken as a percentage of purity of the expected products.

B4) RP-HPLC-ESMS Analysis
Analytical RP-HPLC-ESMS was performed on a Waters 2690, and gradients of mobile phase B into mobile phase A were used.

Step1 Sample Preparation:
Mobile Phase A: 0.1% (v/v) aqueous trifluoroacetic acid
Mobile Phase B: 0.085% (v/v) trifluoroacetic acid in ACN A specific amount of sample in the range of 0.5 to 1 mg was dissolved in ca. of from 0.5 to 1 ml of a mixture of $H_2O$/ACN (1:1 (v/v)), the solution was filtered through a 0.45 micrometer size pore, 4 mm diameter PVDF hydrophobic filter.

Step2 Chromatography-Mass Spectrometry Conditions:
Column: Waters XTerra MS C18; 150×4.6 mm
Oven: 35° C.
Flow rate: 1 ml/min
Detector wavelength: 220 nm
Run time: 30 min
Gradient composition: 10 to 97% (v/v) of mobile phase B for 20 min, 97% (v/v) of mobile phase B for 2 min, 97 to 10% (v/v) of mobile phase B for 1 min, 10% (v/v) of mobile phase B for 7 min.

Prior to the injection, the column was conditioned at initial conditions for 3 min, and after each run the column was washed with ACN for 3 min.

Step3 Chromatography-Mass Spectrometry Analysis
The UV and MS spectres for each peak were analyzed to determine the molecular ion mass for each peak.
Mass range m/z (positive ion mode): 500 to 2500 Da C) Ninhydrin Test
Preparation of Reagent Solutions
Reagent Solution A: Phenol (40 g) is dissolved in EtOH (10 ml). A solution of KCN (65 mg) in water (100 ml) is added to pyridine (freshly distilled over ninhydrin, 100 ml). Both solutions stirred for 45 min with a mixed-bed ion-exchange resin, filtered, and mixed.

Reagent Solution B: A solution of ninhydrin (2.5 g) in absolute EtOH (50 ml) was prepared and maintained in a light-proof container, preferably under inert atmosphere.

Experimental Procedure
Resin is washed with DCM and 1 to 5 mg is transferred to a small glass tube. To this tube are added six drops of reagent solution A and two drops of B. The tube was then heated at 100° C. for 3 min.

Negative test (absence of free primary amines): yellow solution and naturally coloured resin beads.

Positive test (presence of free primary amines): dark blue or purple solution and resin beads.

D) Chloranil Test
Preparation of Reagent Solution
Reagent Solution: A solution of chloranil (4.1 g) in toluene (100 ml) was prepared.

Experimental Procedure
To acetone (1 ml) small glass tube, 1 drop of reagent solution and 1 drop of testing solution where added. The tube was then mixed for about 10 s.

Negative test (absence of piperidine): colourless to light yellow

Positive test (presence of piperidine): blue or purple.

Example 1

SPPS of T20C Using an Attachment Via a Diketopiperazine Group Forming Dipeptidyl Linker to the Resin (0.1 mmol Scale)

The SPPS was performed manually.
Method Fmoc-gr-rem (Fmoc-Group-Removal)

In the following examples, the Fmoc group was removed by these procedures:

Treatment of the resin with 20% (v/v) piperidine in DMF (1×1 min, 2×10 min; 3 ml each for examples 1 to 3 and for example 7, 150 ml each for examples 4 to 6), followed by:

DMF washes (5×1 min; 3 ml each) for examples 1 to 3 and for example 7,

DMF continuous washes (600 ml) and chloranil test method D for examples 4 to 6.

Example 1.1

Attachment of the Diketopiperazine Group Forming Dipeptidyl Linker to the Resin a) Pre-Treatment of the HMPS Resin

HMPS resin (106.2 mg) was swelled with DCM (5×1 min; 3 ml each) and DMF (5×1 min; 3 ml each) at RT and then filtered.

b) Introduction of the First Amino Acid (D-Pro) of the Diketopiperazine Group Forming Dipeptidyl Linker on the Resin Fmoc-D-Pro-OH (135 mg, 4 eq) and DIPCDI (31 microliter, 2 eq) in DCM/DMF (15:1 (v/v), 2.5 ml) was added to a resin prepared according to example 1.1a). Then, DMAP (4.9 mg, 0.4 eq) in DCM (0.5 ml) was added and left to stand at RT for 2 h. The incorporation of the Fmoc-D-Pro-OH was carried out a second time following this procedure. After the preceding 2 h coupling time, the resin was washed with DCM (5×1 min; 3 ml each) and with DMF (5×1 min; 3 ml each). Then, the resin was capped using acetic anhydride (47 microliter, 5 eq) and DIEA (85 microliter, 5 eq) in DMF (2.5 ml) for 30 min at RT. After capping, the resin was washed with DMF (5×1 min; 3 ml each) and with DCM (5×1 min; 3 ml each). Then the Fmoc group was removed by the method Fmoc-gr-rem.

A 0.95 mmol/g resin loading was determined by UV quantification (method description A; $V_A$: 100 ml, $V_B$: 10 ml and $V_C$: 1.6 ml). Therefore 106.2 mg of HMPS resin represents 0.1 mmol of active sites.

c) Introduction of the Second Amino Acid (L-Lys) of the Diketopiperazine Group Forming Dipeptidyl Linker A mixture of Trt-L-Lys(Fmoc)-OH (198 mg, 3 eq), HOBt (50 mg, 3 eq) and DIPCDI (50 microliter, 3 eq) in DMF (2 ml) was shaken for 5 min at RT, then added to a resin prepared according to example 1.1 b). The mixture was left to stand at RT for 16 h. No re-coupling was required according to the ninhydrin test (method C). Then the resin was washed with DMF (5×1 min; 3 ml each) and with DCM (5×1 min; 3 ml each). Then the Fmoc group was removed by the method Fmoc-gr-rem.

d) Incorporation of a Rink Amide Handle

Fmoc-Rink-OH (175 mg, 3 eq), HOBt (50 mg, 3 eq) and DIPCDI (50 microliter, 3 eq) in DMF (2 ml) were shaken for 5 min at RT, then added to a resin prepared according to example 1.1c). The mixture was left to stand at RT for 1 h. No re-coupling was required according to the ninhydrin test (method C). After the preceding 1 h coupling time, the resin was washed with DMF (5×1 min; 3 ml each) and with DCM (5×1 min; 3 ml each). Then the Fmoc group was removed by the method Fmoc-gr-rem.

Example 1.2

T20C by SPPS

Each amino acid was reacted in a reaction cycle. The reaction steps in one reaction cycle for the incorporation of one amino acid follow the reaction cycle description (i) or (ii).

a) Reaction Cycle Description (i)

The mixture of Fmoc-Xaa-OH (3 eq), HCTU (140 mg, 3 eq) and DIEA (110 microliter, 6 eq) in DMF (2 ml) was shaken for 30 s at RT, then added to the resin prepared according to the preceding step in the elongation sequence. The mixture was left to stand at RT for 1 h. No re-coupling was required according to the ninhydrin test (method C). Then the resin was washed with DMF (5×1 min; 3 ml each) and with DCM (5×1 min; 3 ml each). Then the Fmoc group was removed by the method Fmoc-gr-rem.

b) Reaction Cycle Description (ii)

The mixture of Fmoc-Xaa-OH (3 eq), HCTU (140 mg, 3 eq), DIEA (110 microliter, 6 eq) in DMF (2 ml) was shaken for 30 s at RT, then added to the resin prepared according to the preceding step in the elongation sequence. The mixture was left to stand at RT for 1 h. A re-coupling was carried out using a mixture of Fmoc-Xaa-OH (3 eq), HCTU (140 mg, 3 eq), DIEA (110 microliter, 6 eq) in DMF (2 ml). This mixture was shaken for 30 s at RT, and then added to the resin and left to stand at RT for 1 h. Then the resin was washed with DMF (5×1 min; 3 ml each) and the resin was capped using acetic anhydride (47 microliter, 5 eq) and DIEA (85 microliter, 5 eq) in. DMF (2.5 ml) for 15 min at RT. Then the resin was washed with DMF (5×1 min; 3 ml each) and with DCM (5×1 min; 3 ml each). Then the Fmoc group was removed by the method Fmoc-gr-rem.

c) Elongation Sequence

The first amino acid, Fmoc-$^{36}$Phe-OH, was coupled to a resin comprising a diketopiperazine group forming dipeptidyl linker and a Rink amide handle group, prepared according to example 1.1 d), the following amino acids were then coupled to the amino acid/peptide Rink amide handle group comprising resin prepared in the preceding step in the elongation sequence. The sequence of incorporation of the amino acids was:

| Fmoc-Xaa-OH | Reaction cycle description |
|---|---|
| 1. Fmoc-$^{36}$Phe-OH (128 mg) | (i) |
| 2. Fmoc-$^{35}$Trp(Boc)—OH (175 mg) | (i) |
| 3. Fmoc-$^{34}$Asn(Trt)-OH (198 mg) | (i) |
| 4. Fmoc-$^{33}$Trp(Boc)—OH (175 mg) | (i) |
| 5. Fmoc-$^{32}$Leu-OH (117 mg) | (i) |
| 6. Fmoc-$^{31}$Ser(tBu)—OH (127 mg) | (i) |
| 7. Fmoc-$^{30}$Ala-OH•H$_2$O (110 mg) | (i) |
| 8. Fmoc-$^{29}$Trp(Boc)—OH (175 mg) | (i) |
| 9. Fmoc-$^{28}$Lys(Boc)—OH (2 times 156 mg) | (ii) |
| 10. Fmoc-$^{27}$Asp(tBu)—OH (137 mg) | (i) |

Example 1.3

Analysis—Cleavage of T20C from Rink Amide Handle Group

A small portion of peptidyl-resin (5 mg), prepared according to example 1.2, was cleaved from the Rink amide handle group by treating the resin with 1 ml of a mixture consisting of 95% (v/v) TFA, 2.5% (v/v) TIS and 2.5% (v/v) H$_2$O for 1 h at RT. The peptide was obtained in 83% purity (RP-HPLC, method description B1, 25 to 50 of mobile phase B).

Example 1.4a

Trt Protecting Group Removal of the L-Lys of the Diketopiperazine Group Forming Dipeptidyl Linker, Formation of the Diketopiperazine Residue Comprising C-Terminal Protecting Group and Cleavage from the Resin

In a first step, the Trt protecting group of the L-Lys of the diketopiperazine group forming dipeptidyl linker was removed by treating a peptidyl-resin (15 mg), prepared according to example 1.2, with 0.2% (v/v) TFA in DCM (2 ml) at RT for 2×5 min. Then, in a second step, the thus obtained from Trt deprotected peptidyl-resin was neutralized by washing with 5% (v/v) DIEA in DCM (2 ml) at RT for 2×5 min.

The RP-HPLC analysis after the first step did not show any peptide cleaved from the resin or from the Rink amide handle group, and after the second step, no peptidyl-resin comprising a DKP linker group was observed (method description B1, 5 to 100 of mobile phase B).

After the second step, the peptide comprising the diketopiperazine residue comprising C-terminal protecting group was obtained by treating the peptidyl resin from the second step with 5% (v/v) piperidine in THF at RT (5×5 min, 2 ml each).

THF was removed by evaporation under vacuum and the resulting peptide comprising the diketopiperazine residue comprising C-terminal protecting group was analyzed by RP-HPLC-ESMS (method description B2, 80 to 100 of mobile phase B, [(M+2H)/2]2+: 1308.0, respectively, where M is the MW of T20C comprising the DKP linker group. The expected product was obtained as a racemic mixture due to the Rink amide handle group, and the observed molecular mass corresponded to the theoretically expected mass.

In order to quantify how much of the diketopiperazine group forming dipeptidyl linker had remained on the resin, the resin was treated with 2 ml of a mixture consisting of 95% (v/v) TFA, 2.5% (v/v) TIS and 2.5% (v/v) $H_2O$ for 1 h at RT. The RP-HLPC analysis showed that there was less than 1% left of diketopiperazine group forming dipeptidyl linker in the resin (method description B1, 5 to 100 of mobile phase B).

Example 1.4b

Example 1.4a was repeated with the sole difference, that after the second step, the peptide comprising the diketopiperazine residue comprising C-terminal protecting group was obtained not by treating the resin with 5% (v/v) piperidine in THF at RT (5×5 min, 2 ml each) as in example 1.4a, but by treating with 5% (v/v) piperidine in DMF at RT (5×5 min, 2 ml each). DMF was removed by co-evaporation with toluene (5×3 ml) under vacuum.

Example 1.4c

Example 1.4a was repeated with the sole difference, that after the second step, the peptide comprising the diketopiperazine residue comprising C-terminal protecting group was obtained not by treating the resin with 5% (v/v) piperidine in THF at RT (5×5 min, 2 ml each) as in example 1.4a, but by treating with 5% (v/v) pyrrolidine in THF at RT (5×5 min, 2 ml each).

Example 1.4d

Example 1.4a was repeated with the sole difference, that after the second step, the peptide comprising the diketopiperazine residue comprising C-terminal protecting group was obtained not by treating the resin with 5% (v/v) piperidine in THF at RT (5×5 min, 2 ml each) as in example 1.4a, but by treating with 5% (v/v) pyrrolidine in DMF at RT (5×5 min, 2 ml each). DMF was removed by co-evaporation with toluene (5×3 ml) under vacuum.

In all three examples 1.4b, 1.4c and 1.4d, the same analytical results with RP-HPLC-ESMS analysis and with the determination of residually remaining diketopiperazine group forming dipeptidyl linker on the resin were obtained as in example 1.4a.

Example 2

SPPS of T20C Using as Attachment to the Resin a Diketopiperazine Residue Comprising C-Terminal Protecting Group (5 mmol Scale)

The SPPS was performed manually.

Example 2.1

Attachment of the Diketopiperazine Group Forming Dipeptidyl Linker to the HMPS Resin a) Pre-Treatment of HMPS Resin
HMPS resin (5.0977 g) was swelled with DCM (5×1 min; 50 ml each) and DMF (5×1 min; 50 ml each) at RT and then filtered.
b) Introduction of the First Amino Acid (D-Pro) of the Diketopiperazine Group Forming Dipeptidyl Linker on the Resin.
Fmoc-D-Pro-OH (6.6 g, 4 eq) and DIPCDI (1.5 ml, 2 eq) in DCM/DMF (15:1 (v/v), 100 ml) was added to a resin prepared according to example 2.1a). Then, DMAP (245 mg, 0.4 eq) in DCM (5 ml) was added and left to stand at RT for 16 h. The first amino acid was re-coupled using Fmoc-D-Pro-OH (6.6 g, 4 eq) and DIPCDI (1.5 ml, 2 eq) in DCM/DMF (15:1 (v/v), 100 ml) for 5 h at RT. After coupling, the resin was washed with DCM (5×1 min; 50 ml each) and with DMF (5×1 min; 50 ml each). Then, the resin was capped using acetic anhydride (2.4 ml, 5 eq) and DIEA (4.4 ml, 5 eq) in DMF (50 ml) for 1 h at RT. After capping, the resin was washed with DCM (5×1 min; 50 ml each) and with DMF (5×1 min; 50 ml each). Then the Fmoc group was removed by treatment with piperidine/DMF (20% (v/v), 1×1 min, 2×10 min; 50 ml each).
A 0.98 mmol/g resin loading was determined by UV quantification (method description A; VA: 250 ml, VB: 50 ml, and VC: 0.44 ml). Therefore 5.0977 g of HMPS resin represents 5.0 mmol of active sites.
c) Introduction of the Second Amino Acid (L-Lys) of the Diketopiperazine Group Forming Dipeptidyl Linker
A mixture of Trt-Lys(Fmoc)-OH (9.2 g, 3 eq), HOBt (2.3 g, 3 eq) and DIPCDI (2.3 ml, 3 eq) in DMF (100 ml) was shaken for 5 min at RT, then added to a resin prepared according to example 2.1 b), and then the mixture was left to stand at RT for 16 h. No re-coupling was required, according to the ninhydrin test (method C). Then the resin was washed with DMF (5×1 min; 50 ml each) and with DCM (5×1 min; 50 ml each). Then the Fmoc group was removed by treatment with piperidine/DMF (20% (v/v), 1×1 min, 2×10 min; 50 ml each).
d) Introduction of a Rink Amide Handle Group
A mixture of Fmoc-Rink-OH (7.9 g, 3 eq), HOBt (2.3 g, 3 eq) and DIPCDI (2.3 ml, 3 eq) in DMF (100 ml) was shaken for 5 min at RT, then added to a resin prepared according to example 2.1c), and then left to stand at RT for 16 h. No re-coupling was required, according to the ninhydrin test (method C). Then the resin was washed with DMF (5×1 min; 50 ml each) and with DCM (5×1 min; 50 ml each). Then the Fmoc group was removed by treatment with piperidine/DMF (20% (v/v), 1×1 min, 2×10 min; 100 ml each).

Example 2.2

T20C by SPPS

Each amino acid was reacted in a reaction cycle. The reaction steps in one reaction cycle for the incorporation of one amino acid follow the Reaction cycle description (iii) or (iv).

a) Reaction Cycle Description (iii)

A mixture of Fmoc-Xaa-OH (3 eq), HCTU (6.2 g, 3 eq), DIEA (5.2 ml, 6 eq) in DMF (100 ml) was shaken for 30 s at RT, then added to the resin prepared according to the preceding step in the elongation sequence. The mixture was then left to stand at RT for 2 h. No re-coupling was required, according to the ninhydrin test (method C). Then the resin was washed with DMF (5×1 min; 100 ml each) and with DCM (5×1 min; 100 ml each). Then the Fmoc group was removed by treatment with piperidine/DMF (20% (v/v), 1×1 min, 2×10 min; 100 ml each).

b) Reaction Cycle Description (iv)

A mixture of Fmoc-Xaa-OH (3 eq), HOBt (2.3 g, 3 eq), DIPCDI (2.3 ml, 3 eq) in DMF (100 ml) was shaken for 5 min at RT, then added to the resin prepared according to the preceding step in the elongation sequence, and then left to stand at RT for 16 h. A re-coupling was carried out using a mixture of Fmoc-Xaa-OH (3 eq), HCTU (6.2 g, 3 eq), DIEA (5.2 ml, 6 eq) in DMF (100 ml). This mixture was shaken for 30 s at RT, and then added to the resin and left to stand at RT for 2 h. Then, the resin was washed with DMF (5×1 min; 100 ml each) and the resin was capped using acetic anhydride (2.4 ml, 5 eq), DIEA (4.4 ml, 5 eq) in DMF (100 ml) for 1 h at RT. Then, the resin was washed with DMF (5×1 min; 100 ml each) and with DCM (5×1 min; 100 ml each). Then the Fmoc group was removed by treatment with piperidine/DMF (20% (v/v), 1×1 min, 2×10 min; 100 ml each).

c) Elongation Sequence

The first amino acid, Fmoc-$^{36}$Phe-OH, was coupled to a Rink amide handle group and diketopiperazine group forming dipeptidyl linker comprising resin, prepared according to example 2.1d), the following amino acids were then coupled to with the resulting amino acid/peptide Rink amide handle group and diketopiperazine group forming dipeptidyl linker comprising resin prepared in the respective preceding step in the elongation sequence. The sequence of incorporation of the amino acids is given in table c1):

TABLE c1

| Fmoc-Xaa-OH | Reaction cycle description |
|---|---|
| 1. Fmoc-$^{36}$Phe-OH (5.8 g) | (iii) |
| 2. Fmoc-$^{35}$Trp(Boc)—OH (7.9 g) | (iii) |
| 3. Fmoc-$^{34}$Asn(Trt)-OH (8.8 g) | (iii) |
| 4. Fmoc-$^{33}$Trp(Boc)—OH (7.9 g) | (iii) |
| 5. Fmoc-$^{32}$Leu-OH (5.3 g) | (iii) |
| 6. Fmoc-$^{31}$Ser(tBu)—OH (5.6 g) | (iii) |
| 7. Fmoc-$^{30}$Ala-OH•H2O (4.7 g) | (iii) |
| 8. Fmoc-$^{29}$Trp(Boc)—OH (7.9 g) | (iii) |
| 9. Fmoc-$^{28}$Lys(Boc)—OH (2 times 6.8 g) | (iv) |
| 10. Fmoc-$^{27}$Asp(tBu)—OH (6.0 g) | (iii) |

Example 2.3

Analysis—Cleavage of T20C from Rink Amide Handle Group

A small portion of peptidyl-resin (5 mg), prepared according to example 2.2, was cleaved from the Rink amide handle group by treating the resin with 1 ml of a mixture of 95% (v/v) TFA, 2.5% (v/v) TIS, and 2.5% (v/v) H2O for 1 h at RT. The peptide was obtained in 72% purity, as determined by analytical RP-HPLC (method description B1, 25 to 50 of mobile phase B).

Example 2.4

Trt Protecting Group Removal of the L-Lys of the Diketopiperazine Group Forming Dipeptidyl Linker, Formation of the Diketopiperazine Residue Comprising C-Terminal Protecting Group and Cleavage from the Resin Diketopiperazine residue comprising C-terminal protecting group formation and cleavage of a peptide fragment, prepared according to example 2.2, from the resin (1.57 g) are brought about in analogous manner as described in example 1.4a with the amounts of reagents and solvent adapted to the higher amount of peptidyl-resin:

a) Trt Group Deprotection
0.5% (v/v) TFA in DCM (2×5 min; 20 ml each).

b) Neutralization
5% (v/v) DIEA in DMF (2×5 min; 20 ml each).

c) DKP Linker Group Formation
5% (v/v) piperidine in THF (5×5 min; 20 ml each).

The THF was removed under vacuum and the resulting crude was washed with pre-cooled (4° C.) Et2O (50 ml×3). 642.5 mg of T20C comprising the diketopiperazine residue comprising C-terminal protecting group were obtained.

Example 3

Preparation of HT20F: a) SPPS of BocT20N, b) HSPPS Coupling with T20C Comprising the Diketopiperazine Residue Comprising C-Terminal Protecting Group, and c) Total Deprotection A T20C comprising the diketopiperazine residue comprising C-terminal protecting group was obtained according to example 2.4.

Example 3.1

BocT20N by SPPS

The SPPS of a BocT20N was performed manually by linear Fmoc SPPS. Only last Glu amino acid was Boc protected Boc-Glu(tBu)-OH.

a) Pre-Treatment of CTC Resin
CTC resin (5.0054 g) was swelled with DCM (5×1 min; 50 ml each) and DMF (5×1 min; 50 ml each) at RT and then filtered.

b) Introduction of the First Amino Acid (L-Leu) on the CTC Resin:
Fmoc-$^{26}$Leu-OH (1.8 g, 1 eq), DIEA (8.7 ml, 10 eq) in DCM (50 ml) was added to a resin, prepared according to example 3.1a), and the mixture was left to stand at RT for 1 h. Then the resin was capped by treatment of the resin with MeOH (0.8 microliter/mg resin; 4 ml) for 15 min at RT. After capping the resin was washed with DCM (5×1 min; 50 ml each) and with DMF (5×1 min; 50 ml each). Then the Fmoc group was removed by treating the resin with piperidine/DMF (20% (v/v), 1×1 min, 2×10 min; 50 ml each).

After the Fmoc-$^{26}$Leu-OH incorporation, a 0.89 mmol/g resin loading was determined by UV quantification (method description A; $V_A$: 250 ml, $V_B$: 50 ml, and $V_C$: 0.34 ml).

c) BocT20N by SPPS
Each amino acid was reacted in a reaction cycle. The reaction steps in one reaction cycle for the incorporation of one amino acid follow the reaction cycle description (v).

c1) Reaction Cycle Description (v)

A mixture of Fmoc-Xaa-OH (3 eq), Oxyma (1.9 g, 3 eq), DIPCDI (2.3 ml, 3 eq) in DMF (V1 ml as given in the table c2) was shaken for 5 min at RT, then added to the resin prepared according to the preceding step in the elongation sequence. Then the mixture was left to stand at RT for 16 h. No re-coupling was required, according to the ninhydrin test (method C). Then, the resin was washed with DMF (5×1 min; V2 ml as given in the table c2) and with DCM (5×1 min; V2 ml as given in the table c2).

Then the Fmoc group was removed by treating the resin with piperidine/DMF (20% (v/v), 1×1 min, 2×10 min; V3 ml as given in table c2).

c2) Elongation Sequence

The second amino acid, Fmoc-$^{25}$Glu(tBu)-OH, was coupled according to the reaction cycle description (v) to a resin prepared according to example 3.1b), the following amino acids were then coupled according to the reaction cycle description (v) to the resulting amino acid/peptidyl CTC-resin prepared in the preceding step of the elongation cycle. The sequence of incorporation of the amino acids is given in table c2).

TABLE c2

| Fmoc-Xaa-OH | ml V1 | ml V2 | ml V3 |
|---|---|---|---|
| 1. Fmoc-$^{25}$Glu(tBu)—OH (5.7 g) | 50 | 50 | 50 |
| 2. Fmoc-$^{24}$Leu-OH (4.7 g) | 50 | 50 | 50 |
| 3. Fmoc-$^{23}$Leu-OH (4.7 g) | 50 | 50 | 50 |
| 4. Fmoc-$^{22}$Glu(tBu)—OH (5.7 g) | 70 | 70 | 70 |
| 5. Fmoc-$^{21}$Gln(Trt)-OH (8.1 g) | 70 | 70 | 70 |
| 6. Fmoc-$^{20}$Glu(tBu)—OH (5.7 g) | 100 | 70 | 70 |
| 7. Fmoc-$^{19}$Asn(Trt)-OH (8.0 g) | 100 | 70 | 70 |
| 8. Fmoc-$^{18}$Lys(Boc)—OH (6.3 g) | 100 | 70 | 70 |
| 9. Boc-$^{17}$Glu(tBu)—OH (6.3 g) | 100 | 70 | 70 |

Example 3.2

Analysis—Cleavage of HT20N from CTC Resin

Peptidyl-resin (5 mg), prepared according to example 3.1c2), was treated with 1 ml of a mixture consisting of 95% (v/v) TFA, 2.5% (v/v) TIS and 2.5% (v/v) H2O for 1 h at RT for cleaving the peptide from the CTC resin and for fully deprotecting the amino acid residues. The HT20N was obtained in 85.7% purity, as determined by RP-HPLC (method description B1, 5 to 100 of mobile phase B). The peptide was analysed by RP-HPLC-ESMS (method description B2, 5 to 100 of mobile phase B, [M+H]+: 1244.7, where M corresponds to the fully deprotected HT20N).

Example 3.3

BocT20N Side Chain Protected

Peptidyl resin (1.094 g), prepared according to example 3.1c2), was treated with 1% (v/v) TFA in DCM (5×1 min; 50 ml each) at RT, all 5 mixtures were poured into H2O (20 ml). Then, this aqueous mixture was evaporated and the crude was lyophilized. The fully side chain protected BocT20N was obtained (510 mg) and was analysed by RP-HPLC-ESMS (method description B2, 95 to 100 of mobile phase B, [M+H]+: 2153.8).

No partial deprotection of the fully side chain protected BocT20N was observed by RP-HPLC-ESMS (method description B1, 50 to 100 of mobile phase B). RP-HPLC showed one peak, purity was 85.7% (method description B2, 95 to 100 of mobile phase B).

Example 3.4

HT20F by HSPPS a) HSPPS Coupling Between the T20C Comprising the Diketopiperazine Residue Comprising C-Terminal Protecting Group and BocT20N Side chain protected BocT20N (10 mg, 4.6 micromol), prepared according to example 3.3, and HOBt (2.2 mg, 3 eq) were dissolved in DCM (350 microliter) and DIPCDI (2.2 microliter, 3 eq) was added to the mixture. The mixture was shaken for 5 min at RT. The mixture was added to a solution of T20C comprising the diketopiperazine residue comprising C-terminal protecting group (12 mg, 4.6 micromol), prepared according to example 2.4, in DCM (350 microliter). The resulting mixture was stirred at RT for 16 h. The coupling was monitoring by RP-HPLC analysis (method description B1, 95 to 100 of mobile phase B), total conversion was observed after 16 h.

Solvent was evaporated under vacuum resulting in the fragment Boc[T20-17-36] connected C-terminally to the diketopiperazine residue comprising C-terminal protecting group.

b) HT20F by Total Deprotection

A fragment Boc[T20-17-36] connected C-terminally to the diketopiperazine residue comprising C-terminal protecting group (1 mg), prepared according to example 3.4a), was treated with 1 ml of a mixture of 92.5% (v/v) TFA, 2.5% (v/v) TIS and 5% (v/v) DMB for 1 h at RT. In order to remove the resulting N-carboxy groups on the side chains of the Trp residues, 0.5% (v/v) aqueous NH3 (1 ml) were added and the mixture was left to stand for 16 h at RT to obtain the fully deprotected HT20F with 60.2% purity, as determined by RP-HPLC (method description B1, 30 to 40 of mobile phase B). RP-HPLC-ESMS showed the target peptide (method description B2, 30 to 40 of mobile phase B) with [(M+2H)/2]2+: 1290.0, where M is the MW of HT20F.

Example 4

Preparation of Compound of Formula (ex-4) by SPPS

Ac-Tyr(OtBu)-His(Trt)-Ala-OH    (ex-4)

a) Pre-Treatment of CTC Resin

CTC resin (20.4 g) was swelled with DCM (1 h; 200 ml) at RT and then filtered.

b) Introduction of the First Amino Acid (Fmoc-Ala-OH) on the CTC Resin

Fmoc-Ala-OH (12.65 g, 1.2 eq), DIEA (14.90 g, 3.6 eq) in DCM (160 ml) was added to a resin prepared according to example 4a), the mixture was left to stand at RT for 2 h, and then filtered. The resin was treated with DIEA/MeOH (10% (v/v), 200 ml) and DMF (40 ml) for 1 h at RT and then filtered. Then the Fmoc group was removed according to method Fmoc-gr-rem. After the Fmoc-Ala-OH incorporation, a 0.97 mmol/g resin loading was calculated.

c1) Incorporation of Amino Acids by SPPS

Starting with a resin prepared according to example 4.b), each amino acid, respectively 1. Fmoc-His(Trt)-OH and 2. Fmoc-Tyr(tBu)-OH, were incorporated following the reaction cycle description example 4c2).

c2) Cycle Description

A mixture of the respective Fmoc-Xaa-OH (1.5 eq), HOBt (9.2 g, 2.25 eq), DIPCDI (9.31 ml, 2.25 eq) in DMF (103 g) was stirred for 5 min at RT, then added to a resin prepared according to example 4 b), and then left to stand at RT for 45 min. Then DIPCDI (4.66 ml, 1.25 eq) was added and the mixture left to stand at RT for 45 min. No re-coupling was required, according to the ninhydrin test (method C). The resin was washed with DMF (3×5 min; 110 ml each). Then the Fmoc group was removed according to method Fmoc-gr-rem. All piperidine was removed according to the chloranil test (method D).

d) Cleavage from the Resin

The resin prepared according to example 4c1) was washed with 2% (w/w) TFA in DCM (4×15 min; 150 g each) at approx. 10° C. Then the resin was washed with EtOH/DCM (20% (w/w), 3×3 min; 120 g each) at RT 10° C. The combine solution was concentrated by co-evaporation with EtOH under reduced pressure (1×40 g).

e) Isolation

To the solution (107.60 g) obtained according to example 4d), water (800 g) was added. The resulting mixture was filtered and the solid washed with water (3×3 min; 80 g each) and DIPE (3×2 min; 120 ml each).

The solid was dried at 30° C. under reduced pressure to obtain 20.80 g of compound of formula (ex-4) as white powder with a purity of 94.7% as determined by RP-HPLC (method B3).

Example 5

Attachment of the Diketopiperazine Group Forming Dipeptidyl Linker to the HMPS Resin, Use of a Ramage Handle Group, and Preparation of Compound of Formula (ex-5i)

a) Pre-Treatment of HMPS Resin

HMPS resin (5.0 g) was swelled with DCM (5×1 min; 150 ml each) and DMF (5×1 min; 150 ml each).

b) Introduction of the First Amino Acid on the Resin.

The respective amino acid (N(Me)Phe-OH or Fmoc-D-Pro-OH) and DIPCDI (2.43 g, 3.5 eq) in DCM/DMF (15:1 (v/v), 125 ml) was added to a resin prepared according to example 5a). Then, DMAP (0.27 g, 0.4 eq) in DCM (25 ml) was added and left to stand at RT for 3 or 4 h. The resin was washed with DCM (5×1 min; 150 ml each) and with DMF (5×1 min; 150 ml each). Then, the resin was capped using acetic anhydride (2.81 g, 5 eq) and DIEA (3.56 g, 5 eq) in DMF (125 ml) for 30 min at RT. After capping, the resin was washed with DMF (5×1 min; 150 ml each). Then the Fmoc group was removed according to method Fmoc-gr-rem. A 1.10 mmol/g resin loading was calculated, therefore 5.0 g of HMPS resin represents 5.5 mmol of active sites.

b1) Procedure according to example 5 b) with Xaa being N(Me)Phe-OH (4.86 g, 2.2 eq) and left to stand at RT for 4 h.

b2) Procedure according to example 5 b) with Xaa being Fmoc-D-Pro-OH (7.45 g, 4.0 eq) and left to stand at RT for 3 h.

c) Introduction of the Second Amino Acid

A mixture of Trt-Lys(Fmoc)-OH (11.26 g, 2 eq), HOBt (4.24 g, 3 eq) and DIPCDI (3.49 g, 3 eq) in DMF (100 ml) was stirred for 5 min at RT, then added to a resin prepared according to example 5 b 1). The mixture was stirred at RT for 17 h.

Then, the resin was washed with DMF (5×1 min; 150 ml each), and the Fmoc group was removed according to method Fmoc-gr-rem.

d) Incorporation of Amino Acids by SPPS

Starting with a resin prepared according to example 5c), the handle group and the respective amino acids, i.e. 1. Fmoc-Ramage-OH, 2. Fmoc-Leu-OH, 3. Fmoc-Ala-OH and 4. Fmoc-Phe-OH, were incorporated following the reaction cycle description (vi).

e) Reaction Cycle Description (vi)

A mixture of the handle group or of the respective amino acids Fmoc-Xaa-OH (2 eq), HOBt (4.24 g, 3 eq), DIPCDI (3.49 g, 3 eq) in DMF (100 ml) was stirred for 5 min at RT, then added to the resin prepared according to according to example 5c) (in case of the handle group) and then d) (in case of the amino acids) respectively, and then left to stand at RT for 1 h. The resin was washed with DMF (5×1 min; 150 ml each), and additionally with DCM (5×1 min; 150 ml each) when Xaa was Fmoc-Phe-OH. The resin was washed further with DMF (1×1 min; 150 ml) at RT when Xaa was Fmoc-Ala-OH. The Fmoc group was removed according to method Fmoc-gr-rem except for the last Xaa, the Fmoc-Phe-OH.

f) Analysis—Cleavage of the Peptide from the Handle Group and Thereby Also from the Resin A small portion of resin (5 mg) obtained according to example 5 d) was treated with 1 ml of a mixture of 95% (v/v) TFA, 2.5% (v/v) TIS and 2.5% (v/v) water for 1 h at RT. A compound of formula (ex-5f) was obtained in 86.4% purity, as determined by analytical RP-HPLC (HPLC-method B3).

Fmoc-Phe-Ala-Leu-NH$_2$ (ex-5f)

g) Trt Protecting Group Removal of the L-Lys of the Linker, Formation of the Diketopiperazine Residue Comprising C-Terminal Protecting Group and Cleavage from the Resin Formation of the diketopiperazine residue comprising C-terminal protecting group and cleavage of the DKP-peptide from the resin prepared according to example 5d), are brought about in analogous manner as described in example 1.4a with the amounts of reagents and solvent adapted to the amount of peptidyl-resin:

g1) Trt Group Deprotection

Treatment of the compound prepared according to example 5 d) with 0.2% (v/v) TFA in DCM (2×5 min, 100 ml each).

g2) Neutralization

Then treatment with 5% (v/v) DIEA in DCM (2×5 min; 100 ml each) and DCM (2×1 min; 50 ml each). HPLC was used to ensure that no product remained in the liquid phases (HPLC-method B3).

g3) Formation of the Diketopiperazine Residue Comprising C-Terminal Protecting Group and Cleavage from the Resin Then treatment with 5% (v/v) piperidine in THF (5×5 min, 100 ml each). Then, the resin was washed with THF (3×1 min; 100 ml each). HPLC was used to ensure that the product was in the combined liquid phase (HPLC-method B3).

The THF was removed by co-evaporation with toluene (3×150 ml) under vacuum. 1.96 g of a white solid of a mixture of DBF-Adduct and compound of formula (ex-5g4) were obtained. Method B4 gave the expected mass.

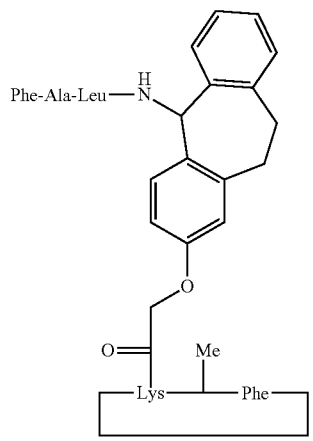

(ex-5g4)

g4) DBF-Adduct Removal

The white solid prepared according to example 5 g3) was washed with DIPE (1×2 min, 50 ml; 3×2 min, 10 ml each). 223.7 mg of compound of formula (ex-5g4) were obtained as a white solid.

h) Analysis—Cleavage of the Peptide from the Diketopiperazine Residue Comprising C-Terminal Protecting Group A small portion of compound of formula (ex-5g4) (5 mg), prepared according to example 5 g4), was deprotected by treatment with 1 ml of a mixture of 95% (v/v) TFA, 2.5% (v/v) TIS and 2.5% (v/v) water for 1 h at RT. Compound of formula (ex-5h) was obtained, the structure was confirmed by RP-HLPC analysis method B3

Phe-Ala-Leu-NH₂ (ex-5h)

i) Coupling of Compound of Formula (ex-4) with Compound of Formula (ex-5g4) by HSPPS A mixture of compound of formula (ex-4) (84 mg, 1 eq), prepared according to example 4, HOBt (53 mg, 3.2 eq) and DIPCDI (53 microliter, 3.1 eq) in DCM (2 ml) was stirred for 15 min at RT, then added to a solution of compound of formula (ex-5g4), prepared according to example 5 g4), (100 mg, 1.1 eq) in DCM (1 ml), and then the mixture was stirred at RT for 4 h. The coupling was monitored by HPLC method B3.

The reaction mixture was washed with aqueous saturated NaHCO₃ (2×40 ml), 1M KHSO₄ aqueous solution (2×40 ml) and aqueous saturated NaCl (2×40 ml).

The organic phase was dried over MgSO₄ and concentrated under reduced pressure to obtain 328.5 mg of compound of formula (ω-51) as an oil in 55% purity, as determined by analytical RP-HPLC (method description B4), consisting of 2 peaks of 26.8% and 28.2% each due to the 2 diastereoisomers caused by the chirality of the Ramage handle group. (The core peptide below Is disclosed as SEQ ID NO: 5)

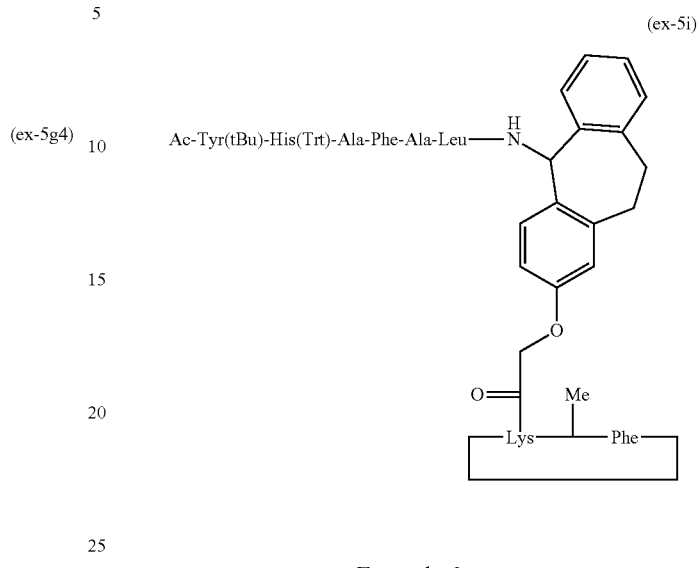

(ex-5i)

Example 6

Attachment of the Diketopiperazine Group Forming Dipeptidyl Linker to the HMPS Resin. Preparation of Compounds of Formulae (ex-6e3-d1), (ex-6e3-d2), (ex-6f1) and (ex-6f1)

a) Introduction of the Second Amino Acid L-Lys

A mixture of Trt-Lys(Fmoc)-OH (10.08 g, 2 eq), HOBt (3.79 g, 3 eq) and DIPCDI (3.12 g, 3 eq) in DMF (100 ml) was stirred for 5 min at RT, then added to a resin prepared according to example 5 b2). The mixture was stirred at RT for 17 h.

Then, the resin was washed with DMF (5×1 min; 150 ml each), and the Fmoc group was removed according to method Fmoc-gr-rem.

b) Introduction of Handle Group, Spacer Group and Amino Acids by SPPS

The handle group, spacer group and each amino acid was reacted in a reaction cycle. The reaction steps in one reaction cycle for the incorporation of one amino acid follow the reaction cycle description (vii).

c) Reaction Cycle Description (Vii) for Elongation Sequences D1) and d2)

Each time, a mixture of the spacer group providing Fmoc-TTDS-OH in case of d1), of the handle group providing Fmoc-Rink-OH or of the respective Fmoc-Xaa-OH, according to the elongation sequence, together with HOBt (3.79 g, 3 eq) and DIPCDI (3.12 g, 3 eq) in DMF (100 ml) was stirred for 5 min at RT and then added firstly to a resin prepared according to example 6a) and then to the resin prepared in the preceding step in the elongation sequence. The mixture was stirred at RT for 1 to 4 h. Then, the resin was washed with DMF (5×1 min; 150 ml each. 6× instead of 5× when Fmoc-Xaa-OH was Fmoc-Ala-OH) and the Fmoc group was removed according to method Fmoc-gr-rem.

Only before Fmoc group removal of the last Fmoc-Xaa-OH of the respective elongation sequence d1) or d2), a small portion of obtained peptidyl-resin (5 mg) was cleaved from the Rink amide handle group by treating the resin with 1 ml of a mixture consisting of 95% (v/v) TFA, 2.5% (v/v) TIS and 2.5% (v/v) $H_2O$ for 1 h at RT. Compound of formula (ex-6c-d1) was obtained in 46.7% purity by elongation sequence d1),and compound of formula (ex-6c-d2) in 65.4% purity by elongation sequence d2) (RP-HPLC, method description B3).

Fmoc-Phe-Ala-Leu-$NH_2$ (ex-6c-d1)

Fmoc-Tyr(tBu)-His(Trt)-Leu-$NH_2$ (ex-6c-d2)

d) Incorporation of Amino Acids by SPPS

The sequence of incorporation of the amino acids was:

| Elongation sequence d1) | |
|---|---|
| Fmoc-TTDS-OH/Fmoc-Rink-OH/Fmoc-Xaa-OH | mixture stirred for |
| 1. Fmoc-TTDS-OH (5 g) | 4 h |
| 2. Fmoc-Rink-OH (9.11 g) | 1 h |
| 3. Fmoc-Leu-OH (5.83 g) | 1 h |
| 4. Fmoc-Ala-OH (5.43 g) | 1 h |
| 5. Fmoc-Phe-OH (3.69 g) | 2 h |

| Elongation sequence d2) | |
|---|---|
| Fmoc-Xaa-OH/Fmoc-Rink-OH | mixture stirred for |
| 1. Fmoc-Rink-OH (9.10 g) | 1 h |
| 2. Fmoc-Leu-OH (5.83 g) | 2 h |
| 3. Fmoc-His(Trt)-OH (10.23 g) | 1 h |
| 4. Fmoc-Tyr(tBu)—OH (7.59 g) | 1 h | e) Trt Protecting Group Removal of the L-Lys of the Diketopiperazine Group Forming Dipeptidyl Linker, Formation of the Diketopiperazine Residue Comprising C-Terminal Protecting Group and Cleavage from the Resin Formation of the diketopiperazine residue comprising C-terminal protecting group and cleavage of the DKP-peptides from the resins prepared according to examples 6c) in combination with examples 6 d1) and 6 d2) respectively, are brought about in analogous manner as described in example 1.4a with the amounts of reagents and solvent adapted to the amount of peptidyl-resin:

e1) Trt Group Deprotection

Treatment of the compound prepared according to example 6c) in combination with examples 6 d1) and 6 d2) respectively with 0.2% (v/v) TFA in DCM (2×5 min, 100 ml each).

e2) Neutralization

Then treatment with 5% (v/v) DIEA in DCM (2×5 min; 100 ml each), DCM (2×1 min; 100 ml each) and THF (2×1 min; 100 ml each).

e3) Formation of the Diketopiperazine Residue Comprising C-Terminal Protecting Group and Cleavage from the Resin Treatment according to the procedure of example 5 g3). Oils were obtained, 0.83 g of compound of formula (ex-6e3-d1) in case of the starting material from example 6 d1), and 2.03 g of compound of formula (ex-6e3-d2) in case of the starting material from example 6 d2).

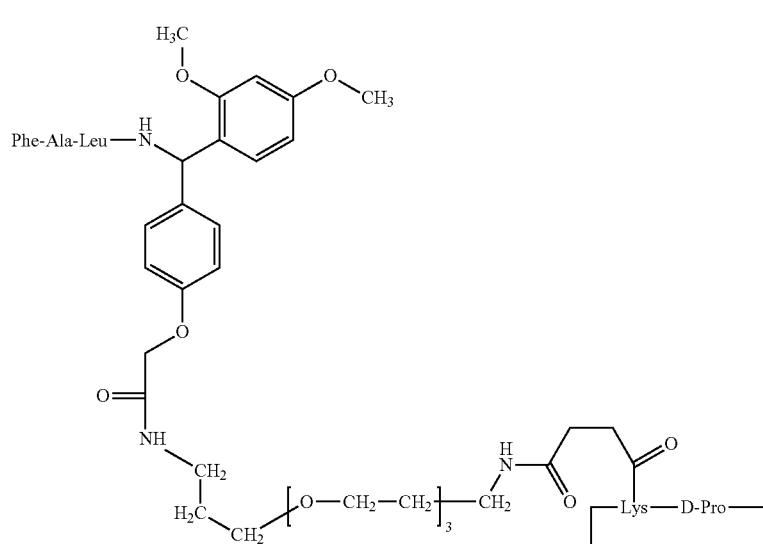

(ex-6e3-d1)

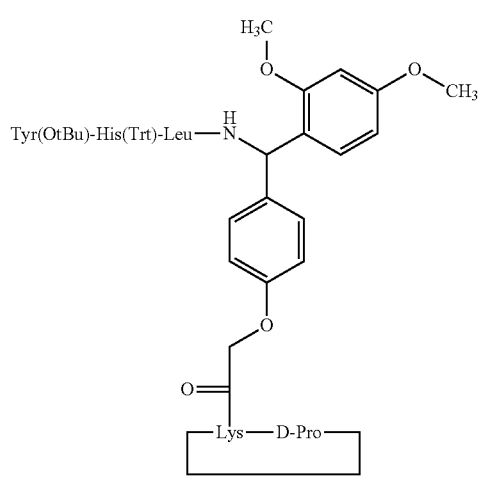

(ex-6e3-d2)

f1) Coupling of Compound of Formula (ex-4) with Compound of Formula (ex-6e3-d1) by HSPPS A mixture of compound of formula (ex-4) (255 mg, 1 eq), prepared according to example 4, HOBt (160 mg, 3 eq) and DIPCDI (161 microliter, 3 eq) in DCM (5 ml) was stirred for 60 min at RT, then added to a solution of compound of formula (ex-6e3-d1) (401 mg, 1.0 eq), prepared according to example 6e3), in DCM (1 ml), and then stirred at RT for 2 h. The coupling was monitored by HPLC method B3. The reaction mixture was washed with aqueous saturated NaHCO$_3$ (2×40 ml), 1M KHSO$_4$ aqueous solution (2×40 ml) and aqueous saturated NaCl (2×40 ml). The organic phase was dried over MgSO$_4$ and concentrated under reduced pressure to obtain 368.5 mg of compound of formula (ex-6f1) as an oil. (The core peptide below is disclosed as SEQ ID NO: 7)

f2) Addition of Compound of Formula (ex-4) with Compound of Formula (ex-6e3-d2) by HSPPS A mixture of compound of formula (ex-4) (295 mg, 1 eq), prepared according to example 4, HOBt (190 mg, 3 eq) and DIPCDI (188 microliter, 3 eq) in DCM (5 ml) was stirred for 20 min at RT, then added to a solution of compound of formula (ex-6e3-d2) (502 mg, 1.0 eq), prepared according to example 6e3), in DCM (1 ml), and then stirred at RT for 3.5 h. The coupling was monitored by HPLC method B3.

The reaction mixture was washed with aqueous saturated NaHCO$_3$ (2×40 ml), 1M KHSO$_4$ aqueous solution (2×40 ml) and aqueous saturated NaCl (2×40 ml). The organic phase was dried over MgSO$_4$ and concentrated under reduced pressure to obtain 372.8 mg of compound of formula (ex-6f2) as an oil. (The core peptide below is disclosed as SEQ ID NO: 6)

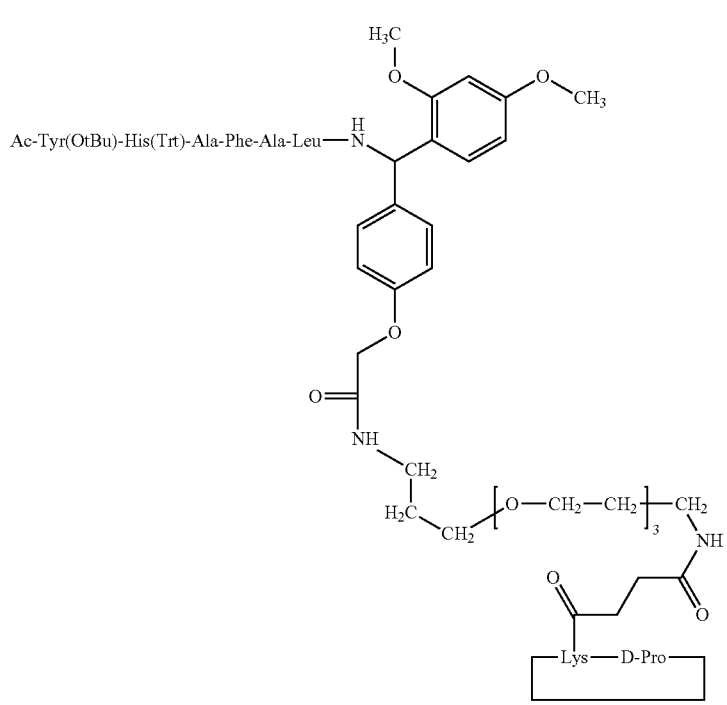

(ex-6f1)

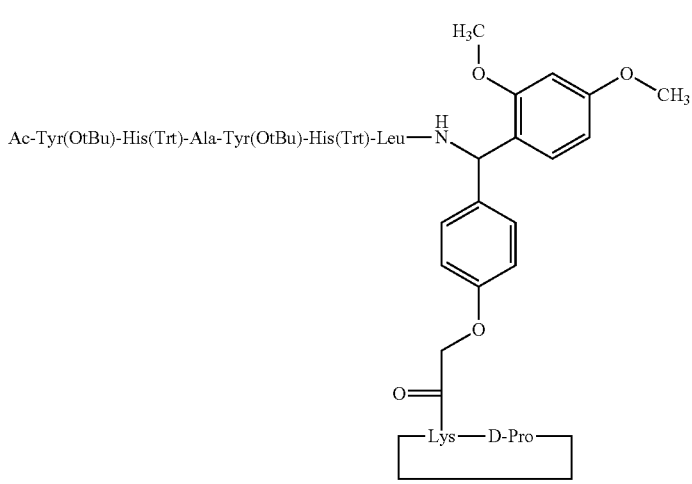

(ex-6f2)

Example 7

Use of the Handle Group HMPA. Preparation of Compound of Formula (ex-7h3)

a) Pre-Treatment of the HMPS Resin

HMPS resin (103.6 mg) was swelled with DCM (5×1 min; 3 ml each) and DMF (5×1 min; 3 ml each) at RT and then filtered.

b) Introduction of the First Amino Acid (D-Pro) of the Diketopiperazine Group Forming Dipeptidyl Linker on the Resin Fmoc-D-Pro-OH (132 mg, 4 eq) and DIPCDI (30 microliter, 2 eq) in DCM/DMF (15:1 (v/v), 2.5 ml) was added to a resin prepared according to example 7a). Then, DMAP (4.8 mg, 0.4 eq) in DCM (0.5 ml) was added and left to stand at RT for 2 h. The first amino acid was re-coupled using Fmoc-D-Pro-OH (132 mg, 4 eq) and DIPCDI (30 microliter, 2 eq) in DCM/DMF (15:1 (v/v), 2.5 ml) for 16 h at RT. After coupling, the resin was washed with DCM (5×1 min; 3 ml each) and with DMF (5×1 min; 3 ml each). Then, the resin was capped using acetic anhydride (46 microliter, 5 eq) and DIEA (86 microliter, 5 eq) in DMF (2.5 ml) for 30 min at RT. After capping, the resin was washed with DCM (5×1 min; 3 ml each) and with DMF (5×1 min; 3 ml each). Then the Fmoc group was removed by the method Fmoc-gr-rem.

A 0.98 mmol/g resin loading was determined by UV quantification (method description A; $V_A$: 100 ml, $V_B$: 10 ml and $V_C$: 1.4 ml).

c) Introduction of the Second Amino Acid (L-Dpr)

A mixture of Trt-L-Dpr(Fmoc)-OH (173 mg, 3 eq), HOBt (47 mg, 3 eq) and DIPCDI (47 microliter, 3 eq) in DMF (2 ml) was shaken for 5 min at RT, then added to a resin prepared according to example 7b). The mixture was left to stand at RT for 1 h. No re-coupling was required according to the ninhydrin test (method C). Then the resin was washed with DMF (5×1 min; 3 ml each) and with DCM (5×1 min; 3 ml each). Then the Fmoc group was removed by the method Fmoc-gr-rem.

d) Introduction of HMPA Handle Group

A mixture of HMPA (55 mg, 3 eq), HOBt (47 mg, 3 eq) and DIPCDI (47 microliter, 3 eq) in DMF (2 ml) was added to a resin prepared according to example 7c), and then left to stand at RT for 1 h. No re-coupling was required, according to the ninhydrin test (method C). Then the resin was washed with DMF (5×1 min; 3 ml each) and with DCM (5×1 min; 3 ml each).

e) Introduction of Fmoc-Xaa-OH by SPPS

Starting with a resin prepared according to example 7d), 1. Fmoc-Leu-OH was incorporated following the reaction cycle description (viii), and then 2. Fmoc-Ala-OH and 3. Fmoc-Phe-OH were respectively incorporated following the reaction description (ix).

f1) Reaction Cycle Description (viii)

Fmoc-Leu-OH (144 mg, 4 eq) and DIPCDI (30 microliter, 2 eq) in DCM/DMF (15:1 (v/v), 2.5 ml) was added to a resin prepared according to example 7d). Then, DMAP (4.8 mg, 0.4 eq) in DCM (0.5 ml) was added and left to stand at RT for 2 h. The amino acid was re-coupled using Fmoc-Leu-OH (144 mg, 4 eq) and DIPCDI (30 microliter, 2 eq) in DCM/DMF (15:1 (v/v), 2.5 ml) for 16 h at RT. After coupling, the resin was washed with DCM (5×1 min; 3 ml each) and with DMF (5×1 min; 3 ml each). Then, the resin was capped using acetic anhydride (46 microliter, 5 eq) and DIEA (86 microliter, 5 eq) in DMF (2.5 ml) for 30 min at RT. After capping, the resin was washed with DCM (5×1 min; 3 ml each) and with DMF (5×1 min; 3 ml each). Then the Fmoc group was removed by the method Fmoc-gr-rem. A 0.94 mmol/g resin loading was determined by UV quantification (method description A; $V_A$: 100 ml, $V_B$: 10 ml and $V_C$: 1.4 ml).

f2) Reaction Cycle Description (ix)

A mixture of the respective Fmoc-Xaa-OH (3 eq), HOBt (47 mg, 3 eq) and DIPCDI (47 microliter, 3 eq) in DMF (2 ml) was added to a resin and then left to stand at RT for 1 h. No re-coupling was required, according to the ninhydrin test (method C). Then the resin was washed with DMF (5×1 min;

3 ml each) and with DCM (5×1 min; 3 ml each). The Fmoc group was removed by according to method Fmoc-gr-rem.

g) Analysis—Cleavage of the Peptide from the Handle Group and Thereby from the Resin A small portion of resin (5 mg), obtained according to example 7e), was cleaved from the resin by treating the resin with 1 ml of a mixture of 95% (v/v) TFA, 2.5% (v/v) TIS and 2.5% (v/v) water for 1 h at RT. The RP-HLPC analysis confirmed identity of Phe-Ala-Leu-NH$_2$ (method description B1, 5 to 100 of mobile phase B).

h) Trt Protecting Group Removal of the L-Dpr of the Diketopiperazine Group Forming Dipeptidyl Linker, Formation of the Diketopiperazine Residue Comprising C-Terminal Protecting Group and Cleavage from the Resin Formation of the diketopiperazine residue comprising C-terminal protecting group and cleavage of the DKP-peptides from the resin prepared according to example 7e), is brought about in analogous manner as described in example 1.4a with the amounts of reagents and solvent adapted to the amount of peptidyl-resin:

h1) Trt Group Deprotection

Treatment of the compound prepared according to example 7e) with 0.2% (v/v) TFA, 2% (v/v) TIS in DCM (2×5 min, 2 ml each).

h2) Neutralization

The treatment with 5% (v/v) DIEA in DCM (2×5 min; 2 ml each)

h3) Formation of the Diketopiperazine Residue Comprising C-Terminal Protecting Group and Cleavage from the Resin Then treatment with 5% (v/v) piperidine in THF (2×5 min; 2 ml each).

THF was removed by evaporation under vacuum and the resulting compound of formula (ex-7h3) was analyzed by RP-HPLC-ESMS (method description B2, 5 to 100 of mobile phase B, [(M+H)/2]+: 679, where M is the MW of compound of formula (ex-7h3)).

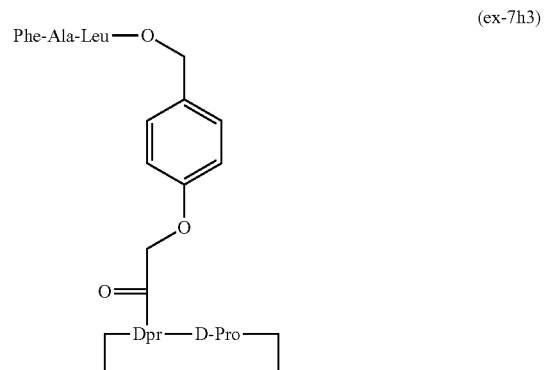

(ex-7h3)

SEQUENCE LISTING FREE TEXT

<210>1
<223>SEQ ID 1 is abbreviated with [T20-1-36]
<210>2
<223>SEQ ID 2 is abbreviated with [T20-27-36]
<210>3
<223>SEQ ID 3 is abbreviated with [T20-17-26]
<210>4
<223>SEQ ID 4 is abbreviated with [T20-17-36]
<210>5
<223>SEQ ID 5 is comprised in formulae (ex-5i)
<210>6
<223>SEQ ID 6 is comprised in formula (ex-6f2)
<210>7
<223>SEQ ID 7 is comprised in formulae (ex-6f1)

---

SEQUENCE LISTING

<160> NUMBER OF SEQ ID NOS: 7

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 2

Asp Lys Trp Ala Ser Leu Trp Asn Trp Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Lys Asn Glu Gln Glu Leu Leu Glu Leu
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Lys Asn Glu Gln Glu Leu Leu Glu Leu Asp Lys Trp Ala Ser Leu
1               5                   10                  15

Trp Asn Trp Phe
            20

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr(tBu)
<220> FEATURE:
<221> NAME/KEY: MOD_RES
<222> LOCATION: (2)..(2)
<223> OTHER INFORMATION: His(Trt)

<400> SEQUENCE: 5

Tyr His Ala Phe Ala Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr(OtBu)
<220> FEATURE:
<221> NAME/KEY: MOD_RES
<222> LOCATION: (2)..(2)
<223> OTHER INFORMATION: His(Trt)
<220> FEATURE:
<221> NAME/KEY: MOD_RES
<222> LOCATION: (4)..(4)
<223> OTHER INFORMATION: Tyr(OtBu)
<220> FEATURE:
```

```
<221> NAME/KEY: MOD_RES
<222> LOCATION: (5)..(5)
<223> OTHER INFORMATION: His(Trt)

<400> SEQUENCE: 6

Tyr His Ala Tyr His Leu
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr(OtBu)
<220> FEATURE:
<221> NAME/KEY: MOD_RES
<222> LOCATION: (2)..(2)
<223> OTHER INFORMATION: His(Trt)

<400> SEQUENCE: 7

Tyr His Ala Phe Ala Leu
1               5
```

The invention claimed is:

1. A method for the preparation of a peptide C-PEP, wherein C-PEP comprises a peptidyl radical PEP-C and a C-terminal protecting group DKP-PG, wherein DKP-PG comprises a handle group HG, an optional spacer group SG, and a diketopiperazine residue DKP;

SG is a spacer group conventionally used in peptide chemistry;

DKP is a diketopiperazine derived from a dipeptide DPR consisting of a C-terminal residue Xaa1 and an N-terminal residue Xaa2, wherein Xaa2 has a side chain functional group FG;

wherein Xaa1 is selected from the group consisting of naturally occurring alpha amino acid residues, alpha-N-methylamino acid residues, L-Hpr residue, D-Hpr residue, DL-Hpr residue, 2-($C_{1-5}$-alkyl)-D-amino acid residues, 2-($C_{1-5}$-alkyl)-L-amino acid residues, 2-($C_{1-5}$-alkyl)-DL-amino acid residue and an HypX residue; wherein HypX is a compound of formula:

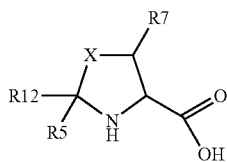

wherein

X is O, S or C(R13)R14;

R5, R7, R12, R13 and R14 are identical or different and independently from each other selected from the group consisting of hydrogen, $C_{1-4}$ alkyl and O—R8;

R8 is a protecting group conventionally used for side chain protection in peptide chemistry, or a substituent of formula (Sub-R8);

wherein m8 is 1, 2, 3, 4, 5, 6, 7, 8, 9 or 10;

R9 is $C_{1-4}$alkyl;

Xaa2 is selected from the group consisting of L-Lys residue, D-Lys residue, DL-Lys residue, L-Orn residue, D-Orn residue, DL-Orn residue, L-4-aminoproline residue, D-4-aminoproline residue, DL-4-aminoproline residue, L-alpha,gamma-diaminobutanoic acid residue, D-alpha,gamma-diaminobutanoic acid residue, DL-alpha,gamma-diamino-ibutanoic acid residue, L-alpha, beta-diaminopropanoic acid residue, D-alpha,beta-diaminopropanoic acid residue, DL-alpha,beta-diaminopropanoic acid residue, L-Ser residue, D-Ser residue, DL-Ser residue, L-Thr residue, D-Thr residue, DL-Thr residue, L-Cys residue, D-Cys residue, DL-Cys residue, L-homocysteine residue, D-homocysteine residue, DL-homocysteine residue, L-Asp residue, D-Asp residue, DL-Asp residue, L-Glu residue, D-Glu residue and DL-Glu residue;

PEP-C is connected via its C-terminal amino acid XaaC$^{(1)}$ to HG;

HG is either directly connected to a side chain functional group of Xaa2 (FG), or, if a SG is present, HG is connected to SG and SG is connected to FG;

HG is a handle group selected from the group consisting of HGF-I, HGF-II, HGF-III, HGF-IV, HGF-V and HGF-VI, -continued (HGF-I)

(HGF-VI)

(HGF-II)

(HGF-III)

(HGF-IV)

(HGF-V)

wherein
(*) denotes the bond between HG and the carbonyl carbon or the side chain of the C-terminal amino acid of PEP-C,
(**) denotes the bond between HG and SG when a SG is present, or denotes the bond between HG and FG when no SG is present;
R1, R2, R3, R4, R10 and R11 are identical or different and independently from each other selected from the group consisting of hydrogen and O—$C_{1-4}$ alkyl,
s1-1, s2, s3, s4 and s6 are identical or different and independently from each other selected from the group consisting of 1, 2, 3 and 4,
s5-1 is 0, 1, 2, 3 or 4,
s1-2, s5-2 and s5-3 are identical or different and independently from each other 0 or 1,
T1-1 is O or NH,
T1-2 and T5-1 are O;
wherein said method comprises providing PEP-C-DKP-L-ResinA;
wherein PEP-C-DKP-L-ResinA comprises PEP-C connected to a resin DKP-L-ResinA;
wherein DKP-L-ResinA comprises a ResinA connected to a DKP-PG forming linker DKP-L,
wherein ResinA is a resin used conventionally as solid phase in SPPS,
and DKP-L comprises HG, optionally SG, and DPR, with the carboxylic acid group of Xaa1 being connected to ResinA;
and cleaving the PEP-C-DKP-L-ResinA under conditions to promote an intramolecular ring formation in reaction (INRIFO), wherein the INRIFO is a reaction of the alpha amino group of Xaa2, with the carboxylic acid group of Xaa1 to form, DKP, thereby simultaneously cleaving Xaa1 from ResinA and forming C-PEP.

2. A method according to claim 1, wherein PEP-C is prepared by a solid phase peptide synthesis SPPS; and ResinA is chosen in such a way that the bond between ResinA and Xaa1 is not cleaved during SPPS of PEP-C.

3. A method according to claim 1 wherein the DKP-PG forming linker DKP-L is prepared by a method comprising:
coupling Xaa2 to Xaa1;
optionally coupling SG to Xaa2, if SG is present in DKP-L;
coupling HG either to SG, if SG is present in DKP-L, or to Xaa2;
wherein DKP-PG, DKP-L, DKP, Xaa2, Xaa1, HG and SG are defined according to claim 1.

4. A method according to claim 1 wherein the DKP-L-ResinA, is prepared according to a method comprising method(X1) or method(X2);

wherein method(X1) comprises
  coupling the amino acid Xaa1 to ResinA;
  coupling the amino acid Xaa2 to Xaa1;
  optionally coupling SG to the side chain of Xaa2, if SG is present in DKP-L-ResinA; and
  coupling HG either to SG, if SG is present in DKP-L-ResinA, or to Xaa2; and
wherein method(X2) comprises
  coupling DKP-L to ResinA;
wherein DKP-L-ResinA, ResinA, DKP-PG, DKP-L, DKP, Xaa2, Xaa1, HG and SG are defined according to claim 1.

5. A method according to claim 1, wherein HG is selected from the group consisting of HGF-I, HGF-IV and HGF-VI.

6. A method according to claim 1, wherein HG is selected from the group consisting of HG-Ia, HG-Ib, HG-Ic, HG-Id, HG-II, HG-III, HG-IVa, HG-IVb, HG-Va, HG-Vb and HG-VI,

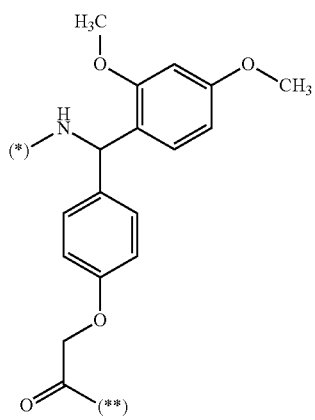
(HG-Ia)

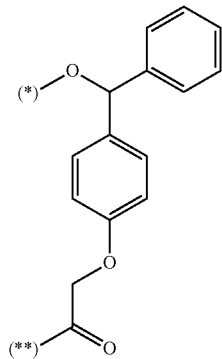
(HG-Ib)

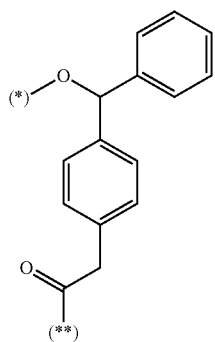
(HG-Ic)

-continued

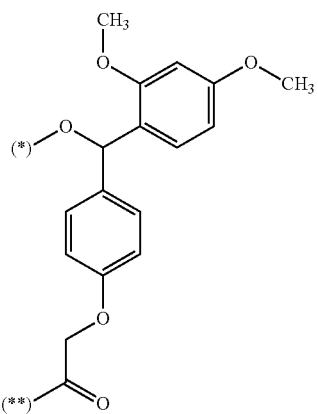
(HG-Id)

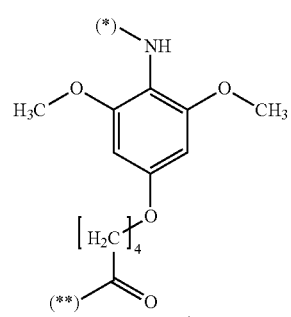
(HG-II)

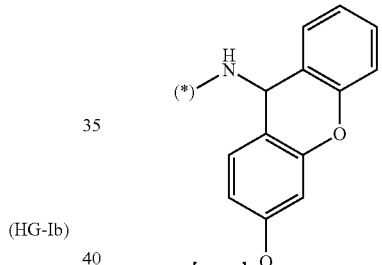
(HG-III)

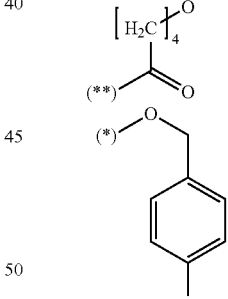
(HG-IVa)

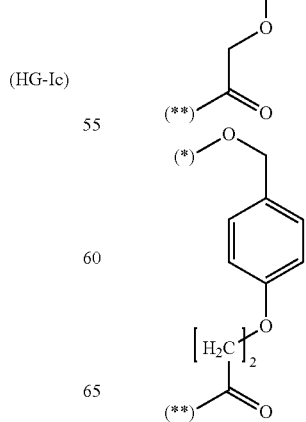
(HG-IVb)

(HG-Va)
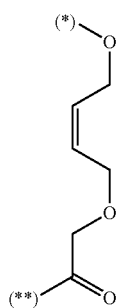
(HG-Vb)
(HG-VI)
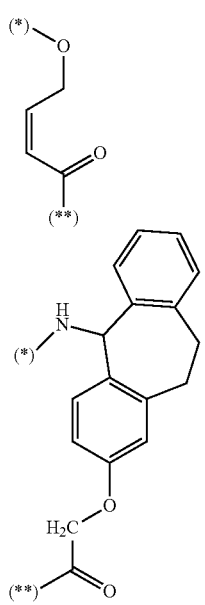
wherein
(*) and () are as defined in claim 1**.
7. A method according to claim 1, wherein
SG is a spacer group selected from the group consisting of SG-I, SG-II, SG-III, SG-IV, SG-V, SG-VI, and SG-VII;
(SG-I)
(SG-II)
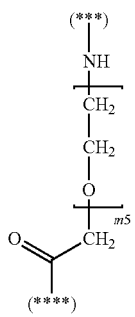
(SG-III)
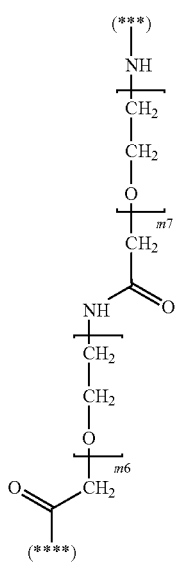
(SG-IV)
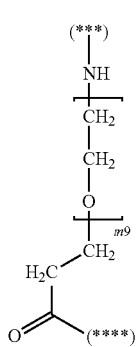
(SG-V)
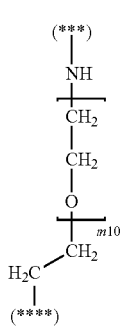

-continued

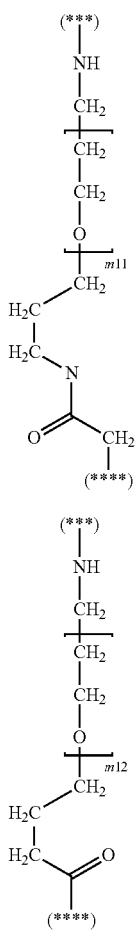

(SG-VI)

(SG-VII)

wherein m1, m5, m6, m7, m9, m10, m 11 and m12 are identical or different and independently from each other an integer of 1 to 500;
m2, m3 and m4 are identical or different and independently from each other 1, 2, 3 or 4,
(***) is the bond from SG to HG when a SG is present,
(****) is the bond between SG and Xaa2 when a SG is present,
wherein HG and Xaa2 are defined according to claim 1.

8. A method according to claim 1, wherein
Xaa1 is selected from the group consisting of L-N-methylglycine residue, D-N-methylglycine residue, DL-N-methylglycine residue, L-N-methylphenylalanine residue, D-N-methylphenylalanine residue, DL-N-methylphenylalanine residue, L-Pro residue, D-Pro residue, DL-Pro residue, side chain protected L-4Hyp residue, side chain protected D-4Hyp residue, side chain protected DL-4Hyp residue, L-4Hpr residue, D-Hpr residue and DL-Hpr residue.

9. A method according to claim 1, wherein
Xaa2 is selected from the group consisting of L-Lys residue, D-Lys residue, DL-Lys residue, L-Orn residue, D-Orn residue, DL-Orn residue, L-4-aminoproline residue, D-4-aminoproline residue, DL-4-aminoproline residue, L-alpha,gamma-diaminobutanoic acid residue, D-alpha,gamma-diaminobutanoic acid residue, DL-alpha,gamma-diaminobutanoic acid residue, L-alpha,beta-diaminopropanoic acid residue, D-alpha,beta-diaminopropanoic acid residue, DL-alpha,beta-diaminopropanoic acid residue, L-Ser residue, D-Ser residue, DL-Ser residue, L-Thr residue, D-Thr residue, DL-Thr residue, L-Cys residue, D-Cys residue, DL-Cys residue, L-homocysteine residue, D-homocysteine residue, DL-homocysteine residue, L-Asp residue, D-Asp residue, DL-Asp residue, L-Glu residue, D-Glu residue and DL-Glu residue.

10. A method according to claim 1, wherein
ResinA is selected from the group consisting of hydroxymethylpolystyrene (HMPS) resins, polyethylene glycol (PEG) based resins, polystyrene resin, p-benzyloxybenzyl alcohol resins, chloromethyl polystyrene-divinylbenzene resins, and poly(vinyl alcohol)-graft-poly(ethylene glycol) (PVA-g-PEG) resins.

11. A method for the preparation of a peptide,
comprising preparing a peptide C-PEP according to the method of claim 1;
then
coupling said C-PEP with an N-terminally protected amino acid or with an N-terminally protected peptide by homogeneous solution phase peptide synthesis HSPPS.

12. A compound selected from the group consisting of C-PEP and PEP-C-DKP-L-ResinA; with C-PEP and PEP-C-DKP-L-ResinA defined according to claim 1.

* * * * *